(12) United States Patent
Shraibom

(10) Patent No.: US 9,669,062 B2
(45) Date of Patent: *Jun. 6, 2017

(54) MOLECULAR AND HERBAL COMBINATIONS FOR TREATING PSORIASIS

(71) Applicant: Sirbal, Ltd., Limassol (CY)

(72) Inventor: Nadav Shraibom, Herzelia (IL)

(73) Assignee: Sirbal Ltd., Limassol (CY)

( * ) Notice: Subject to any disclaimer, the term of this patent is extended or adjusted under 35 U.S.C. 154(b) by 0 days.

This patent is subject to a terminal disclaimer.

(21) Appl. No.: 14/872,138

(22) Filed: Sep. 30, 2015

(65) Prior Publication Data

US 2016/0113983 A1    Apr. 28, 2016

Related U.S. Application Data

(63) Continuation of application No. 14/752,344, filed on Jun. 26, 2015, which is a continuation of application No. 13/900,525, filed on May 22, 2013, now Pat. No. 9,095,606, which is a continuation-in-part of application No. 13/361,978, filed on Jan. 31, 2012, which is a continuation-in-part of application No. 13/152,039, filed on Jun. 2, 2011, which is a continuation-in-part of application No. 13/018,435, filed on Feb. 1, 2011, now Pat. No. 8,541,382.

(60) Provisional application No. 61/413,430, filed on Nov. 13, 2010.

(51) Int. Cl.
| A61K 36/64 | (2006.01) |
|---|---|
| A61K 36/708 | (2006.01) |
| A61K 36/355 | (2006.01) |
| A61K 36/815 | (2006.01) |
| A61K 36/185 | (2006.01) |
| A61K 36/65 | (2006.01) |
| A61K 36/73 | (2006.01) |
| A61K 36/804 | (2006.01) |
| A61K 9/00 | (2006.01) |

(52) U.S. Cl.
CPC .......... *A61K 36/708* (2013.01); *A61K 9/0019* (2013.01); *A61K 36/185* (2013.01); *A61K 36/355* (2013.01); *A61K 36/64* (2013.01); *A61K 36/65* (2013.01); *A61K 36/73* (2013.01); *A61K 36/804* (2013.01); *A61K 36/815* (2013.01)

(58) Field of Classification Search
None
See application file for complete search history.

(56) References Cited

U.S. PATENT DOCUMENTS

| 6,153,208 | A  | * | 11/2000 | McAtee | A61K 8/0208 424/401 |
|---|---|---|---|---|---|
| 6,338,855 | B1 | * | 1/2002 | Albacarys | A61K 8/0208 424/402 |
| 6,825,161 | B2 | * | 11/2004 | Shefer | A61K 8/11 510/438 |
| 7,691,419 | B2 | * | 4/2010 | DiLeva | A61K 8/678 424/725 |
| 2002/0164387 | A1 | * | 11/2002 | Wei | A23F 3/34 424/746 |
| 2005/0271692 | A1 | * | 12/2005 | Gervasio-Nugent | A61K 8/0208 424/401 |
| 2006/0039986 | A1 | * | 2/2006 | Okamoto | A61K 8/0241 424/489 |
| 2012/0027876 | A1 | * | 2/2012 | Ford | A61K 31/715 424/690 |
| 2012/0269912 | A1 | * | 10/2012 | Roberts | A61K 9/0056 424/736 |

FOREIGN PATENT DOCUMENTS

| CN | CH 101306175 | A | * | 11/2008 |
|---|---|---|---|---|
| CN | 101428097 | A | * | 5/2009 |
| CN | 101637585 | A | * | 2/2010 |
| CN | 101745073 | A | * | 6/2010 |
| CN | 1829293 | A | * | 9/2010 |
| CN | 101829261 | A | * | 10/2010 |
| SU | 248161 | A | * | 12/1962 |

OTHER PUBLICATIONS

Tierra, M. "Treating Cancer with Herbs: An Integrative Approach", 2003. pp. 81, 93, 187, 211.*

* cited by examiner

*Primary Examiner* — Chris R Tate
(74) *Attorney, Agent, or Firm* — SF Bay Area Patents, LLC; Andrew V. Smith

(57) ABSTRACT

A treatment regimen for psoriasis includes administering to a patient diagnosed with psoriasis periodic doses of a combination including Sheng Di Huang, Da Huang and Jin Yin Hua, or a combination of the above with Mu Dan Pi, Di Gu Pi, Xian He Cao and Chun Gen Pi.

15 Claims, 24 Drawing Sheets

Group 1: 3-HX (1:4); Topical

Group 2: 3-HX (1:8); Topical

Group 3: 3-HX (500mg/kg); Oral

Group 4: 3-HX (1000mg/kg); Oral

Group 5: D & E; Topical

Group 6: D & E; Oral

Group 7: TPA Control (Right Ear) & Vehicle Control (Left Ear)

Group 1: 3-HX (1:4); Topical

Group 2: 3-HX (1:8); Topical

Group 3: 3-HX (500mg/kg); Oral

Group 4: 3-HX (1000mg/kg);
Oral

Group 5: D & E; Topical

Group 6: D & E; Oral

Group 7: TPA Control (Right Ear)

Group 7: Vehicle control (Left Ear)

MOLECULAR AND HERBAL COMBINATIONS FOR TREATING PSORIASIS

PRIORITY

This application is a Continuation of U.S. patent application Ser. No. 14/752,344, filed on Jun. 26, 2015; which is a Continuation of U.S. patent application Ser. No. 13/900,525, filed May 22, 2013, now U.S. Pat. No. 9,095,606; which is a Continuation-in-Part (CIP) of U.S. patent application Ser. No. 13/361,978, filed Jan. 31, 2012; which is a Continuation-in-Part (CIP) which claims the benefit of priority to U.S. patent application Ser. No. 13/152,039, filed Jun. 2, 2011; which is a Continuation-in-Part (CIP) of U.S. patent application Ser. No. 13/018,435, filed Feb. 1, 2011, now U.S. Pat. No. 8,541,382; which claims the benefit of priority to U.S. provisional patent application No. 61/413,430, filed Nov. 13, 2010. U.S. patent application Ser. Nos. 13/218,432 and 13/218,437, each filed Aug. 28, 2011, are also related to this application. Each of these applications are incorporated by reference.

BACKGROUND OF THE INVENTION

1. Field of the Invention

The present invention relates generally to disease treatments, including treatments for psoriasis. More specifically it concerns the use of emodin and/or digoxin and/or combinations of certain herbs, certain herbal extracts and/or certain molecular components of certain herbs to reduce white cell count or otherwise treat one or more of these diseases. Example compounds and/or molecules include cardiac glycosides such as Digoxin and Quabain in combination with Emodin and its analogs for the treatment of disease. Example herbs that may be combined and/or from which certain compounds and/or molecules may be extracted and combined include Da Huang and Sheng Di Huang, as well as Jin Yin Hua, and Mu Dan Pi, Di Gu Pi, Xian He Cao, and Chun Gen Pi.

2. Description of the Related Art

Herbal medicines are still prevalent, and serve the medicinal needs of a large population around the world. The global herbal medicine market is currently worth around $30 billion. There is an increased effort for the isolation of bioactive phytochemicals from herbs for their possible usefulness in the control of various ailments. Determining molecular structure and mechanisms of action of bioactive phytochemicals are equally important for providing the evidence for their efficacy as well as herbal preparations, which could also potentially lead to the pharmaceutical development of synthetic or semi-synthetic drugs. About herbal medicines in cancer studies, several previous studies demonstrate that certain phytochemicals present in medicinal herbs exert anti-cancer activities. Among three structurally related anthraquinones, including emodin, physcion, and chrysophanol, emodin showed the most potent cytotoxic effects on tumor cells. Emodin (1,3,8-trihydroxy-6-methyl-anthraquinone) and aloe-emodin, 1,8-dihydroxy-3-hydroxymethyl-9,10-anthracenedione as shown a chemotherapeutic activity in vitro and in animal models for the treatment of various types of cancers, including bladder cancer, lung cancer, and hepatoma, and leukemia. Aloe-emodin is a natural anthraquinone compound that is present in some traditional medicinal plants such as Rhei Rhizoma and Rheum palmatum. Interestingly, aloe-emodin has been found to have lesser cytotoxicity towards the normal human cells.

Plant-derived cardiac glycosides such as digoxin are used for the treatment of congestive heart failure and other cardiac disorders. Their main pharmacologic actions are mediated through inhibition of the sodium pump, Na+- and K+-dependent ATPase (NKA) 1 (EC 3.6.3.9). NKA, a ubiquitous membrane cationic transporter protein, controls normal membrane potential in all eukaryotic cells by maintaining high K+ and low Na+ concentrations. It consists of a catalytic subunit and a β glycoprotein subunit. Studies have suggested that plant-derived cardiac glycosides regulate some cellular processes, such as proliferation and apoptosis, in a variety of cancer cells.

The following are incorporated by reference: WO2004/052294A2, WO2007/130124A1, and US20090018088.

DETAILED DESCRIPTIONS OF THE EMBODIMENTS

Figure 1:
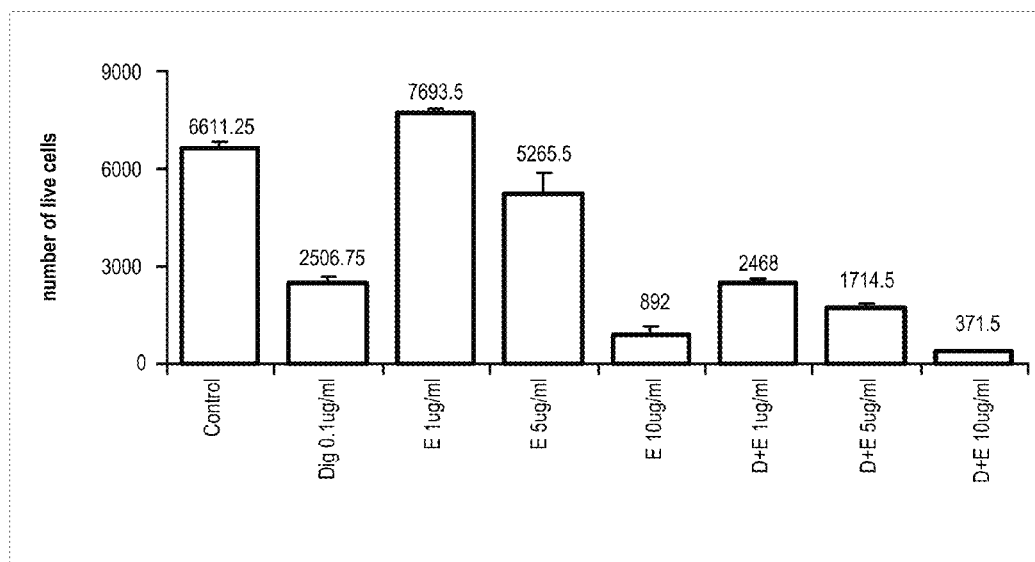
FIG. 1 illustrates the effect of on proliferation of digoxin, emodin, and their combination on NB4 leukemic cells.

A method of treating leukemia or other cancer is provided. The treatment includes administering to a patient diagnosed with the leukemia or other cancer a regimen that includes periodic doses of emodin or digoxin, or both, alone or in combination with herbs, herbal extracts, and/or compounds or molecules extracted from certain herbs or herbal extracts. Seven such herbs when used in certain combinations with emodin or digoxin, or both, exhibit enhanced potency in killing cancer cells and/or reducing white cell counts. Among these are seven herbs including Da Huang, Sheng Di Huang, and Jin Yin Hua, as well as Mu Dan Pi, Di Gu Pi, Xian He Cao, and Chun Gen Pi.

Administration in a treatment regimen of certain combinations of emodin or digoxin, or both, with one or two or more of these herbs serve to reduce white cell count, and are provided as embodiments herein. Specific embodiments include advantageous combinations of emodin or digoxin, or both, with Da Huang and/or with Sheng Di Huang, as indicated below and in U.S. patent application Ser. No. 13/018,435, which is incorporated by reference, as well as the combination of emodin or digoxin, or both, with Jin Yin Hua, and/or with Da Huang and/or Sheng Di Huang with Jin Yin Hua. Further embodiments include combinations of emodin or digoxin, or both, with DaHuang and/or Sheng Di Huang with one or more of Mu Dan Pi, Di Gu Pi, Xian He Cao, and/or Chun Gen Pi. Other embodiments include combinations of emodin or digoxin, or both, with Da Huang and/or Sheng Di Huang with Jin Yin Hua and one or more of Mu Dan Pi, Di Gu Pi, Xian He Cao, and/or Chun Gen Pi. Further embodiments include combinations of emodin or digoxin, or both, with Jin Yin Hua with one or more of Mu Dan Pi, Di Gu Pi, Xian He Cao, and Chun Gen Pi. Other embodiments include combinations of emodin or digoxin, or both, with two of more of Mu Dan Pi, Di Gu Pi, Xian He Cao, and/or Chun Gen Pi.

Contained within each of the seven herbs are several molecular constituents. An observed reduction of the white cell count owing to a treatment regimen of periodic doses of a combination of emodin or digoxin, or both, with one or more of the seven herbs can be as a result of various combinations of active molecules with emodin and/or digoxin which are themselves contained in Da Huang and Sheng Di Huang, respectively. Even combinations of emodin and Da Huang to enhance the concentration of emodin and/or digoxin and Sheng Di Huang to enhance the concentration of digoxin are advantageously provided to treat diseases such as cancer.

A method of treating Acute Lymphoblastic Leukemia (ALL) is provided including administering to a patient diagnosed with ALL a treatment regimen that includes periodic doses of a combination of emodin or digoxin, or both, with Vincristine Sulfate, Cyclophosphamide, Doxorubicin Hydrochloride, Methotrexate, Clofarabine, Cytarabine, Dasatinib, Daunorubicin Hydrochloride, Gleevec (Imatinib Mesylate), Nelarabine, or Oncaspar (Pegaspargase), or combinations thereof.

A method of treating Acute Monocytic Leukemia (AML) is also provided including administering to a patient diagnosed with AML a treatment regimen that includes periodic doses of a combination of emodin or digoxin, or both, with Cyclophosphamide, Cytarabine, Doxorubicine, Daunorubicin, or Vincristine, or combinations thereof.

A method of treating Melanoma is also provided including administering to a patient diagnosed with Melanoma a treatment regimen that includes periodic doses of a combination of emodin or digoxin, or both, with Aldesleukin (Proleukin), Dacarbazine, Ipilimumab (Yervoy), or Peginterferon-alpha or combinations thereof.

Another method of treating Melanoma is provided including administering to a patient diagnosed with Melanoma a treatment regimen that includes periodic doses of a combination of emodin or digoxin, or both, with Paclitaxel, Cisplatin, Carboplatin, Vinblastine, Vincristine or Vindesine, or combinations thereof. The treatment regimen may also include Aldesleukin (Proleukin), Dacarbazine, Ipilimumab (Yervoy) or Peginterferon-alpha, or combinations thereof.

A method of treating multiple myeloma is provided including administering to a patient diagnosed with multiple myeloma a treatment regimen that includes periodic doses of a combination of emodin or digoxin, or both, with Talidomid, Revlomid or Valkade, or combinations thereof.

A method of treating chronic myeloid leukemia (CML) is provided including administering to a patient diagnosed with CML a treatment regimen that includes periodic doses of a combination of emodin or digoxin, or both, with Gleevac, Dasatinib, Sprycel, Nilotinib, Tasigna, Hydroxyurea or Hydrea, or combinations thereof.

A method of treating non-Hodgkins lymphoma is provided including administering to a patient diagnosed with non-Hodgkins lymphoma a treatment regimen that includes periodic doses of a combination of emodin or digoxin, or both, with an RCHOP combination, including Retuximab or Mabtera, or both and a combination of Cyclophosphamide, and Doxorubicin Hydrochloride, Hydroxydaunomycin, or Adriamycin, or a combination thereof, and Vincristine Sulfate or Oncovin, or both, and Prednisone.

A method of treating Hodgkins lymphoma is provided including administering to a patient diagnosed with Hodgkins lymphoma a treatment regimen that includes periodic doses of a combination of emodin or digoxin, or both, with an ABVD combination, including Doxorubicin Hydrochloride, Hydroxydaunomycin, or Adriamycin, or a combination thereof, and Bleomycin, and Vinblastine, and Dacarbazine or Procarbazine or both.

A method of treating colon cancer is provided including administering to a patient diagnosed with colon cancer a treatment regimen that includes periodic doses of a combination of emodin or digoxin, or both, with Folfiri q Folfox combination, including a combination of fluorouracil –5Fu, Oxaliplatinim, irinotecan, and leucovorin or subset thereof.

A method of treating non-small cell lung cancer (NSCLC) is provided including administering to a patient diagnosed with colon cancer a treatment regimen that includes periodic doses of a combination of emodin or digoxin, or both, with Cisplatinum, etoposide, mitomycin C, or vindesine, or a combination thereof.

A method of treating prostate cancer is provided including administering to a patient diagnosed with prostate cancer a treatment regimen that includes periodic doses of a combination of emodin or digoxin, or both, with Taxotere, Paclitaxel, Docetaxel, Mitoycin C, Doxorubicin, Mitozantrone, vinblastine, Etoposide, or Estramustine Phosphate, or combinations thereof.

A method of treating breast cancer is provided including administering to a patient diagnosed with prostate cancer a treatment regimen that includes periodic doses of a combination of emodin or digoxin, or both, with cyclophosphamide, doxorubicin, Adriamicin, fluorouracil, 5fu, or Taxol, or combinations thereof.

A method of treating epidermal oral carcinoma is provided including administering to a patient diagnosed with prostate cancer a treatment regimen that includes periodic doses of a combination of emodin or digoxin, or both, with Taxol, Carboplatinum, or Erbitux, or combinations thereof.

A method of treating glioblastoma is provided including administering to a patient diagnosed with glioblastoma a treatment regimen that includes periodic doses of a combination of emodin or digoxin, or both, with TEMODAL, temozolomide, or Avastin, or combinations thereof.

Methods of relieving side effects of chemotherapy, enhancing antitumor activity, improving quality of life of a patient undergoing chemo, inhibiting growth of tumors, increasing a therapeutic index of cancer therapeutic compounds for treating cancer, treating a disease, and modulating hematological or immunological activity for the treatment of a disease, are also provided, including administering a combination of one or more of emodin or digoxin or Sheng Di Huang or Da Huang or Jin Yin Hua, along with one or more of the following: Vincristine Sulfate, Cyclophosphamide, Doxorubicin Hydrochloride, Methotrexate, Clofarabine, Cytarabine, Dasatinib, Daunorubicin Hydrochloride, Gleevec (Imatinib Mesylate), Nelarabine, Oncaspar (Pegaspargase) Doxorubicine, Daunorubicin, Vincristine Paclitaxel, Cisplatin, Carboplatin, Vinblastine, Vincristine, Vindesine, Aldesleukin (Proleukin), Dacarbazine, Ipilimumab (Yervoy), Talidomid, Revlomid, Gleevac, Dasatinib, Sprycel, Nilotinib, Tasigna, Hydroxyurea, Hydrea, Valkade, Peginterferon-alpha, an RCHOP combination, or an ABVD combination, Folfiri q Folfox, Cisplatinum, etoposide, mitomycin C, vindesine Taxotere, Paclitaxel, Docetaxel, Mitoycin C, Doxorubicin, Mitozantrone, vinblastine, Etoposide, Estramustine Phosphate, cyclophosphamide, doxorubicin, Adriamicin, fluorouracil, 5fu, Taxol, Carboplatinum, Erbitux, TEMODAL, temozolomide, or Avastin, or combinations thereof.

Advantageous effects of a treatment regimen may be bolstered by further combinations with active ingredients and/or by one or more buffer molecules or one or more molecules serving as some helpful vehicle for the active molecules. The chemistries and pharmacologies of the seven herbs are summarized below.

In certain embodiments, certain parts of the seven herbs are used such as the roots, stems, leaves, husks, branches, barks, sap, or kernels or combinations thereof. For example, for Da Huang at least the root may be used. For Sheng Di Huang, at least dried root tuber may be used. For Jin Yin Hua, at least dried flower may be used. For Mu Dan Pi, at least dried root bark may be used. For Di Gu Pi, at least dried root bark may be used. For Xian He Cao, at least dried aerial part of Agrimonia Pilosa Ledeb may be used. For Chun Gen Pi, at least dried bark of the root or stem may be used.

In certain further embodiments, emodin or digoxin, or both, with the two herbs Sheng Di Huang and Da Huang, or two or more of the three herbs including Jin Yin Hua, or combinations of the seven herbs including Mu Dan Pi, Di Gu Pi, Xian He Cao and/or Chun Gen Pi with any one or more of the three herbs, may be combined with any one or more, even all in certain embodiments, of an additional eleven herbs including Zi Cao, or radix *arnebiae* (arnebia root) or radix *lithospermi* (gromwell root), Xuan Shen, or radix *scrophulariae* (figwort root), Shi Gao or *gypsum fibrosum* (gypsum), Bai Shao, or radix *paeoniae alba* (white peony root), Chi Shao or radix *paeoniae rubra* (red peony root), Hong Hua or flos *carthami* (safflower), Da Qing Ye or *folium isatidis* (woad leaf), Qing Dai or *indigo naturalis* (natural indigo), Bai Zhu or *rhizoma atractylodis* macrocephalae (largehead atractylodes rhizome), and Shi Wei or folium pyrrosiae (shearer's pyrrosia leaf), Rou Gui or cortex *cinnamomi* (*cinnamomum* bark).

DA HUANG

Radix Et *Rhizoma Rhei* (Rhubarb)

CHEMISTRY

Da Huang contains free antraquinones, anthraquinone glycosides, and bianthrones. Among the free antraquinones contained within Da Huang are alizarin, aloe emodin, chrysophanol, citreorosein, emodin, laccaic acid D, physcion, and rhein. Among the anthraquinone glycosides contained within Da Huang are 1,8-dihydroxy-3-methylanthraquinone-1-O-β-D-glucoside (Palmatin), aloe emodin 1'-O-β-D-glucopyranoside, aloe emodin 1-O-β-D-glucopyranoside, chrysophanol 1-O-β-D-glucopyranoside (chrysophanein), chrysophanol 8-O-β-D-glucopyranoside, emodin 1-O-β-D-glucopyranoside, emodin 3-O-β-D-glucopyranoside (Glucoemodin), emodin 8-O-β-D-glucopyranoside, physcion 1-O-β-D-glucopyranoside, physcion 8-O-β-D-gentiobioside, physcionin, and rhein 1-O-β-D-glucopyranoside. Among the bianthrones contained in Da Huang are aloe emodin bianthrone, chrysophanol bianthrone, palmidins A-C, rheidins A-C, sennidins A, B and C and sennosides A-F.

Da Huang also includes other compounds including 2-(-2-hydroxy-propyl)-5-methyl-7-hydroxy-chromone, 2-(-2-hydroxypropyl)-methyl-7-hydroxy-chromanone, 2,5-dimethyl-7-hydroxychromone, 2-methyl-5-carboxymethyl-7-hydroxychromone, 3 napthalenes, 3,5,4'-trihydroxystilbene 4'-β-D-(2''-O-galloyl)-glucopyranoside, 3,5,4'-trihydroxystilbene 4'-O-β-D-(6''-O-galloyl)-glucopyranoside, 4'-O-methylpiceid, Rhapontin, Rheinosides A-D, Stilbene gakkates 3,5,4'-rtihydroxystilbene 4'-O-β-D-glucopyranoside, Stilbene piceid and Tannins.

PHARMACOLOGY

Purgative Effect of Da Huang

Da Huang is well known as a purgative agent. The active constituents are the combined anthraquinones, especially sennosides. The content of sennosides correlates with the purgative activity of rhubarb.

TABLE 1 illustrates the oral purgative $ED_{50}$ values of the anthraquinones

| Anthraquinones | $ED_{50}$ (mg/kg) | Anthraquinones | $ED_{50}$ (mg/kg) |
|---|---|---|---|
| Sennoside A | 13.5 | Aloe-emodin-8-glycoside | 71.6 |
| Sennoside B | 13.9 | Emodin monoglucoside | 103.6 |
| Sennoside C | 13.3 | Aloe-emodin | 59.6 |
| Sennoside D | 13.8 | Rhein | 97.5 |
| Sennoside E | 13.5 | Emodin | >500 |
| Sennoside F | 16.1 | Physcion | >500 |
| Rhein-8-glucoside | 20.0 | Chrydophanol | >500 |

Studies on the mechanisms of action found that sennosides act predominantly on the large intestine. The most potent purgative activity was obtained from the rhubarb extract or Sennoside A by gastrical administration and from sennidin by intravenous route Inhibition of the intestinal flora in mice with chloramphenicol significantly decreased the activity prosthetic sugar group of the anthraquinone glycosides prevented the anthrone from being oxidized before they are transported into the large intestine and hydrolysed by the bacterial enzyme into free sennidins. It was found that sennosides are hydrolysed by microbial β-glycosidase in a stepwise fashion to the corresponding sennidins via 8-monoglycosides. The resulting metabolites sennidins were further reduced, possibly by a reductase bound to cell membranes of intestinal bacteria, to rheinanthrone as the purgative principle.

Ligation of the junction of the large and small intestines failed to prevent anthraquinone glycoside producing a purgative effect in the large intestine. Oral administration of rhubarb started to produce effect 6-8 h later. These results suggest that there is also a large part of anthraquinone glycosides absorbed in the small intestine and transformed in the liver before they act on the pelvic plexus and produce peristalsis and purgation.

On the other hand, small doses (0.05-0.3 g by oral administration) rhubarb caused constipation because of its high content of tannins. The constipation effect can be prevented by decocting rhubarb together with Huang Lian (Rhizoma Coptidis). This is because the tannins and berberine, the main constituent of Huang Lian, form gelatinous precipitates during decoction.

Antimicrobial Effect of Da Huang

Tested by mixing virus with dilutions of aloe emodin for 15 min at 37° C., herpes simplex virus type 2 and type 3, varicella-zoster virus, pseudorabies virus, influenza virus were inactivated. Electron microscopic examination of the virus demonstrated that the envelopes were partially disrupted, indicating that it is directly virucidal to enveloped viruses. Emodin and rhein showed antiviral activity against human cytomegalovirus (HCMV) strain AD-169. When tested against a ganciclovir-resistant strain of HCMV, the $EC_{50}$ value for rhein was superior to the value obtained for the AD-169 strain. The aqueous extract of R. palmatum inhibited hepatitis B virus (HBV) polymerase activity and to bind hepatitis B virus surface antigen (HBsAg). Intravenous dose of 50 mg/kg of the extract to duck hepatitis B virus (DHBV) carrier ducklings showed antiviral activity against DHBV using serum DHBV DNA level and DHBV DNA polymerase activity as antiviral indicators.

Rhubarb exhibited inhibition against staphylococci, Streptococcus hemolyticus, Corynebacterium diphtheriae, Bacillus subtilis, B. brucellosis, B. mycoides, B. smegatis, Mycobacterium graminis, Yersenia pestis, Salmonella tophi, S. paratyphi, Shigella dysenteriae and Neisseria gonorrhea. Staphylococci and Neisseria gonorrhea were most sensitive to the herb. The main antibacterial components were the anthraquinone derivatives with the structure of 1,9-dihydroxyanthraquinone. 3-Carboxyrhein, hydroxyaloe-emodin and hydroxyemodin showed the most potent antibacterial activity. The bacteriostatic concentrations of rhein, emodin and aloe-emodin against staphylococci, streptomycin, Corynebacterium diphtheria, Bacillus subtilis, B. anthracis and Salmonella tophy were mitochondrial respiratory chain of microorganisms. Respiration of Staphylococcus aureus was strongly inhibited by emodin, aloe-emodin and rhein. Rhein, emodin and rhein specifically interfered with the redox function NADH dehydrogenase.

The aqueous, ethanolic and ether extracs of rhubarb are also antifungal against many pathogenic fungi, including Achorion schoenleini, Trichopphyton concentricum, T. violaceum, T. gypsum, Nocardia asteroids, Epidermophyton flocosum and Sporotrichum schenckii. The decoction of rhubarb exhibited inhibition against the influenza virus. The minimal effective dose in chicken embryo in vitro and semi in vivo was 5 mg per embryo.

Antineoplastic and Antimutagenic Effects of Da Huang

Intraperitoneal administration of 75 mg/kg of emodin produced a 45% inhibition against the mammary carcinoma of mice. The inhibition rates of 5 mg/kg of rhein and emodin against murine melanoma were 76% and 73%. Rhein, emodin and aloe-emodin inhibited murine leukemia $P_{388}$ in vivo, increasing the survival time and decreasing the ascites volume. They also inhibited Ehrlich ascites carcinoma, emodin was a strong inhibitor of respiration in Ehrlich ascites carcinoma cells, with an $ED_{50}$ of 20 μg/ml. Cellular respiration in leukemia $L_{1210}$ cells was also inhibited. Palmatin, Cysophanein and physcionin also exhibited moderate cytotoxic activity against several types of carcinoma cells.

The extract of the herb from R. palmatum and emodin induced a dose-dependent decrease in the mutagenicity of benzo(a)pyrene [B(a)P,], 2-amino-3-methylimidazo(4,5-f)

quinoline (IQ) and 3-amino-1-methyl-5H-pyrido(4,3-b)indole (trp-P-2) in *Salmonella typhimurium* TA98. It was further found that emodin reduced mutagencity of IQ by direct inhibition of the hepatic microsomal activation and not by interaction with proximate metabolites of IQ and/or by modification of DNA repair processes in the bacterial cell. Emodin also markedly decreased the mutagenicity of 1-nitropyrene (1-NP) in a dose dependant manner in Ames-microsomal test with *S. typhimurium* TA98 and the genotoxicity in SOS chromotest with *E. coli* PQ37. Furthermore, emodin significantly inhibited the formation of 1-NP DNA adducts in *S. typhimurium* TA98. The results suggest that emodin acts as a blocking and/or suppressing agent to reduce the direct-acting mutagenicity of 1-NP.

Hemostatic Effect of Da Huang

Rhubarb is also in TCM as a hemastatic agent. The hemastatic activity has been proved experimentally and clinically. Rhubarb is effective for both external and internal hemorrhage. It was effective in the treatment and prevention of experimental gastric bleeding and ulcer formation in rats. Significant therapeutic effects of the powdered rhizome of *R. palmatum* in the treatment of gastrointestinal bleeding were also reported. It reduces coagulation time and the permeability and fragility of capillaries. It increases fibrinogen and promotes bone marrow to produce platelets.

Immunosuppressive Effect of Da Huang

Emodin at $3 \times 10^{-7}$-$3 \times 10^{-4}$ M dose-dependently suppressed the responses of human mononuclear cells to phytohemagglutinin and mixed lymphocyte reaction. It was further found that after exposure to emodin ($10^{-6}$ M) the production of interleukin-1 (IL-1) and interleukin-2 (IL-2) and the expression of IL-2 receptor were all decreased, Emodin may be a new template for the development of better immunosuppressive agents for use against transplantation and autoimmune disease.

Choleretic Effect of Da Huang

Rhubarb can stimulate construction of the gallbladder and relax Oddi's sphinctercan, thus promoting bile secretion. It also increases the contents of bilirubin and bile acid.

Other Effects of Da Huang

Oral administration if emodin and rhein provoked marked diuretic, natriuretic and kaliuretic effects in rabbits. Oral administration of rhubarb increased urinary excretion of sodium and potassium, alkalizing urine to a pH value as high as 8.4. Rhubarb also inhibits the activities of pepsase, trypsase, pancreatic amylase and pancreatic lipase. It lowers blood pressure and blood cholesterol levels. Rabbits with fever induced by subcutaneous injection of the pneumococci responded with reduced temperature after oral administration of the decoction of rhubarb.

Intraperitoneal administration of 15 mg/kg of emodin exhibited antiinflammatory activity against carrageenin-induced pedal inflammation in rats. In the same dosage it also showed antiulcerative activity against pylorus-ligated, aspirin and immobilization stress-induced gastric ulcer in rats. It decreased acid and pepsin output and augmented mucus secretion in terms of total carbohydrate:protein ration in the gastric juice of aspirin treated pylorusligated rats, indicating that the antiulcerative effect of emodin may be due to this effect on gastric secretion.

MU DAN PI

Cortex Moutan (Paeony Bark)

CHEMISTRY

Mu Dan Pi contains Apiopaeonoside, Benzoyloxypaeoniflorin, Benzoylpaeoniflorin, Galloyloxypaeoniflorin, Galloypaeoniflorin, Mudanpiosides A-F, Oxypaeoniflorin, Paeconoside, Paeoniflorin, Paeonisuffral, Paeonisuffrone, Paeonol, Paeonolide, Pentagalloyglucose 1,2,3,4,6, and Suffruticosides A-E

PHARMACOLOGY

Antimicrobial Activity of Mu Dan Pi

The decoction of the root bark exhibited a strong antibacterial activity in vitro against the following bacteria: *Bacillus subtilis, Escherichia coli, Salmonella typhi, S. paratyphi, Protues vulgaris, Pseudomonas aeruginosa. Staphylococcus aureus, Strephtococcus hemolyticus, Diplococcus pneumoniae* and *Vibrio cholerae*. Paeonol was one of the antibacterial components; its MIC values were 1:2000 against *Staphylococcus aureus*, 1:1500 against *Bacillus subtilis* and *Escherichia coli*.

Anti-inflammatory Effect of Mu Dan Pi

The 70% methanolic extract of the root bark inhibited rat paw swelling induced by carrageenin. Paeonol was found active in inhibiting rat paw swelling induced by dextran, acetic acid or carrageenin. It also inhibited the increase of intra-abdominal capillary permeability of mice and cutaneous capillary permeability of guinea pigs caused by acetic acid or 5-HT. On the other hand, the water soluble fraction free from paeonol as well as the glycoside fraction also exhibited a significant inhibitory action on rat paw edema due to carrageenin. The water-soluble fraction was also effective in either preventing or treating adjuvant-induced arthritis in rats. The methanolic extract, the glycosidic fraction and paeonol inhibited blood platelet aggregation. ADP- or collagen-induced human plateet aggregation was inhibited by paeonol. The formation of thromboxan $B_2$ was also inhibited but the formation of 12-hydroxy-5,8,10,14-eocpsatetraenoic acid from C-arachidonate was stimulated. Besides, paeonol inhibited the formation of prostanoids such as prostaglandins and thromboxanes from C-arachidonate in rat peritoneal macrophages. Thus the anti-inflammatory action of the root bark was related to the inhibitory effects of paeonol on prostanoid synthesis.

Hypotensive Effect of Mu Dan Pi

The blood pressure of dogs with essential or renal hypertension was significantly reduced after oral administration of 5 g/kg of the decoction of the root bark for 5 days and 10 g/kg for two more days. The blood pressure of dogs with renal hypertension was also lowered after oral of 10 g/kg of the decoction free paeonol for 10 days. Oral administration of 0.5-1.0 g/kg of paeonol also produced hypotensive action renal hypertensive dogs and rats.

Effect on the CNS of Mu Dan Pi

Intraperitoneal or oral administration of paeonol decreased the spontaneous activity of mice, antagonized caffeine-induced hyperactivity and prolonged cyclobarital-induced sleep. At higher doses, paeonol caused disappearance of the righting reflex in mice. It also antagonized convulsions due to cardiazol, strychnine, nicotine and electric shock. Furthermore, paeonol was found to have antipyretic and analgesic activities. Paeonol decreased the body temperature of normal mice and the mice with typhoid and paratyphoid vaccine-induced fever. Oral administration of paeonol produced an analgesic effect against acetic acid-caused writhing and tail pain by pressing in mice.

Effect on Obesity of Mu Dan Pi

The aqueous extract of the herb was given as drinking water at the concentration of 0.5% to (SLN×$C_3$H/He) $F_1$ obese mice between 3 and 32 weeks of age. The treatment resulted in a significant decline, particularly in males, in food intake and in the Lee index, An index of obesity, and furthermore an increase in glucose tolerance. No significant difference was observed between the experimental and the control groups in the serum free fatty acid levels. There was little difference between groups in the weights of heart, liver, lung, spleen and major endocrine organs in both sexes and in the pattern of oestrous cycles in females, There results indicate that the herb protects against obesity, especially in males, at least partly by a decrease in food intake and an increase in glucose metabolism.

Other Effects of Mu Dan Pi

Paeonol exhibited anticholinergic and antihistaminic actions on isolated ileum of mice and guinea pigs. It also prevented stress ulcer in mice and inhibited gastric secretion in rats and spontaneous motility of rat uterus in situ. The extract of the root bark and paeonol were also of antimutagenic activity. They decreased the frequency of mutations induced by 4-nitroquinoline 1-oxide in *Escherichia coli* WP2s.

SHENG DI HUANG

Radix *Rehmanniae* (Chinese Foxglove Root)

CHEMISTRY

Sheng Di Huang contains 4-(α-L-rhamnopyranosyloxy)-3-methoxybenzoylajugol, Aceutoside, Ajugol, Aucubin, Campesterol, Castanosides A and F, Catalpol, digoxin Echinacoside, E-feruloylajugol, Isoacetoside, Jioglutoside A and B, Jionosides A&B, Leonuride, Mannitol, Melittoside, p-courmaroylagujol, p-hydorxybenzoylajugol, Purpureaside C, Rehmaglutins A, Rehmaionosides A-C, Rehmanniosides A-D, Rehmapicroside, Vanilloylajugol, Z-feruloylajugol, and β-sitosterol,

PHARMACOLOGY

Effects on Adrenocortical function and Cortisol Metabolism of Sheng Di Huang.

The herb was able to stop the decrease of plasma corticosterone concentration due to administration of dexamethasone and prevent the adrenal cortex from atrophy. The corticosterone level in rabbits receiving dexamethasone was increased at week 4 and week 6 when the herb was concurrently applied. No morphological changes were observed in the pituitary gland and adrenal cortex of rabbits receiving concurrent treatment of dexamethasone and the herb. A single large dose (3 g/kg) of the root or together with two other herbs Zhi Mu (*Rhizoma Anemarrhenae*) and Licorice (0.9 g/kg each) given orally antagonized the inhibitory effect of dexamethasone on the pituitary-adrenal system of rabbits, thereby increasing plasma corticosterone level.

This mixture also antagonized the inhibitory action of dexamethason on the early morning cortisol secretion peak in 12 normal subjects as tested in diurnal dexamethason suppression test. The crude extract (8 mg) of the root, when incubated with the liver sections of rabbits, protected cortisol from being reduced on the double bond between $C_4$ and $C_5$, and the ketone at $C_3$ and being degraded of the hydroxyl groups at $C_{17}$ and $C_{21}$, and the ketone at $C_{20}$, thus delaying the metabolism of cortisol in the liver. When the herb was used simultaneously with exogenous adrenocortical hormones, plasma cortisol could still be kept at a nearly normal level. The mechanism is believed to be a kind of competitive effect which influenced the binding of cortical hormone to the receptors and affected the uptake of corticosteroid hormone by the liver cells, thereby slowing down the catabolism of cortisol.

Cardiovascular and Diuretic Effects of Sheng Di Huang

The effects of the herb on the heart were largely dependent on doses. There was no obvious cordial activity at 0.1 or 0.5% concentration. At 1% concentration, cordial effect was observed in the isolated perfused frog heart. This action was more obvious in weak heart. When concentrations were increased to 2-5%, the heart was inhibited. Its effects on blood pressure was also dose-dependent. In an experiment with perfused vessels, 1-3% of the extract caused vasoconstriction while at 5% vasodilation.

Intravenous injection of 2.5 ml of the root extract produced a diuretic effect in anesthetized dogs. This action may be related to the cordial and renal vasodilation activities.

Effect on Blood Glucose of Sheng Di Huang

Results in animal experiments have been inconsistent on the effect of the herb on blood glucose. Hypoglycemic effects of alcoholic extract of the root at a subcutaneous dose of 2 g/kg or an oral dose of 4 g/kg in rabbits were reported by early researchers. The result obtained from the subcutaneous injection was more significant: the blood sugar was decreased to the lowest level 4 h after medication. Subcutaneous administration of the alcoholic extract to rabbits also inhibited the prolonged hyperglycemic effect elicited by carbohydrates from the root of *Codonopsis pilosula* (Dang Shen). Intramuscular administration of 20 g of the same extract also suppressed and prevented epinephrine-induced hyperglycemia in rabbits. Other studies, however, reported that the aqueous or alcoholic extract could only reduce the blood glucose of normal rabbits and was not effective in hyperglycemia due to epinephrine. But there were also reports that the herb had no effect on the normal blood glucose level of rabbits. The decoction or the ethanolic extract at 6 g/kg had no effect on the normal blood glucose measurements of rabbits within 6 h of medication. Subcutaneous administration of 20 g/kg of the same agents also failed to antagonize epinephrine-induced hyperglycemia in rats. More recently, a weak hypoglycemic activity of rehmannioside D in spontaneous diabetic mice was reported.

Antiinflammatory and Immunosuppressive Effects of Sheng Di Huang

Formaldehyde-induced edema of rat paws subsided after oral administration of the decoction or alcoholic extract at the daily dose of 10 g/kg for 5 days. However, another report claimed that only the decoction and not the alcoholic extract had a significant anti-inflammatory activity. At the oral dose of 100 mg/kg, jionoside B and acetoside produced 36% and 18% suppression of hemolytic plaque forming cells in the spleens of mice. In the same test conditions, intraperitoneal dose of 30 mg/kg of cyclophosphamide had a 52.5% suppression.

Hemostatic Effect of Sheng Di Huang

The coagulation time in rabbits was reduced after giving the yellow needle crystal obtained from the ethanolic extract of the root. Intraperitoneal administration of 10 g/kg of the decoction or ethanolic extract, or oral administration of the charred herb shortened the bleeding time in mice with tail wounds.

Effect on Hemorheology of Sheng Di Huang

The effects of the herb on the hemorheology of inflammatory, thromosic and intact animals were examined. Oral administration of 200 mg/kg of the 50% ethanolic extract of the herb inhibited the reduction of fibrinolytic activity erythrocyte deformability, the decrease in erythrocyte counts and the increase in connective tissue of the thoracic artery in a chronic inflammatory model, adjuvant-induced arthritis. However, it was ineffective on the development of edema in the arthritic rats and on acute and chronic inflammation. In addition, the extract inhibited the reduction of erythrocyte deformability but not the decrease of coagulative factors in a thrombosic model, endotoxin-induced disseminated intravascular coagulation (DIC). It also exhibited a promoting effect on erythrocyte deformability and fibrinolytic activity in intact rats. There results suggests that oral administration of the extract can prevent an inducement of impediment in the peripheral microcirculation of various chronic diseases through the improvement of hemorheology.

Other Effects of Sheng Di Huang

Antiradiation, antifungal and antihepatotoxic activities have also been observed with extract of the root in animals. The 100% injection solution of the root given intraperitoneally at 1 ml daily for 6 days mitigated platelet damage in rats caused by 600 rad of γ-irradiation. The aqueous extract of the root inhibited intro fungi mentagrophyton. *Microsporum gypseum* and *M. audouini*. The decoction of the root showed protective effect in mice against CCl-caused liver intoxication. Oral or intraperitoneal administration of 10 g/kg of the decoction or the alcoholic extract potentiated the hypnotic effect of pentobarbital sodium. Intraperitoneal dose of 20 g/kg of the decoction or the alcoholic extract protected mice from hypobaric hypoxia.

JIN YIN HUA

Flos *Lonicerae* (Honeysuckle Flower)

CHEMISTRY

Jin Yin Hua contains 2,6,6-trimethyl-2-vinyl-5-hydroxytetrahydropyran, Benzyl-alcohol, Carvacrol, Cis and trans-2-methyl-2-vinyl-5-(α-hydroxyisopropyl)-tetrahydrofuran, Epivogeloside, Eugenol, Geraniol, Hex-1-ene, Hex-3-en-1-ol, Isochlogogenic acid b+c (two isomers of 3,4-dicaffeoyl quinic acid), Isochlorogenic acid a (3,5-dicaffeoyl quinic acid), Linalool, Loganin, Lonicerin, Lonicerin, Luteolin, Methylcaffeate, Pinene, Saponins with oleanolic acid, Secologanin dimethylacetal, Secoxyloganin, sweroside, Vanillic acid, Venoterpin (gentialutine), Vogeloside, α-terpineol, and β-phenylethyl alcohol.

PHARMACOLOGY

Antimicrobial Activities of Jin Yin Hua

The extracts of both the flower and vine inhibited in vitro the following bacteria *Staphylococcus aureus, Streptococcus hemolyticus, Escherichia coli, Shigella dysenteriae, Vibrio cholera, Salmonella typhi, S. oaratyphi, Diplococcus pneumoniae, Neisseria meningitides, Pseudomonas aeruginosa* and *Mycobacterium tuberculosis*. It also potentiated the action of penicillin against the drug-resistant *Staphylococcus aureus*. Chlorogenic acid and isochlorogenic acid are believed to be the chief antibacterial components of the flower. Luteolin also showed an antibacterial activity. More than half of the mice receiving the LD dose of *Pseudomonas aeruginosa* or its endotoxin survived after given 7.5 g/kg of the injection solution of the flower by intraperitoneal administration. Intravenous administration of 6 g/kg of the distillate of the flower was also therapeutically effective in rabbits poisoned by the endotoxin of *Pseudomonas aeruginosa*.

Antifunal activity was observed with the aqueous extract of the flower against *Microsporum ferrugineum* and *Nocardia* asteroids. In the monolayer primary culture of the epithelial cells of human embryonic kidney, the decoction of the flower inhibited influenza virus, ECHO virus and herpes virus.

Anti-inflammatory Effect of Jin Yin Hua

Intraperitoneal administration of 0.25 g/kg of the flower inhibited carrageenin-induced paw edema in rats. Given twice a day at 8 g/kg for 6 days by Intraperitoneal injection, the extract of the flower showed antiexudative and antihyperplastic effects on croton oil-induced granuloma. Intraperitoneal administration of the injection solution increased the phagocytic activity of the inflammatory cells in mice. The decoction diluted to 1:1280 concentration was still able to promote leukocytic phagocytosis.

Central Stimulant Effect of Jin Yin Hua

Oral administration of chlorogenic acid produced central stimulation in mice and rats in experiments using electric shock and revolving cage; the potency of the central stimulation was ⅙ that of caffeine. No addictive or synergistic action was observed when they were used together.

Antilipemic Effect of Jin Yin Hua

Oral administration of 2.5 g/kg of the flower reduced the intestinal absorption of cholesterol and the plasma cholesterol level. In vitro experiments showed that the flower conjugated with cholesterol.

Other Effects of Jin Yin Hua

Intraperitoneal administration of an aqueous-ethanolic extract of the flower of *L. japonica* to mice on day 8 after mating decreased pregnancy in the test animals dose-dependently. Intrauterine and intra-amniotic administration of the extract killed the fetuses in dogs and caused abortion in monkeys, respectively. The extract of the flower exhibited a mild prophylactic effect against experimental gastric ulcer in rats when given orally. Large oral doses of chlorogenic acid increased gastrointestinal peristalsis and promoted gastric and bile secretion. Chlorogenic acid had a stimulant effect on the isolated rat uterus.

DI GU PI

Cortex Lycii Radicis (Wolfberry Bark)

CHEMISTRY

Di Gu Pi contains 5α-stigmastan-3 6-dione, Betaine, Cinnamic acid, Kukoamine A, Linoleic acid, Lyciumamide, Melissic acid, Sugiol, and β-sitosterol

PHARMACOLOGY

Antipyretic Effect of Di Gu Pi

The aqueous or alcoholic extract of the herb, given orally or by injection, produced a significant antipyretic effect in rabbits with fever induced by pyrogen. Betaine was also active. A strong antipyretic effect was also exhibited by the aqueous fraction of the alcoholic extract at doses ranging from 0.75 to 7.5 g/kg equivalent of the crude drug. The precipitates of the extract from lead salt also showed comparable antipyretic activity to synthetic antipyretic analgesics.

Hypoglycemic Effect of Di Gu Pi

Oral administration of the decoction of the herb decreased blood glucose level in rabbits by 14% in average; this action lasted for 7-8 h. The peak action was observed 3 to 4 h after administration. It was also less effective when give subcutaneously. Subcutaneous dose of 6 g/kg of the extract elicited a mean reduction of 14% of the blood glucose of rabbits after 1 h.

Hypotensive and Anticholesterolemic Effect of Di Gu Pi

The decoction, macerate, tincture and injection solution of the herb produced a significant hypotensive effect in anesthetized dogs, cats, rabbits by intravenous or intramuscular administration and in anaesthetized rats by oral administration. Repeated intravenous administration at lower doses did not induce rapid tolerance. Intravenous injection of 0.375 g/kg of the injection solution resulted in sudden drop of blood pressure and death of anesthetized dogs. Bradycardia, prolongation of PR interval and depressed T wave in the ECG were observed. Kukoamine A induced hypotension in rats when given intravenously at a dose of 5 mg/kg.

Daily oral administration of 10 g/kg of the extract of the herb for 3 weeks decreased the serum cholesterol in rabbits by 36.9% with little effect on triglyceride.

Antimicrobial Activity of Di Gu Pi

In the sensitivity test using the paper disc method, the decoction of the herb strongly inhibited Bacillus typhosus, Salmonella paratyphi A, and Shigella flexneri but was inactive against Staphylococcus aureus. It was a weak bacteriostatic against Mycobacterium tuberculosis. In the primary monolayer tissue culture of the embryonic renal cells, the decoction prevented the pathogenic changes in the cells due to Asian influenza virus A JK strain.

Effect on the Uterus of Di Gu Pi

The 100% injection solution of the bark showed stimulation effects on normal rat uterus and isolated mouse uterus. The activity of 1 ml of the solution was comparable to that of 0.054 unit of pituitrin.

XIAN HE CAO

Herba Agrimoniae (Hairyvein Agrimonia Herb)

CHEMISTRY

Xian He Cao contains Agrimols A, B, C, D and E, Agrimoniin, Agrimonolide, Agrimorphol, Apigenin-7-glucoside, Caffeic acid, Ellagic acid, Gallic acid, Luteolin-7-glucoside, Pendinculagin, Potentillin, and Quercetin

PHARMACOLOGY

Teniacidal Effect of Xian He Cao

The winter sprout of the herb is used in folk medicine to expel tenia and the active principle was found to be agrimophol. Agrimophol acts directly on the parasite. It inhibits the glycogenolysis, aerobic and anaerobic metabolism in the parasite.

The herb and agrimophol are also lethal to some other parasites, such as Trichomonas vaginalis, blood fluke and roundworm.

Antibacterial Activities of Xian He Cao

Six compounds, luteolin-7-glucoside, apigenin-7glucoside. Quercetin, ellagic acid, caffeic acid and gallic acid, isolated from the herb were active against bacillary dysentery. Combination use of luteolin-7-glucoside and ellagic acid, apigenin-7-glucoside and apigenin-7-glucoside was more effective than the respective individual compounds.

Antitumor Effect of Xian He Cao

Agrimoniin had antitumour activity when given as a pre- or posttreatment. A single dose of 10-30 mg/kg prolonged the life span of mice bearing $MM_2$ tumors or yielded cures when given intravenously or orally prior to or after tumor inoculation. Agrimoniin also inhibited the growth of MH-134 and Meth-A solid tumors in mice. It was strongly cytotoxic to $MM_2$ cells in vitro, but the activity was almost completely abolished by the addition of fetal calf serum to the culture. Intraperitoneal administration of agrimoniin increased the number of peripheral white blood cells and the proportion of monocytes. The antitumor activity of agrimoniin appeared to be due to its enhancement of the immune response.

Cardiovascular Effect of Xian He Cao

Intravenous administration of the alcoholic extract of the herb increased blood pressure and stimulated respiration in anesthetized rabbits and dogs, but the alcohol-soluble fraction of the aqueous extract lowered blood pressure in rabbits. Perfused into the blood vessels of rabbit ear and frog hind limb, it caused vasoconstriction at low concentrations and vasodilation at high concentrations. The extract and agrimoniin increased the heart rate and cardiac contractility of frogs and toads. On the other hand, the alcohol-soluble fraction of the aqueous extract inhibited the isolated frog heart.

CHUN GEN PI

Cortex Ailanthi (Tree-of-heaven Bark)

CHEMISTRY

Chun Gen Pi contains 1-(1',2'-dihydroxyethyl)-4-methoxy-β-caboline, 1-(2'-hydroxyethyl)-4-methoxy-β-carboline, 1-(2-hydroxy-1-methoxy)-ethyl-4-methoxy-β-carboline, 13(21)-dehydro-glaucarubinone, 13(21)-dehydroglaucarubolone, 1-acetyl-4-methoxy-β-carboline, 1-carbamoyl-β-carboline, 1-carbomethoxy-β-carboine, 1-hydroxycanthin-6-one, 1-methoxycanthin-6-one, 1-methoxy-canthin-6-one-3-oxide, 5-hydroxymethylcanthin-6-one, 6-methoxy-β-carboline-1-carboxylic methyl ester, Ailanthone, Ailantinols A and B, Amarolide, Amarolide 11-acetate, Canthin-6-one, Canthin-6-one-3-oxide, Chaparrinone, Chaparrolide, Glaucarubinone Quassinoids $\Delta^{13\ (18)}$-dehydro-glaucarubinone, $\Delta^{13\ (18)}$-dehydroglaucarubolone, Shinjudilactone, Shinjulactones A-N, and β-carboline-1-propionic acid.

PHARMACOLOGY

Glaucarubinone and ailanthone showed amebicidal activity in vitro against the parasite *Entamoeba histolytica*. Some quassinoids markedly inhibited the growth of chloroquine-resistant *Plamodium falciparum*. Glaucarubinone produced complete inhibition at 0.0006 μg/ml. Ailanthone also showed potent antiulcer activity.

Figure 15:
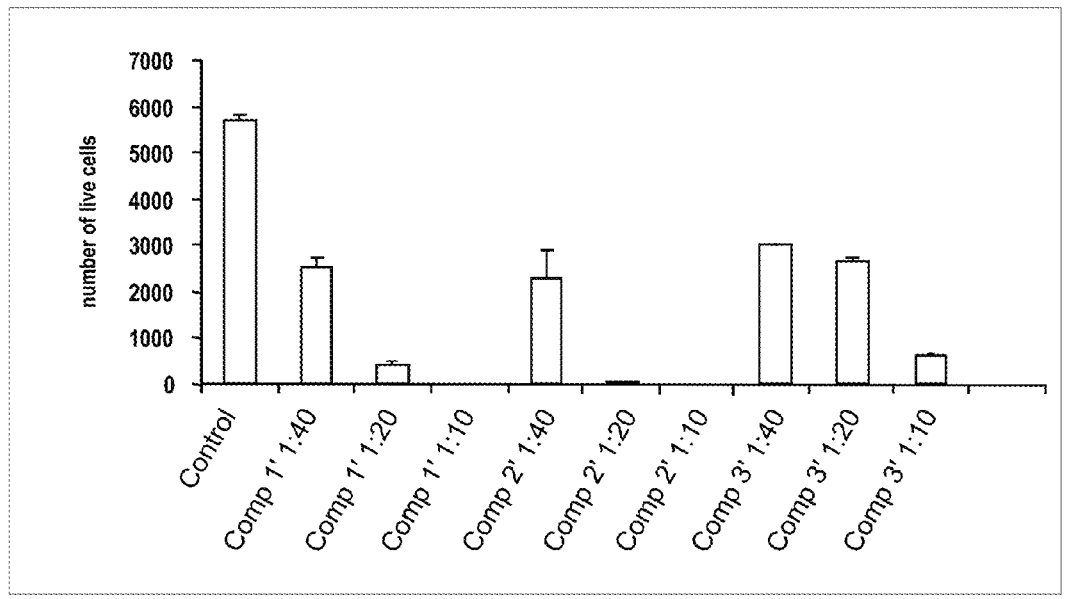
FIG. 15 is a bar chart that illustrates the effects of certain herbs and combinations of herbs on live cancer cells, including (C1) Sheng Di Huang—Rhemannia; as well as (C2) the combination of Jin Yin Hua—Lonicerae, Da Huang—Rhei, Mu Dan Pi—Moutan, and Di Gu Pi—Cortex Lycii, and (C3) the combination of Xian He Cao—Agrimoniae and Chun Gen PI—Ailanthi.

FIG. 15 illustrates the effect on live cells of three combinations of herbs each in three concentrations 1:40, 1:20 and 1:10. C1 includes Sheng Di Huang, C2 includes Jin Yin Hua, Da Huang, Mu Dan Pi and Di Gu Pi, and C3 includes Xian He Cao and Chun Gen Pi. FIG. 15 illustrates that each of these three example combinations provides a reduction of the live cell numbers particularly in higher concentrations, while C1 and C2 appear to be more effective than C3. Each of C1 and C2 includes one or two of the three herbs Sheng Di Huang, Jin Yin Hua and Da Huang, while C3 does not. In addition, the combination of four herbs in C2 appears to be more effective than the single herb in C1.

Figure 16:
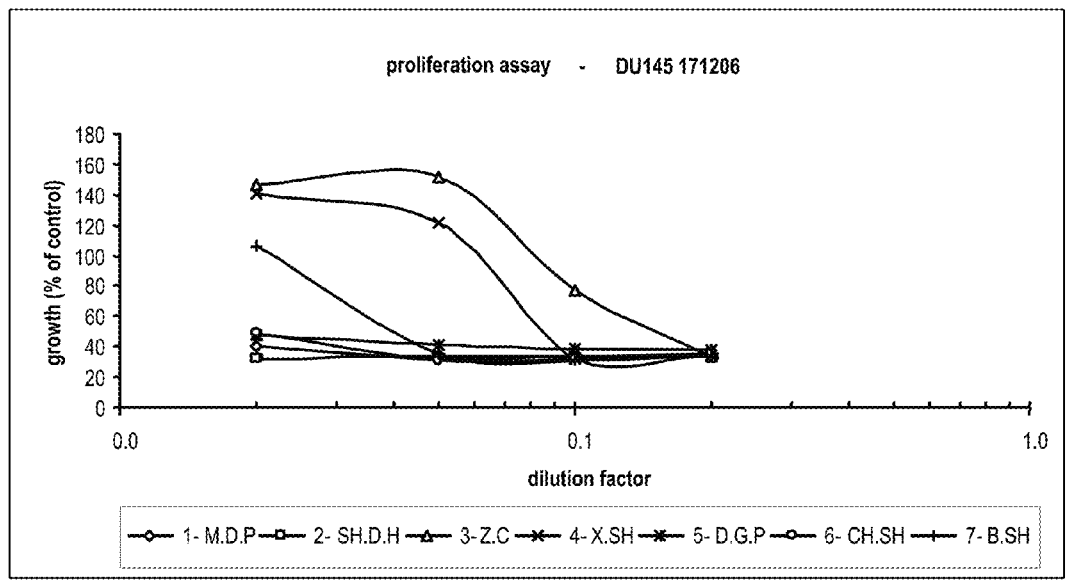
FIGS. 16-18 show plots of growth of cancer cells versus dilution factor for each of 18 different herbs.
Figure 17:
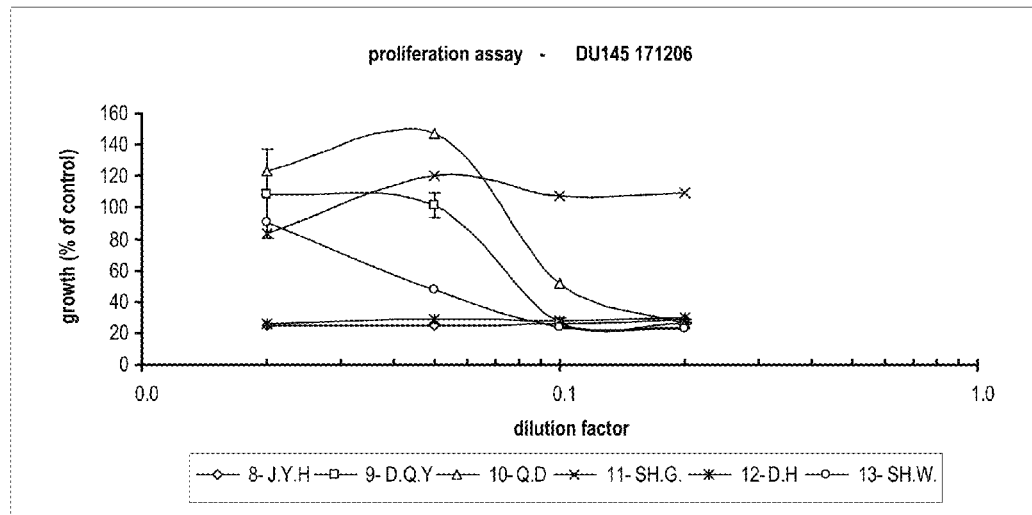
Figure 18:
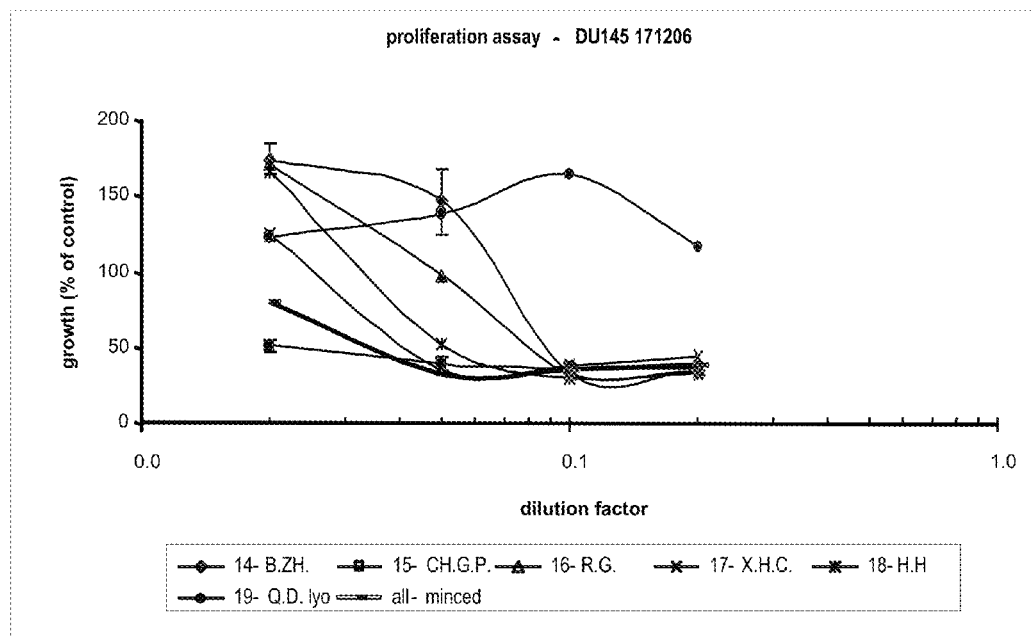

FIGS. 16-18 illustrate plots for each of the eighteen herbs of growth as a percentage of control versus dilution factor. FIGS. 16-18 illustrate that the three herbs Sheng Di Huang, Da Huang and Jin Yin Hua are most effective, while the four herbs Mu Dan Pi, Di Gu Pi, Xian He Cao and Chun Gen Pi are effective, and the eleven herbs Zi Cao, Xuan Shen, Shi Gao, Bai Shao, Chi Shao, Hong Hua, Da Qing Ye, Qing Dai, Bai Zhu, Shi Wei and Rou Gui are somewhat less effective.

Figure 19:
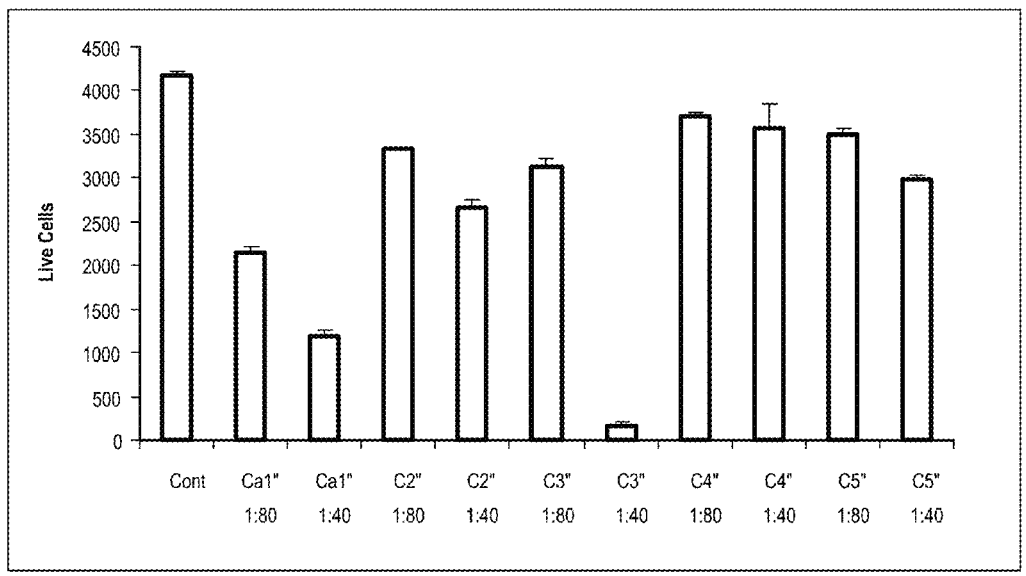
FIG. 19 is a bar chart that illustrates the effects of certain herbs and combinations of herbs on live cancer cells.

FIG. 19 illustrates the effect on live cells of five combinations of herbs each in two concentrations 1:40 and 1:80. Ca1 includes a combination of all eighteen herbs, C2 includes a combination of Jin Yin Hua, Da Huang, Mu Dan Pi and Di Gu Pi, C3 includes a combination of Da Huang, Sheng Di Huang and Jin Yin Hua, C4 and C5 include combinations of the other eleven herbs (Zi Cao, Xuan Shen, Shi Gao, Bai Shao, Chi Shao, Hong Hua, Da Qing Ye, Qing Dai, Bai Zhu, Shi Wei and Rou Gui) of the eighteen herbs, i.e., not in combination with any of the seven herbs (Sheng Di Huang, Da Huang, Jin Yin Hua, Mu Dan Pi, Di Gu Pi, Xian He Cao and Chun Gen Pi). Specifically, C4 includes Shi Gao, Shi Wei, Bai Zhu, Rou Gui, Hong Hua and C5 includes Zi Cao, Xuan Shen, Chi Shao, Bai Shao, Da Qin Ye, and Qing Dai. FIG. 19 illustrates that combinations of all eighteen herbs, as well as combinations of the three herbs (Sheng Di Huang, Da Huang and Jin Yin Hua) are most effective, while the combination C2 was less effective, and the combinations C4 and C5 were still less effective.

HERBAL INGREDIENTS

Aloe Emodin

Aloe emodin has a molecular weight around 270.24 g/mol. As to its anti-cancer activity, aloe emodin exhibits cytotoxicity in SCC of tongue, cervix cancer cells; and apoptoticity through MAPK-JNK cascade in hepatoma cells. Aloe emodin also tends to induce P53 and apoptosis. In addition, the cytotoxicity of aloe emodin induces effects in melanoma, and gastric carcinoma. As to its anti-inflammatory activity, aloe emodin exhibits anti TNF and anti virality in enveloped viruses-HSV, PSV, VSV, and INF. Aloe emodin also decreases COX2 and INOS expression in inflammation, and increases IFN in JEV and EV71. Aloe emodin may also be ingested for its properties as a laxative. Use of aloe emodin can induce nausia, and intestinal contraction causing abdominal pain. Long use of anthraquinones can lead to kidney and liver damage. The half-life of aloe emodin is about 78 min.

Chrysophanol

Chrysophanol has a molecular weight around 254.24 g/mol. As to its anti-cancer activity, chrysophanol exhibits necrosis in hepatic cancer cells, including ATP change and ROS cascade. Chrysophanic acid inhibits EGFR in colon cancer cells. As to its anti-inflammatory activity, chrysophanol can serve as an antiseptic, bactericide, candidicide, and/or cathartic. In addition, chrysophanol can be used as an anti-staph aurus and an anti-bacilus subtilis. Chrysophanol can be used to suppress the activation of NF-kB. and caspase-1 in LPS-stimulated macrophages. Chrysophanol is also an anti polio virus compound. Chrysophanol an be used as a hemostat and as a pesticide, and can be used in the treatment of menorrhagia, including bleeding following abortion, epistaxis, functional uterine bleeding and thrombocytopenia. Chrysophanol acts as a purgative, and can be used to converts aloe emodin through P450 in the liver. Emodin and chrysophanol may be ingested in combination as an anti cancer treatment agent. Chrysophanol has a half life of about 2.75 hours.

Emodin

Also known as *Rheum emodi*, emodin has a molecular weight around 270.24 g/mol. As to its anti-cancer activities, emodin exhibits pro apoptoticity in prostate cancer cells through P53, and P21. Emodin increases ROS, and improves chemotherapy effect in prostate cells which are drug resistant. Emodin exhibits pro apoptoticity through inhibition of IL6 in myltiple myaloma. Emodin exhibits anti-matastaticity0 through integrins effect. Emodin decreases HER2 in breast cancer and improves chemotherapoitic effect. Emodin induces cytotoxis in tongue carcinoma, and inhibits NFkB and other pro inflammatory cytokines. As to its anti-inflammatory activities, emodin may be used as an anti ulcer agent through Hpylori destruction and change in gastric fluid. Emodin induces a stabilizing effect on atherosclerotic plaque in vessels, and improves insulin and glucose changes in type 2 diabetes. Emodin promotes anti plasmodium against malaria, and may be used as an immunosuppressive, pesticide, purgative, spasmolytic, styptic, vasoelaxant, and/or viricide. Emodin has a half-life of approximately 227 min and converts to two active metabolites through P450 in the liver.

Rhein

Also know as cassic acid, Rhein has a molecular weight around 284.22 g/mol. As to its anti-cancer activity, rhein acts as an anti proliferative in hepatic carcinoma, breast cancer, SCC of lungs, and cervical cancer. Rhein improves taxol effect in breast cancer, and inhibits nasopharengeal carcinoma and EGFR. Rhein serves as a sinergist with mitomycin. Rhein exhibits cytotoxicity in tongue carcinoma. Rhein may be used for anti angiogenesis. As to its anti-inflammatory activity, rhein exhibits anti fibroticity, and promotes anti proliferation of hepatic cells through inhibition of TGFb1. Rhein may be used as an anti oxidant. Rhein decreases IL1B, and IL18 proinflammatory cytokines Rhein is also anti bacterial, and may be used against staph. Aunts. Rhein also increases sensitivity to ADH (drug). Rhein has a half-life of about 205 min (approx). Rhein is hydrophobic, and may be combined with lysin in order to be hydrophilic, as rhein lysinate.

Chrysophanein

Chrysophanein Exhibits Significant In-Vitro Cytotoxic Activity in Cancer Cell Lines Rhapontin Rhapontin has a molecular weight of around 420.41 g/mol. As to its anti-cancer activities, rhapontin induces apoptosis and suppresses KATO III cell-growth in stomach cancer. Rhapontin also provides protective effects on LDL and erythrocytes against oxidative damage. Rhapontin has a half life of about 23.5 minutes.

Stilbene Piceid

Stilbene piceid has a molecular weight around 390.2 g/mol. As to its anti-cancer activities, stilbene piceid inhibits DNA synthesis in LLC cells. Stilbene piceid also has an inhibitory effect on lipoxygenase. Stilbene also exhibits antioxidant activity and inhibits alpha-glucosidase. Stilbene piceid also inhibits lipid peroxidation induced by ADP and NADPH in liver microsomes. Stilbene acts directly on smooth muscle to promote pulmonary artery relaxation.

Tannin

Tannin has a molecular weight around 500-3000 g/mol. As to its anti-cancer activity, tannin suppresses the growth of MCF-7 breast cancer cells. Geraniin, a form of tannin separated from geranium, causes cell death through induction of apoptosis. Tannin exhibits different antiproliferative effects against cervical and colon cancer cells grown in vitro. In pomegranate, tannin modulates inflammatory cell signaling in colon cancer cells. Tannin promotes apoptosis through induction of p53 non-small cell lung cancer cells. As to its anti-inflammatory activity, tannin in tomato suppresses COX-2 expression. Tannin can be used as an in vitro antioxidant and/or antiplatelet and also as an anti-inflammatory due to its free radical scavenging effects. Tannin may be used for its antiviral, antibacterial and/or antiparasitic effects. Tannin can be used in the treatment of HFE hereditary hemochromatosis. Tannin is capable of reversing 6-hydroxydopamine induced toxicity. Tannin has a dental use, as well, as tannin-fluoride preparation reduces gingival inflammation around abutment teeth. A large intake of tannins may cause bowel irritation, kidney irritation, liver damage, irritation of the stomach and/or gastrointestinal pain. A correlation has been made between esophogeal or nasal cancer in humans and regular consumption of certain herbs with high tannin concentrations. Tannins inhibit the absorption of minerals such as iron which may, if prolonged, lead to anemia. Tannins are present in soil, plants, water, tea, wine, and fruit. Tannin has a half life of about 3.15 hours.

Carvacrol

Carvacrol, also known as cymophenol, has a molecular weight around 150.217 g/mol. As to its anti-cancer activities, carvacrol promotes anti-tumor effects on human metastatic breast cancer cells, including MDA-MB 231. Carvacrol is a potent inhibitor of cell growth in Human Non-Small Cell Lung cancer. Carvacrol also inhibits growth of myoblast cells even after activation of mutated N-ras oncogene. As to its anti-inflammatory activities, carvacrol activates PPAR and suppresses COX-2 inflammation. Carvacrol may be used for its antiproliferative and antiplatelet properties. Carvacrol is present in the essential oil of *Origanum vulgare*, oil of thyme, oil obtained from pepperwort, and wild bergamot. Carvacrol inhibits the growth of several bacteria strains, e.g. *Escherichia coli* and *Bacillus cereus*, and in *pseudomonas aeruginosa*, carvacrol disrupts the bacteria membrane. Carvacrol may be used for its antioxidant activity. Carvacrol has a half life of about 1.29 hours.

Eugenol

Eugenol has a molecular weight of about 164.2 g/mol. Eugenol induces apoptosis in human colon cancer cells, and inhibits invasion and angiogenesis of gastric carcinogenesis induced by MNNG. Eugenol in honey significantly inhibits the growth of Ehrlich ascites carcinoma. Eugenol-related biphenyl (S)-6,6'-dibromo-dehydrodieugenol elicits specific antiproliferative activity on neuroectodermal tumour cells partially triggering apoptosis. Eugenol causes melanoma growth suppression through inhibition of E2F1 transcriptional activity. Eugenol may also be used as an antiseptic. Eugenol also inhibits platelet aggregation induced by agonists, including collagen, ADP and calcium ionophore. Eugenol may be extracted from certain essential oils especially from clove oil, nutmeg, cinnamon, basil and bay leaf. Eugenol is also used in perfumeries, flavorings, essential oils and in medicine as a local antiseptic and anesthetic. Eugenol may be used for its antioxidative properties. Eugenol exhibits hepatotoxicity. An overdose of eugenol may induce convulsions, diarrhea, nausea, unconsciousness, dizziness, and/or rapid heartbeat. Eugenol can be allergenic. Eugenol may express carcinogenicity through oxidative DNA damage by its metabolite. Eugenol has a half-life of 1.975 hours, and under certain conditions, may have a half life up to 4 hours or even 18 hours.

Geraniol

Geraniol has a molecular weight of about 154.25 g/mol. As to its anti-cancer activities, Geraniol promotes an anti-proliferative mechanism in human pancreatic adenocarcinoma cells. Geraniol also promotes anti-proliferative and cell cycle regulatory effects in human breast cancer cells. Geraniol can cause a 2-fold reduction of thymidylate synthase and thymidine kinase expression in colon cancer cells. Geraniol, as a component of plant essential oils, sensitizes human colon cancer cells to 5-fluorouracil treatment. Geraniol suppresses pancreatic tumor growth without significantly affecting blood cholesterol levels. As to its anti-inflammatory activities, Geraniol diminishes the levels of inflammatory markers induced by pamidronate stimuli in vitro and in vivo. Geraniol also promotes inhibitory effects on nitric oxide and prostaglandin $E_2$ production in macrophages. Geraniol is a component of rose oil, palmarosa oil, and citronella oil, and small quantities of geraniol are in geranium and lemon, has a rose-like odor and is commonly used in perfumes. Geraniol can be used as effective plant-based mosquito repellent. Geraniol is found in cigarettes. As to biologic use, ion-exchange iontophoresis combined with geraniol is a highly effective transdermal delivery system. Geraniol suppresses Candida cell growth in the vagina and its local inflammation when combined with vaginal washing. Gernaiol is also allergenic. Geraniol has a half life of about 0.713 hours.

Luteolin

Luteolin has a molecular weight of 286.24 g/mol. As to its anti-cancer activity, luteolin, particularly in combination with standard anticancer drugs such as cisplatin, serves as a HDAC inhibitor, e.g., for the treatment of lung cancer. Luteolin promotes synergistic/additive growth inhibitory effects and may be effective in chemoprevention treatment of head and neck and lung cancers. Luteolin induces G1 arrest in human nasopharyngeal carcinoma cells. Luteolin not only protects DNA from oxidative damage, but also increases repair activity in Caco-2 cells. A low concentration of Luteolin has little toxic effect on cancer cells, but such low concentrations can sensitize chemotherapeutic drugs in various cancer cell lines. Luteolin selectively inhibits chymotrypsin-like and trypsin-like proteasome catalytic activities in tumor cells. Luteolin inhibits invasion of prostate cancer PC3 cells through E-cadherin.

Luteolin is a PDE4 inhibitor and a general phosphodiesterase inhibitor, and an Interleukin 6 inhibitor. Luteolin inhibits inflammatory response and improves insulin sensitivity in the endothelium. Luteolin prevents LPS-induced TNF-α expression in cardiac myocytes through inhibiting NF-κB signaling pathway. Luteolin inhibits myelin basic protein-induced human mast cell activation and mast cell-dependent stimulation of Jurkat T cells. Luteolin inhibits cyclooxygenase-2 expression and scavenges reactive oxygen species.

Luteolin is found in leaves, but it is also seen in celery, thyme, dandelion, rinds, barks, clover blossom and ragweed pollen. Luteolin is useful in the prevention and treatment of skin photoaging. Luteolin inhibits microglia and alters hippocampal-dependent spatial working memory. Luteolin enhances insulin sensitivity via activation of PPARγ transcriptional activity in adipocytes. Luteolin can induce nausea, vomiting and gastric hypersecretion. Luteolin has a half life of about 1.2 hours.

Saponins

As to the anti-cancer activities of saponins with oleanolic acid, achyranthoside H methyl ester, a novel oleanolic acid saponin derivative from Achyranthes fauriei roots, induces apoptosis in human breast cancer MCF-7 and MDA-MB-453 cells via a caspase activation pathway. Saponion with oleanolic acid exhibit insecticidal activity against the Mexican bean beetle larvae (Epilachna varivestis).

Vanillic Acid

Vanillic acid has a molecular weight of 168.14672 g/mol. Vanillic acid suppresses metastatic potential of human cancer cells through PI3K inhibition and decreases angiogenesis in vivo. Vanillic acid enhances the activity of human lymphocyte proliferation and secretion of IFN-gamma. Vanillic acid has a beneficial effect on DSS-induced ulcerative colitis, thereby manifesting its usefulness in the regulation of chronic intestinal inflammation. Phenolic compounds in mushroom Lentinula edodes (shiitake) are hepatoprotective through their suppression of immune-mediated liver inflammation. Vanillic acid is found in the root of Angelica sinensis, and in olive oil. Vanillic acid promotes reduced cellular tyrosinase activity, DOPA oxidase and melanin contents, as well as down-regulated expressions of melanocortin-1 receptor (MC1R), microphthalmia-associated transcription factor (MITF), tyrosinase, and tyrosinase-related proteins 2 (TRP-2) and TRP-1. Vanillic acid contributes to the prevention of the development of diabetic neuropathy by blocking the methylglyoxal-mediated intracellular glycation system. There exist an oxidized form of vanillin. Vanillic acis has a half life of about 10.552 hours.

α-Terpineol

The anti-cancer activities of α-terpineol, or alpha-terpineol, are partly mediated through the suppression of NF-kappaB activation. α-terpineol exhibits antiproliferative effects on erythroleukemic K562 cells. α-terpineol inhibits gene expression of the IL-6 receptor. α-terpineol suppresses fMLP-, LPS- and PMA-stimulated superoxide production. α-terpineol is found in cajuput oil, pine oil, and petitgrain oil, and is a common ingredient in perfumes, cosmetics, and flavors and tea. α-terpineol demonstrates different degrees of growth inhibition against 15 different genera of oral bacteria. α-terpineol can cause postural hypotension in pine oil, and can cause eye irritation. There are three isomers, alpha-, beta-, and gamma-terpineol. Alpha-terpineol has a half life of about 1.245 hours.

Aucubin

Aucubin has a Molecular Weight of 346.32978 g/Mol

1. Antiproliferative activity is through cell cycle arrest and apoptosis in human non-small cell lung cancer A549 cells.
2. research-DNA damage induced by topoisomerase I poisoning as one of the possible mechanisms by whichaucubin have shown antitumoral activity.
3. research-cytotoxic activity against MCF7-breast adenocarcinoma, HeLa-cervix adenocarcinoma, A431-skin carcinoma of epithelial origin. 4. can obstruct H(2)O(2)- induced apoptosis by regulating of the expression of Bcl-2 and Bax, as well as suppression of caspases cascade activation.

Aucubin enhance the activity of human lymphocyte proliferation and secretion of IFN-gamma. Aucubin is found in the leaves of *Aucuba japonica* (Cornaceae), *Eucommia ulmoides* (Eucommiaceae), and *Plantago asiatic* (Plantaginaceae). Aucubin protects against liver damage induced by carbon tetrachloride or alpha-amanitin, particularly when dosed intra-peritoneally. Aucubin provides neuroprotection in primary diabetic encephalopathy. Aucubin treatment can lower blood glucose. Aucubin can produce an increase in the level of lipid peroxidation and a decrease in activities of antioxidant enzymes in liver and kidneys. Aucubin has a half life of about 42.5 minutes.

Digoxin

Digoxin, also known as digitalis, has a molecular weight of 780.938 g/mol. Digoxin treatment can inhibit HIF-1alpha synthesis and block tumor growth. Digoxin induces apoptosis in a human acute T-cell lymphoblastic leukemia cell line. Digoxin can serve as a specific neuroblastoma growth inhibitor and an unspecific inhibitor of angiogenesis.

Digoxin is widely used in the treatment of various heart conditions, namely atrial fibrillation, atrial flutter and sometimes heart failure that generally cannot be controlled by other medication. Digoxin increases myocardial contractility, such that the heart rate is decreased, while blood pressure increases as stroke volume is increased, leading to increased tissue perfusion. Digoxin improves myocardial efficiency due to improved hemodynamics, and improves the ventricular function curve. Digoxin affects the kidney by increased renal blood flow and increased GFR. A mild diuretic effect is seen typically only in heart failure. Digoxin may cause AV junctional rhythm and ectopic beats (bigeminy) resulting in ventricular tachycardia and fibrillation.

Digoxin can induce loss of appetite, nausea, vomiting and diarrhea as the gastrointestinal motility increases. Other common effects of Digoxin are blurred vision, visual disturbances (yellow-green halos and problems with color perception), confusion, drowsiness, dizziness, insomnia, nightmares, agitation, and depression, as well as a higher acute sense of sensual activities. Less frequent adverse effects of digoxin (0.1%-1%) include: acute psychosis, delirium, amnesia, convulsions, shortened QRS complex, atrial or ventricular extrasystoles, paroxysmal atrial tachycardia with AV block, ventricular tachycardia or fibrillation, and heart block. Dangerous interactions can occur between digoxin and verapamil, amiodarone, erythromycin, and epinephrine. The efficacy of chemotherapeutic agent substrates of Pgp may be strongly reduced in patients taking digoxin. Digoxin treatment increases the risk of invasive breast cancer among postmenopausal women. Digoxin has a half-life around 36 hours.

Isoacetoside

Isoacetoside, as an extract from *Tecoma stans*, exhibits a cytotoxic effect on human hepatocarcinoma cells (Hep-G2). Isoacetoside has a half life of about 3.7-6.4 hours.

β-Sitosterol

β-sitosterol, or beta-sitosterol, has a molecular weight around 414.71 g/mol. β-sitosterol may be used to treat prostatic carcinoma and breast cancer. β-sitosterol may have chemopreventive potential by virtue of its radical quenching ability in vitro, with minimal toxicity to normal cells. β-sitosterol also attenuates beta-catenin and PCNA expression, making it a potential anticancer drug for colon carcinogenesis. β-sitosterol significantly inhibits the growth, and induces the apoptosis, of SGC-7901 human stomach cancer cells in vitro. The decrease of the bcl-2/bax ratio and DNA damage may produce apoptosis induced by beta-sitosterol in SGC-7901 human stomach cancer cells. β-sitosterol enhances tamoxifen effectiveness on breast cancer cells by affecting ceramide metabolism. β-sitosterol has a proapoptotic effect that is mediated through the activation of ERK and the block of the PI3K/Akt signal pathway in MCA-102 cells. Therefore, beta-sitosterol has a strong potential as a therapeutic agent for preventing cancers such as fibrosarcoma. Beta-sitosterol is an effective apoptosis-promoting agent and that incorporation of more phytosterols in the diet may serve a preventive measure for breast cancer. An anti-microtubule characteristic of beta-sitosterol may contribute to the proliferation inhibition of SiHa cells in cervical cancer. β-sitosterol activates the sphingomyelin cycle and induces apoptosis in LNCaP human prostate cancer cells. β-sitosterol promotes anti-asthmatic actions that may be mediated by inhibiting the cellular responses and subsequent release/synthesis of Th2 cytokines β-sitosterol may have therapeutic potential in allergic asthma.

β-sitosterol is found in *Nigella sativa*, pecans, *Serenoa repens* (saw palmetto), avocados, *Curcurbita pepo* (pumpkin seed), *Pygeum africanum*, cashew fruit, rice bran, wheat germ, corn oils, soybeans, sea-buckthorn, wolfberries, and *Wrightia tinctoria*.

β-sitosterol reduces blood levels of cholesterol, and is sometimes used in treating hypercholesterolemia. β-sitosterol may produce a positive effect on male hair loss in combination with Saw palmetto. β-sitosterol may play a major role in herbal therapy, especially in the treatment of benign prostatic hyperplasia. Beta-sitosterol is a naturally occurring phytosterol that may be used to cure atherosclerosis, diabetes, cancer, and inflammation and is also an antioxidant. β-sitosterol has a half life of about 0.966 hours By taking more than the recommended dose of β-sitosterol, people may suffer from stomach upset, nausea, diarrhea, gas or constipation, impotence (also known as erectile dysfunction or ED), decreased sex drive. Beta-Sitosterol should be avoided during pregnancy and breast-feeding, since it is not proven to be benign with regard to potential effects on unborn and newborn children. β-Sitosterol is also not recommended for individuals with sitosterolemia, a rare inherited fat storage disease, because people with this condition have too much β-sitosterol and related fats in their system, taking β-sitosterol will only worsen this condition. High levels of β-sitosterol concentrations in blood have been correlated with increased severity of heart disease in men having previously suffered from heart attacks, and may cause allergy.

Half lives have been indicated for certain molecules. The half lives of molecules can vary from these, e.g. generally based on the herb growing and/or preparation conditions, how it is combined with other herbs of molecules in treatment, or based on patient characteristics and behaviors such as eating and drinking and physical activity, or on potency or other factors. Doses and dose periods may be determined based in part on the half lives. Typically, however, doses and dose periods will be determined based on characteristics of the patient, the patient's condition and the patient's history, as well as on the expertise and experience of the attending physician.

The treatment method may include periodic doses including one or more of the herbs described herein in combination with approximately 5 ug/ml or 10 ug/ml or more of emodin, alone or in combination with respectively 0.05 ug/ml or 0.10 ug/ml or more of digoxin. Other combinations may be used in the treatment, including combining 5 ug/ml or more of emodin alone or with at least approximately 0.10 ug/ml digoxin, or at least approximately 10 ug/ml emodin alone or with at least approximately 0.10 ug/ml digoxin, or more than 5 ug/ml of emodin alone or with at least approximately 0.05 ug/ml digoxin, or at least approximately 10 ug/ml emodin alone or with at least approximately 0.05 ug/ml digoxin. Other combinations may be used and prescribed by physicians depending on factors such variances in weight, age, gender, family or patient history, or other characteristics specific to patients.

The treatment regimen may include once or twice daily doses, or two or more weekly doses weekly or otherwise. Doses may be taken more than once or twice a day, while the amounts of each dose would be determined according to the periodicity of the treatments.

Methods of preparing leukemia or other cancer treatment medicines are also provided, including preparing a cocktail including a combination of emodin and/or digoxin alone or in combination with one or more of the herbs described herein.

A leukemia or other cancer treatment medicine is also provided, including a cocktail including a combination of emodin and/or digoxin alone or in combination with one or more of the herbs described herein.

Certain embodiments are directed to novel therapeutic applications of cardiac glycosides such as digoxin and quabain alone or in combination with emodin and its analogs for the treatment of cancer, and more specifically, blood cancers. Unexpectedly, these embodiments disclose that digoxin synergizes with emodin to stimulate cancer cell death, and that emodin or digoxin, or both, synergize with certain herbs to stimulate cancer cell death.

FIG. 1 illustrates the effect of proliferation of digoxin, emodin, and their combination on NB4 leukemic cells. The results represent average of triplicates±STDEV. The percentage of life and death cells was done using staining for PI for death cells and the number of lived cells was determined by FACS.

Figure 2:
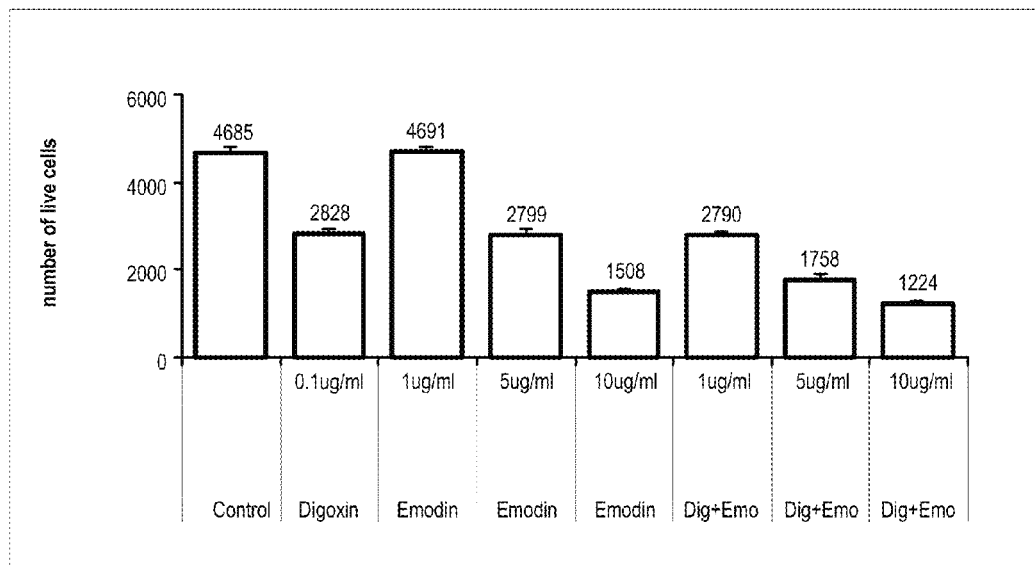
FIG. 2 illustrates the effect of on proliferation of digoxin, emodin, and their combination on HL-60 leukemic cells.

FIG. 2 illustrates the effect of proliferation of digoxin, Emodin, and their combination on HL-60 leukemic cells. The results represent average of triplicates±STDEV. The percentage of life and death cells was done using staining for PI for death cells and the number of lived cells was determined by FACS.

Figure 3:
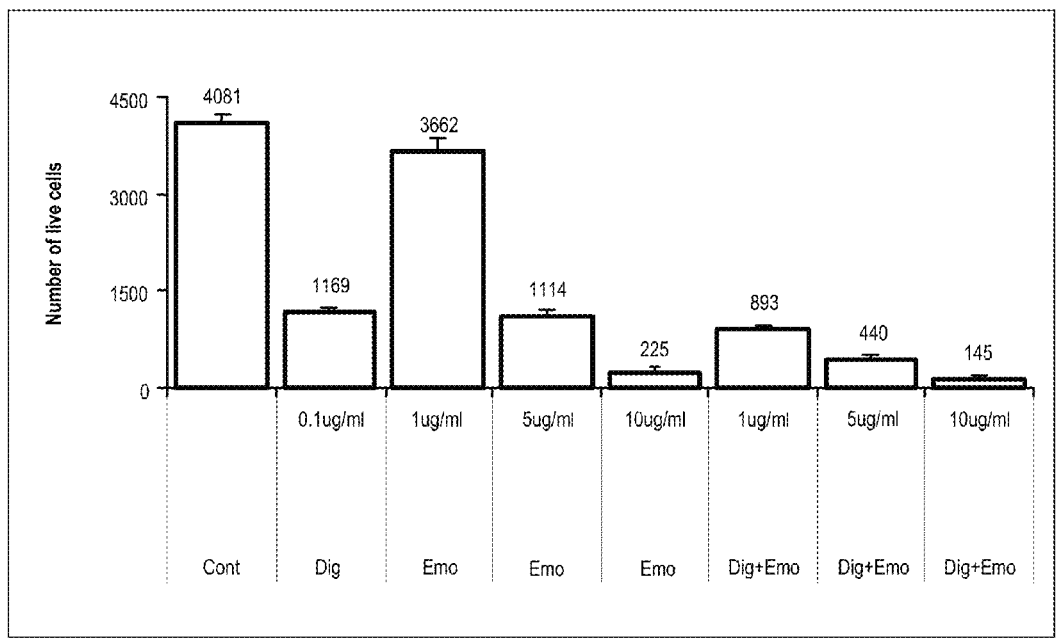
FIG. 3 illustrates the effect of on proliferation of digoxin, emodin, and their combination on Jurkat T cell leukemic cells.

FIG. 3 illustrates the effect of proliferation of digoxin, emodin, and their combination on Jurkat T cell leukemic cells. The results represent average of triplicates±STDEV. The percentage of life and death cells was done using staining for PI for death cells and the number of lived cells was determined by FACS.

Figure 4:
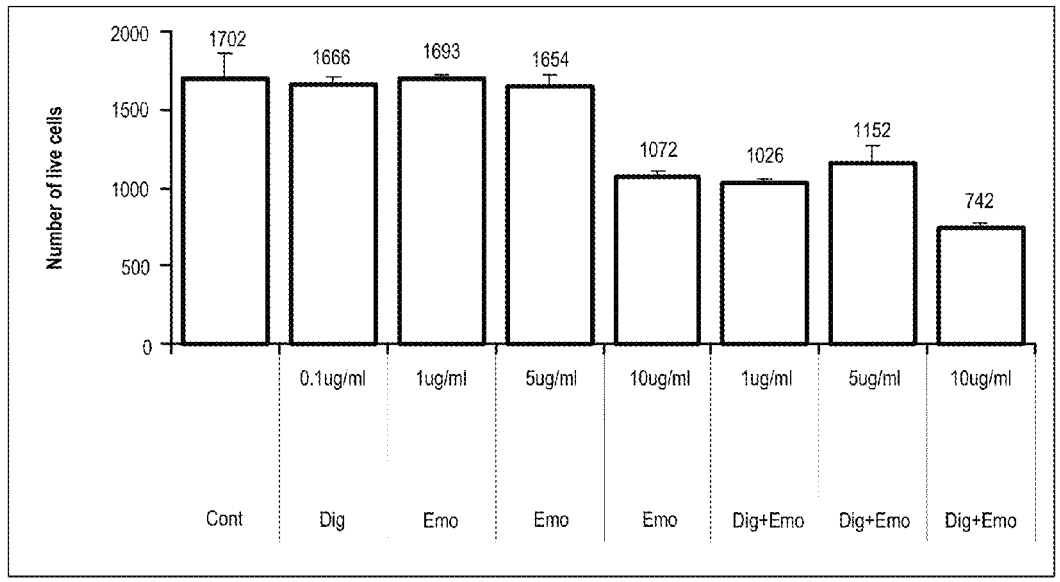
FIG. 4 illustrates the effect of on proliferation of digoxin, emodin, and their combination on HT29 colon cancer cells.

FIG. 4 illustrates the effect of proliferation of digoxin, emodin, and their combination on HT29 colon cancer cells. The results represent average of triplicates±STDEV. The percentage of life and death cells was done using staining for PI for death cells and the number of lived cells was determined by FACS.

Figure 5:
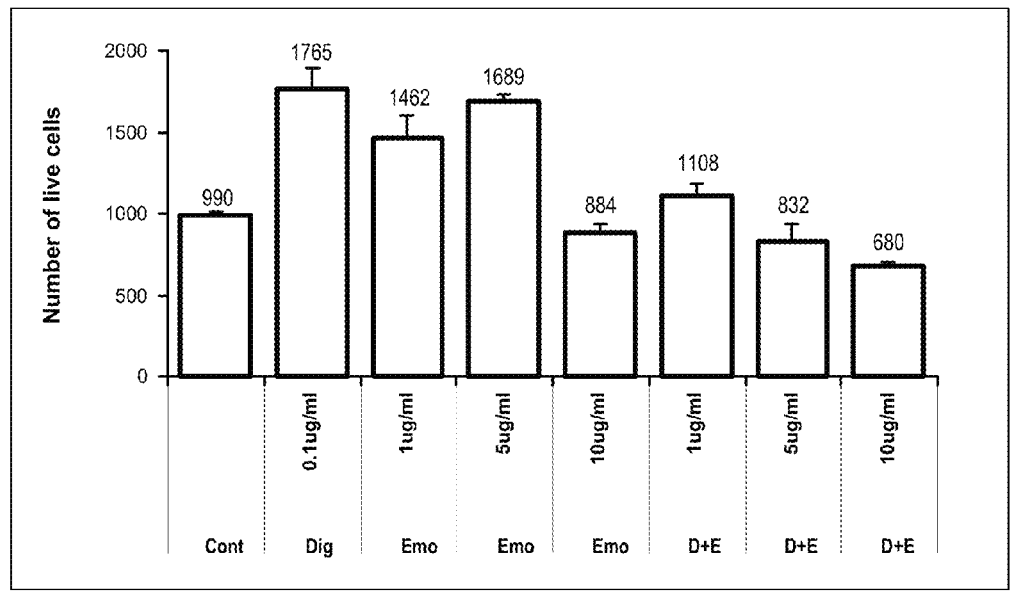
FIG. 5 illustrates the effect of proliferation of digoxin, emodin, and their combination on PC3 prostate tumor cells.

FIG. 5 illustrates the effect of proliferation of digoxin, emodin, and their combination on PC3 prostate tumor cells. The results represent average of triplicates±STDEV. The percentage of life and death cells was done using staining for PI for death cells and the number of lived cells was determined by FACS.

Figure 6:
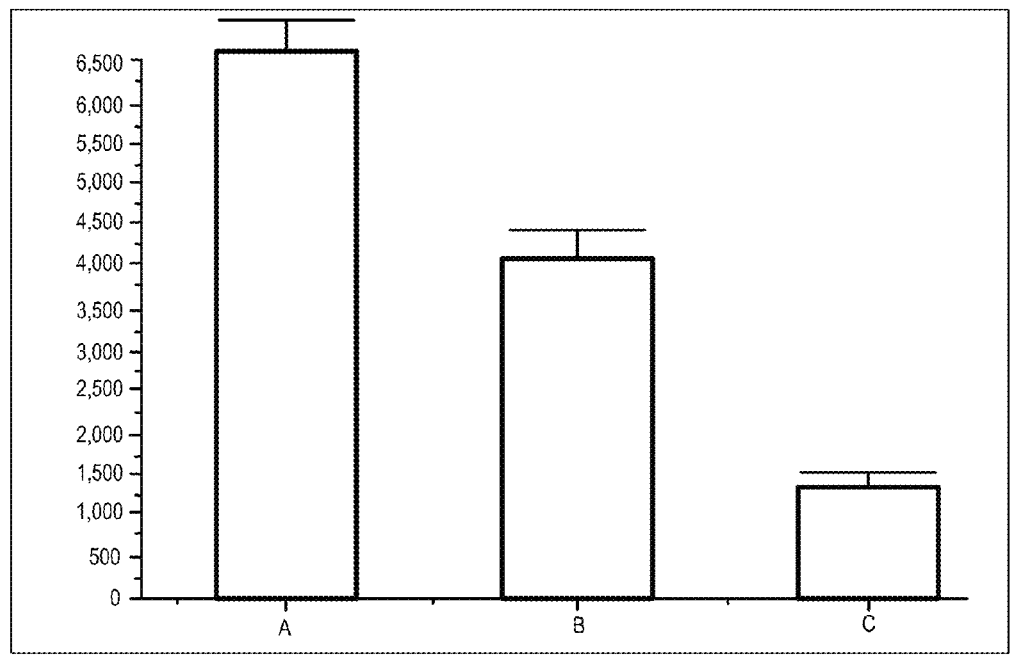
FIG. 6 illustrates the effect of proliferation of Digoxin, emodin and their combination on MDA 435 Breast Cancer cells.

FIG. 6 illustrates the effect of proliferation of digoxin, emodin and their combination on MDA 435 are cell line of Breast Cancer. In the in vitro experiments, there is a dependency on concentration.

Figure 7:
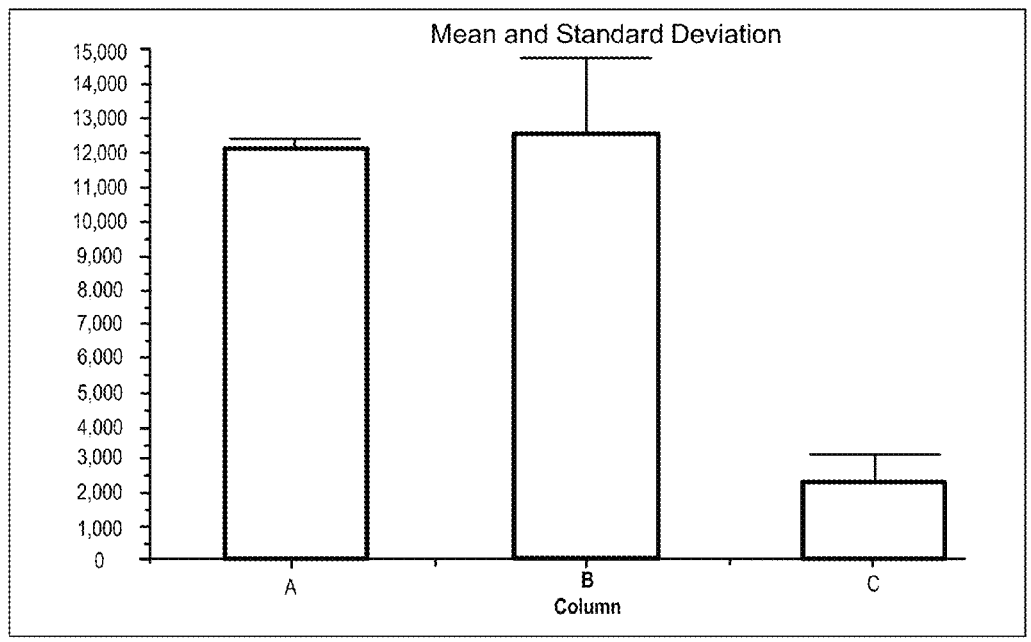
FIG. 7 illustrates the effect of proliferation of Digoxin, emodin and their combination on MDA 435 cell lines of Melanoma and Breast Cancer.

FIG. 7 illustrates the effect of proliferation of digoxin, emodin and their combination on MDA 435 are cell lines of Melanoma and Breast Cancer. In this case, concentration of 1/100 had no effect (same as Control) 1/3 had good effect and 1/10 killed all cells. Normal cells were affected 50-90% less than the rate of pathological cells. Treatments described herein may be prepared for topical use for treatment of melanoma, BCC (basal cyr carcinoma) and inflammatory skin diseases like Psoriasis. For example, combinations of herbs and/or herbal extracts as described herein may be prepared as a cream to apply onto the skin. Herb or herb extract combinations described herein also may be injected to to infected areas of the skin of a patient using a syringe. An example method for preparation of an external cream in accordance with certain embodiments is provided below.

PREPARATION OF EXTERNAL CREAM/OINTMENT

First, two of more of the herbs are cooked, for example, as described elsewhere herein or as may be understood or determined by those skilled in the art. A cream is then prepared that may be somewhat more of less than half herbs and half cream, e.g., a 30% liquid of herbs in 1:1 ratio and 70% cream may be used. The herbs can also be prepared as a tincture, e.g., soaking the herbs in alcohol for a period of time such as 2 weeks in a ratio of 1:3, for example. This herbal liquid can then be mixed with the cream in the same way as described above.

Treatments described herein may also be effective against immunodeficiency diseases such as HIV and AIDS, as well as other conditions affecting the immune system.

Figure 8:
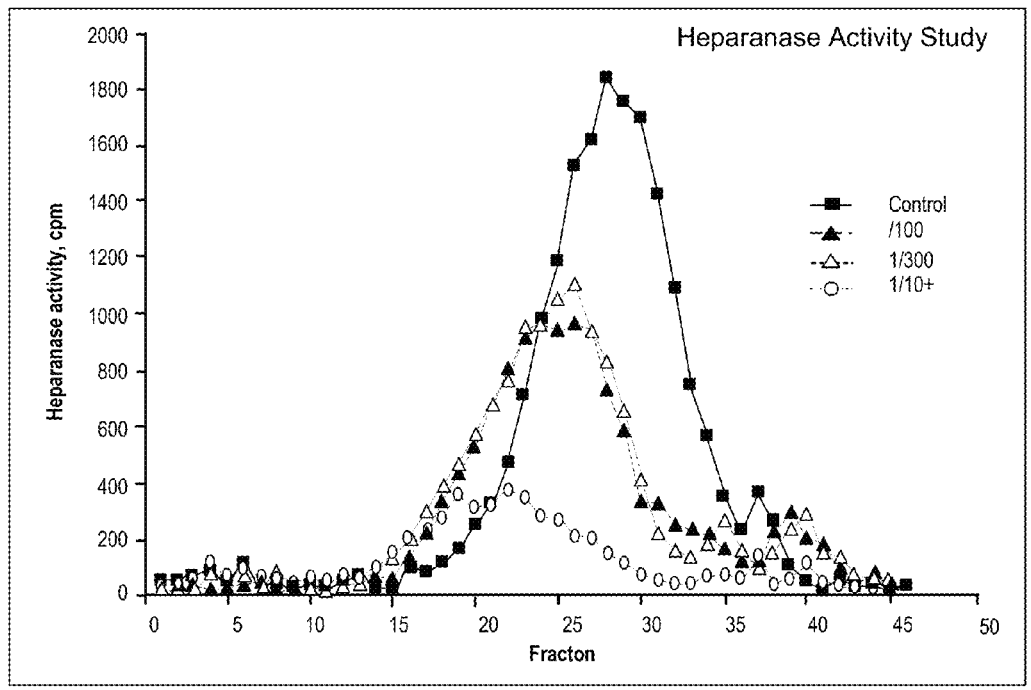
FIG. 8 illustrates the effect of proliferation of Digoxin, emodin and their combination on Heparanase activity.

FIG. 8 illustrates the effect of proliferation of digoxin, emodin and their combination on Heparanase activity. Heparanase is an enzyme that relates to angiogenesis (the physiological process involving the growth of new blood vessels from pre-existing vessels). This slide depicts the fact that the proliferation of the combination of digoxin and emodin delays the activity of this enzyme.

Figure 9:
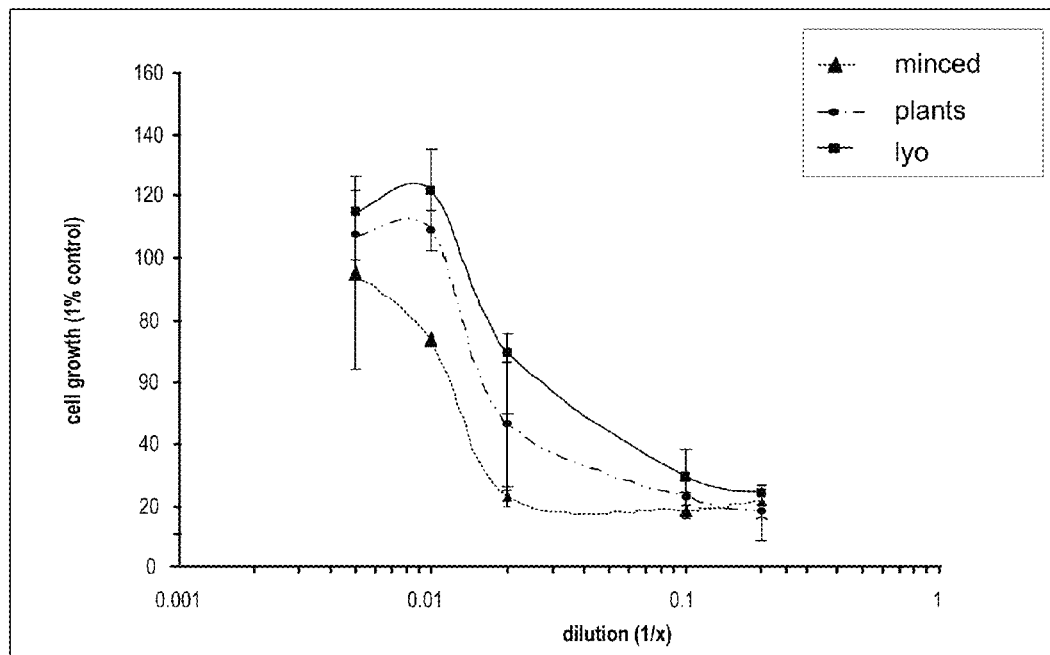
FIG. 9 illustrates the effect of proliferation of Digoxin, emodin and their combination on HMVEC activity.

FIG. 9 illustrates the effect of proliferation of digoxin, emodin and their combination on HMVEC which is also an enzyme that is related to angiogenesis.

Figure 10:
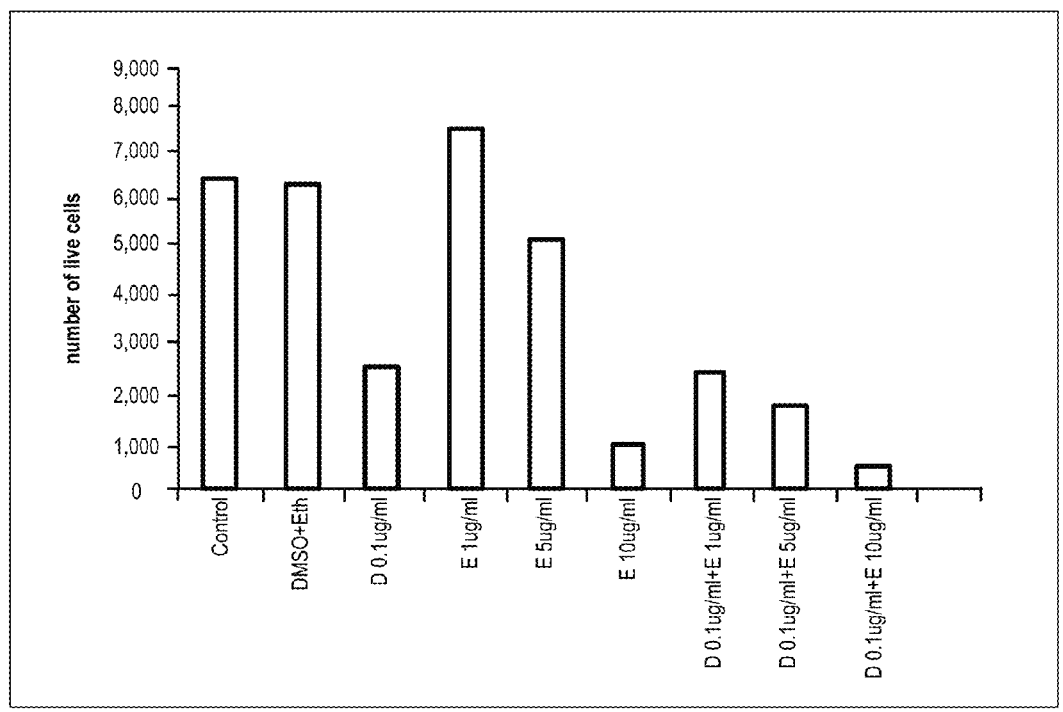
FIGS. 10-11 illustrates the effect of proliferation of Digoxin, emodin and their combination on NB-4 Cell Line for AML (Acute Milo Leukemia).
Figure 11:
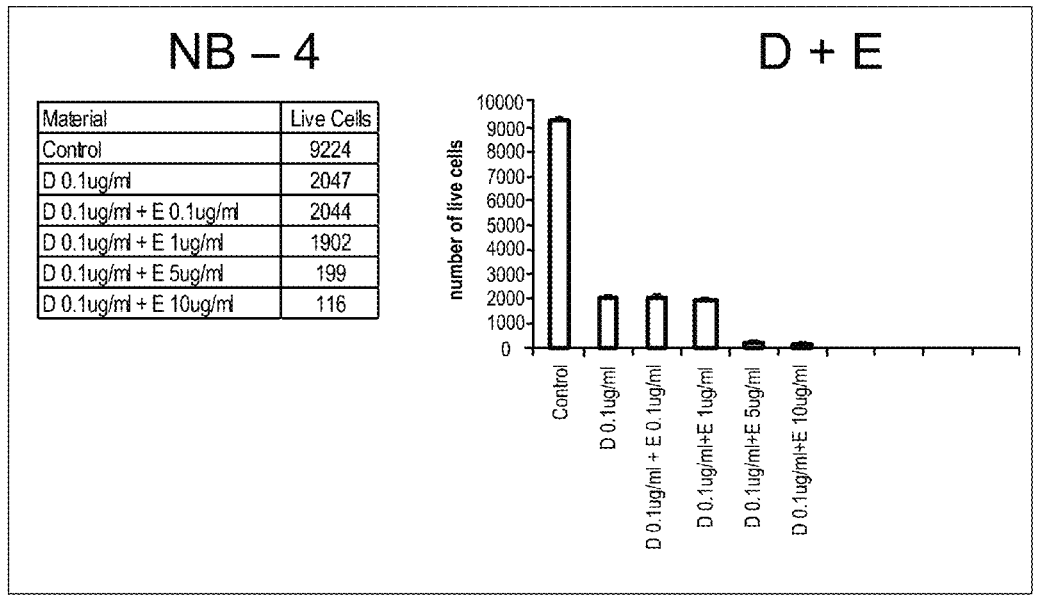

FIGS. 10 and 11 illustrate the effect of proliferation of digoxin, emodin and their combination on NB-4 is Cell Line for AML (Acute Milo Leukemia). The two left bars in the diagram of FIG. 10 are Control (DMSO as well). The Digoxin alone 0.1 ug/ml (illustrated by the 3rd bar) shows a strong effect. Emodin alone has an effect only in large concentration (approximately 10 ug/ml or more). The three bars to the right in FIG. 10 are the effect of the combination of Digoxin and emodin. Taking Digoxin 0.1 ug/ml and Emodin 10 ug/ml has a very strong effect better than either of the two acting alone. In fact, the effect is more than double with 892 live cells measured when emodin alone is used, and 892 when Digoxin alone is used, and 371 were measured when both Digoxin and emodin were used in combination. This surprising effect of the combination of Digoxin and emodin shows an advantageous feature of the present invention.

Figure 12:
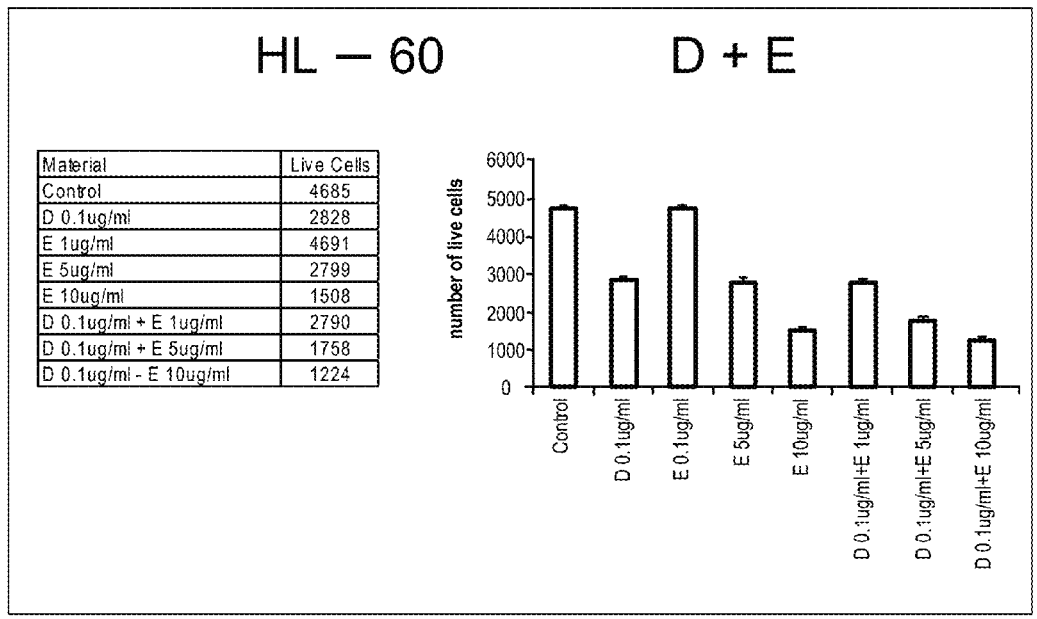
FIG. 12 illustrates the effect of proliferation of Digoxin, emodin and their combination on HL-60 Cell Line.
Figure 13:
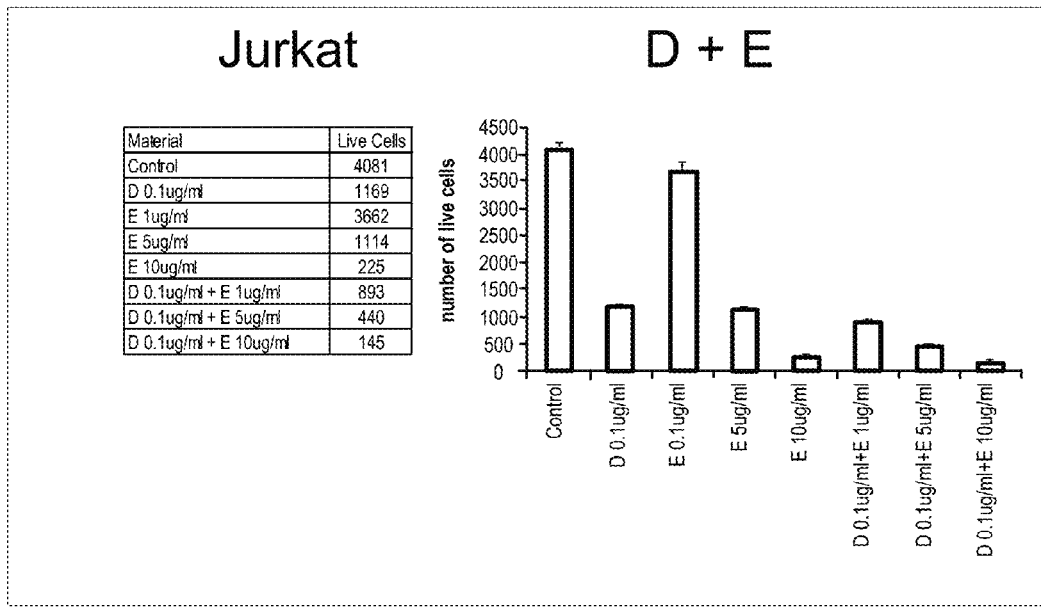
FIG. 13 illustrates the effect of proliferation of Digoxin, emodin and their combination on Jurkat cell line.

FIGS. 12-13 show that for HL-60, which is Promyolitic Leukemia, as well as for Jurkat, which is Acute T cell Leukemia, the same surprisingly advantageous synergistic effect was observed.

Figure 14:
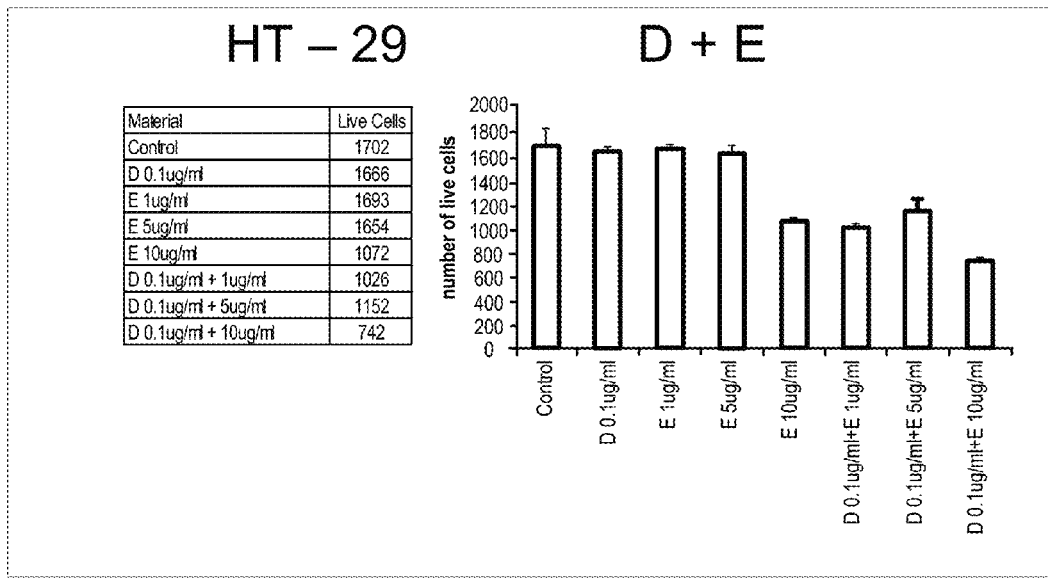
FIG. 14 illustrates the effect of proliferation of Digoxin, emodin and their combination on HT-29 cell line.

FIG. 14 also shows a synergistic advantage of using the combination of Digoxin and emodin on the HT-29 cell line.

EXAMPLES

The embodiments of the present invention are directed to advantageous medicines and methods of treatment and preparation of medicines and treatments for cancer wherein combinations of emodin or digoxin, or both, alone or in combination with certain herbs such as Da Huang and Sheng Di Huang, and/or Jin Yin Hua, and/or Mu Dan Pi, Di Gu Pi, Xian He Cao and/or Chun Gen Pi, and/or any one or more of the eleven additional herbs including Zi Cao, or radix *arnebiae* (arnebia root) or radix lithospermi (gromwell root), Xuan Shen, or radix *scrophulariae* (figwort root), Shi Gao or *gypsum fibrosum* (gypsum), Bai Shao, or radix *paeoniae alba* (white peony root), Chi Shao or radix *paeoniae rubra* (red peony root), Hong Hua or flos *carthami* (safflower), Da Qing Ye or folium *isatidis* (woad leaf), Qing Dai or *indigo naturalis* (natural indigo), Bai Zhu or *rhizoma atractylodis macrocephalae* (largehead atractylodes rhizome), Shi Wei or folium *pyrrosiae* (shearer's pyrrosia leaf), and/or Rou Gui or cortex *cinnamomi* (*cinnamomum* bark), and/or combinations of certain herbal ingredients, such as digoxin "D" and/or emodin "E," and/or one or more others described above including Emodin, Rhein, and/or Rhapontin of Da Huang, Carvacrol, Vanillic acid, and/or Sitosterol of Jin Yin Hua, and/or Aucubin, Digoxin, and/or beta-sitosterol of Sheng Di Huang and/or other ingredients present within the two, the three, the seven and/or even the eighteen herbs, are used to inhibit tumor cell growth and/or reduce white cell count.

In one embodiment, doses of between 13.3 grams to 60 grams of Sheng Di Huang, or 3.3 grams to 30 grams of Da Huang, or both, alone or in combination with one of more of the other herbs, and/or in combination with additional emodin or digoxin, respectively, are administered daily or 2-3 times daily before meals or up to 10× daily or less than daily even as little as three times a month. In other embodiments, the regimen described further includes 3.3 grams to 30 grams of Jin Yin Hua. In other embodiments, two of these three are included in the regimen. In further embodiments, one, two, three or all four of the herbs Mu Dan Pi, Xian He Cao, Chun Gen Pi and Di Gu Pi is/are combined with one, two or all of the three herbs Sheng Di Huang, Da Huang and Jin Yin Hua, including 3.3 grams to 15 grams of any of the other four of the seven herbs, e.g., 3.3 grams to 15 grams of Mu Dan Pi, 3.3-10 grams to 15 grams of Xian He Cao, 3.3-10 grams to 15 grams of Chun Gen Pi, and/or 3.3-5 grams to 15 grams of Di Gu Pi.

In one example involving a combination of emodin or digoxin, or both, with the three herbs, 40 grams of Sheng Di Huang in 100 grams of water, 15 grams of Da Huang in 60 grams of water and 15 grams of Jin Yin Hua in 60 grams of water may be combined in a single treatment dosage and administered to a patent. The combination may be cooked once or twice, and the herb:liquid ratio may be 1:10 or otherwise. The dose may be 1-10 days or even multiple times daily including 2-6 times daily, and even as often as 10 times daily.

In another example, a treatment regimen includes a combination of emodin or digoxin, or both, with the seven herbs, such as 5 grams of Mu Dan Pi in 15 grams of water, 20 grams of Sheng Di Huang in 80 grams of water, 5 grams of Xian He Cao in 15 grams of water, 5 grams of Chun Gen Pi in 15 grams of water, 5 grams of Di Gu Pi in 15 grams of water, 10 grams of Da Huang in 40 grams of water and 10 grams of Jin Yin Hua in 40 grams of water. The combination may be cooked once or twice, and the herb:liquid ratio may be 1:10 or otherwise. The dose may be 1-10 days or even multiple times daily including 2-6 times daily, and even as often as 10 times daily.

In another example, a low dose formula involving emodin or digoxin, or both, with the eighteen herbs includes 3.3 grams of Da Huang in about 32 grams water, 13.3 grams of Sheng Di Huang in about 129 grams of water, 3.3 grams of Jin Yin Hua in about 32 grams of water, 3.3 grams of Mu Dan Pi in about 32 grams of water, 5 grams of Di Gu Pi in about 48 grams of water, 10 grams of Xian He Cao in about 97 grams of water, 10 grams of Chun Gen Pi in about 97 grams of water, 8.3 grams of Zi Cao in about 80 grams of water, 6.7 grams of Xuan Shen in about 65 grams of water, 3.3 grams of Shi Gao in about 32 grams of water, 4 grams of Bai Shao in about 39 grams of water, 4 grams of Chi Shao in about 39 grams of water, 3.3 grams of Hong Hua in about 32 grams of water, 8.3 grams of Da Qing Ye in about 80 grams of water, 6.7 grams of Qing Dai in about 65 grams of water, 6.7 grams of Bai Zhu in about 65 grams of water, 5 grams of Shi Wei in about 48 grams of water, and 2 grams of Rou Gui in about 19 grams of water.

In another example, a high dose formula involving emodin or digoxin, or both, with the eighteen herbs includes 30 grams of Da Huang in about 300 grams of water, 60 grams of Sheng Di Huang in about 600 grams of water, 30 grams of Jin Yin Hua in about 300 grams of water, 15 grams of Mu Dan Pi in about 150 grams of water, 15 grams of Di Gu Pi in about 150 grams of water, 15 grams of Xian He Cao in about 150 grams of water, 15 grams of Chun Gen Pi in about 150 grams of water, 5 grams of Zi Cao in about 50 grams of water, 5 grams of Xuan Shen in about 50 grams of water, 5 grams of Shi Gao in about 50 grams of water, 5 grams of Bai Shao in about 50 grams of water, 5 grams of Chi Shao in about 50 grams of water, 5 grams of Hong Hua in about 50 grams of water, 5 grams of Da Qing Ye in about 50 grams of water, 5 grams of Qing Dai in about 50 grams of water, 5 grams of Bai Zhu in about 50 grams of water, 5 grams of Shi Wei in about 50 grams of water, and 5 grams of Rou Gui in about 50 grams of water. In another example, a low dose formula involving emodin or digoxin, or both, with the seven herbs includes 3.3 grams of Da Huang in about 32 grams water, 13.3 grams of Sheng Di Huang in about 129 grams of water, 3.3 grams of Jin Yin Hua in about 32 grams of water, 3.3 grams of Mu Dan Pi in about 32 grams of water, 5 grams of Di Gu Pi in about 48 grams of water, 10 grams of Xian He Cao in about 97 grams of water, and 10 grams of Chun Gen Pi in about 97 grams of water.

In another example, a high dose formula involving emodin or digoxin, or both, with the seven herbs includes 30 grams of Da Huang in about 300 grams of water, 60 grams of Sheng Di Huang in about 600 grams of water, 30 grams of Jin Yin Hua in about 300 grams of water, 15 grams of Mu Dan Pi in about 150 grams of water, 15 grams of Di Gu Pi in about 150 grams of water, 15 grams of Xian He Cao in about 150 grams of water, and 15 grams of Chun Gen Pi in about 150 grams of water.

In another example, a low dose formula involving emodin or digoxin, or both, with the three herbs includes 3.3 grams of Da Huang in about 32 grams water, 13.3 grams of Sheng Di Huang in about 129 grams of water, and 3.3 grams of Jin Yin Hua in about 32 grams of water.

In another example, a high dose formula involving emodin or digoxin, or both, with the three herbs includes 30 grams of Da Huang in about 300 grams water, 60 grams of Sheng Di Huang in about 600 grams of water, and 30 grams of Jin Yin Hua in about 300 grams of water.

In another example, a medium dose formula involving emodin or digoxin, or both, with the three herbs includes 10 grams of Da Huang in about 100 grams water, 25 grams of Sheng Di Huang in about 250 grams of water, and 10 grams of Jin Yin Hua in about 100 grams of water.

In another example, a medium dose formula involving emodin or digoxin, or both, with the three herbs includes 20 grams of Da Huang in about 200 grams water, 40 grams of Sheng Di Huang in about 400 grams of water, and 20 grams of Jin Yin Hua in about 200 grams of water.

In another example, a medium dose formula involving emodin or digoxin, or both, with the three herbs includes 15 grams of Da Huang in about 150 grams water, 35 grams of Sheng Di Huang in about 350 grams of water, and 15 grams of Jin Yin Hua in about 150 grams of water.

In another example, a medium dose formula involving emodin or digoxin, or both, with the three herbs includes 25 grams of Da Huang in about 250 grams water, 45 grams of Sheng Di Huang in about 450 grams of water, and 25 grams of Jin Yin Hua in about 250 grams of water.

In another example, a low dose formula involving emodin or digoxin, or both, with the two herbs includes 3.3 grams of Da Huang in about 32 grams water, and 13.3 grams of Sheng Di Huang in about 129 grams of water.

In another example, a high dose formula involving emodin or digoxin, or both, with the two herbs includes 30 grams of Da Huang in about 300 grams water, and 60 grams of Sheng Di Huang in about 600 grams of water.

In another example, a medium dose formula involving emodin or digoxin, or both, with the two herbs includes 10 grams of Da Huang in about 100 grams water, and 30 grams of Sheng Di Huang in about 300 grams of water.

In another example, a medium dose formula involving emodin or digoxin, or both, with the two herbs includes 20 grams of Da Huang in about 300 grams water, and 45 grams of Sheng Di Huang in about 450 grams of water.

In another example, a medium dose formula involving emodin or digoxin, or both, with the two herbs includes 15 grams of Da Huang in about 32 grams water, and 40 grams of Sheng Di Huang in about 400 grams of water.

In another example, a medium dose formula involving emodin or digoxin, or both, with the two herbs includes 25 grams of Da Huang in about 300 grams water, and 50 grams of Sheng Di Huang in about 500 grams of water.

Examples of medium dose formulas for emodin or digoxin, or both, with the seven herb and eighteen herb combinations are also provided commensurate with the medium dose formulas for the two and three herbs combinations including corresponding percentage changes in the other four and other 15 herbs. Many other combinations may be used depending on characteristics of the patient such as age and weight, the condition of the patient, and the patient's history.

Doses in between the low dose and high dose examples for the two herb formula, the three herb formula, the seven herb formula, and the eighteen herb formula are also within the scope of further examples. Under certain conditions, doses above the high dose formula or below the low dose formula may be used as determined by a physician using his or her expertise and experience both generally in the field and with specific patients. In addition, other combinations of two, three, four, five, or more of these 18 herbs may be used in further examples of formulas wherein the dose ranges described in the above examples or otherwise as determined by a physician may be used. Further herbs not described herein may also be included in formulas including combinations of the described herbs.

In the examples above, certain doses of herb combinations have been described in certain amounts of water. Mixing the herbs in water is only one example of a way to take the herbal combinations. Instead, no water may be used and instead another liquid may be used. The herbs may be formed into pills or capsules, or an IV may be used. Any of the herbal combinations may be formed into a cream and rubbed onto the skin, or a syringe may be used to inject a patient with an herbal combination.

In another example, the effect of CXCR4 antagonists on the survival of NB4, HL60, Jurkat leukemic cells and HT29 colon cancer and prostate tumor cells was examined. Digoxin significantly inhibited the growth of leukemic cells at concentrations between (0.05- to 1 microgram/ml). Emodin by itself inhibited the growth of leukemic cells only at concentrations of more than 5 microgrm/ml. Combinations of digoxin at concentrations of 0.1 microgram/ml and either 5 or 10 microgram/ml of emodin increased significantly the tumor killing ability of both compounds. Digoxin, Emodin, and their combination also add partial however significant effect on HT29 tumor cells.

The effect of the proliferation of digoxin, emodin, and their combination on the viability of cancer cell lines from different origin was studied. Harvested non adherent human hematopoietic cancer cell lines NB4, HL60 and Jurkat, cells were seeded at $2 \times 10^5$ viable cells/1 ml per well into a 24-well plate in triplicates in a medium supplemented with 10% FCS and incubated with different concentrations of digoxin, emodin, and their combination for 24 hours. Following the incubation, the cells were stained with propidium iodide (PI) (Sigma, St. Louis, Mo.) and percent of viable PI-negative cells in culture was determined by FACScalibur analysis (Becton Dickinson Immunocytometry Systems), using CellQuest software. Adherent prostate cancer PC3 cells and colon cancer HT29 cells were seeded at $1 \times 10^{0.5}$ viable cells/1 ml per well into a 24-well plate under conditions described above, and following a 24-hour exposure to digoxin, emodin, and their combination the cells were harvested, washed with PBS and stained with PI and counted as described for hematopoietic cells.

The therapeutic index of digoxin is understood to be between 0.125 m"g to 0.5 m"g, while the LD50 values of emodin in mice are understood to be 0.56 g/k"g.

When combining D and E in accordance with certain embodiments, and/or combining digoxin or emodin, or both, with one or more of the herbs, there is a surprising and unexpected symbiotic effect.

Certain treatments may be prepared as a mixture of herbs that are known to have separately digoxin "D" and emodin "E". Aloe-emodin is a natural anthraquinone compound that is present in some traditional medicinal plants such as Rhei Rhizoma and Rheum palmatum. Interestingly, aloe-emodin has been found to have lesser cytotoxicity towards normal human cells. In-vitro tests with synthesized D&E molecules have been performed on a cell-line. The in-vitro with the plants was similar to the one with the isolated molecules.

Emodin may be extracted from traditional medicinal plants such as Rhei Rhizoma and Rheum Palmatum. In one embodiment, the source of Emodin used is Da Huang-Chinese name, or Rhubarb Root-English name, or Rheum Plamatum-Botanical name, or Radix Rhisoma Rhei-Pharmaceutical name. Emodin may be extracted from Rhubarb, Buckthorn and/or Japanese Knotweed (Fallopia Japonica). Aloe-emodin may be used which is a variety of emodin found in Socotrine, Barbados, and Zanzibar aloes.

A medicinal cancer treatment using Emodin is prepared in certain embodiments by mixing the herb, Da Huang, in water at a ratio of approximately 10:1. The herb may be ground to a fine powder. The water may be added to the fine powdered herb, and the pot covered. After boiling, the heat is lowered in certain embodiments to about 70 degrees centigrade. The aqueous mixture is cooked for another hour. The liquid is then strained into a container. In some cases, this may be done twice. In the second cooking, the ratio may be reduced to 7.5:1. The second cooking may take about 45 minutes including the boiling.

Single herbs or combinations of two or more herbs alone or with any one or more of the described molecules may be prepared in a process involving the following or a subset or variation thereof: grinding the herbs to a fine texture in the mixer for around 2-3 min until it looked fine powder; weighing the powder (e.g., 25 gm) and transferring to a beaker (e.g., 2000 ml); adding distilled water (RT) to powdered herbs in a ratio of 1:20 (gm of herbs: ml of water) and soaking the herbs for 15-20 min; boiling the mixture to 85-90° C.; cooling the temperature of the mixture down to 70-75° C. after removing it from the hot plate; covering the beaker properly with aluminum paper and cooking the mixture at 70° C. on hot plate—the total time of cooking of the mixture may be approximately 60 min which includes boiling, cooling it down and cooking; straining the mixture with the help of a manual strainer; after filtration, centrifuging the extract at 5000 rpm for 15 min and collecting the supernatant; filter sterilizing the supernatant by passing through 0.2 μm syringe filter; storing the clear filtrate at 4° C.-subsequent dilutions may be prepared.

The source of Digoxin in certain embodiments is Sheng Di Huang-Chinese name, or Foxglove root-English name, or Radix Rhemania-Pharmaceutical name. The preparation of the Digoxin may be the same as for the Emodin. In certain embodiments, the herbs from which the Emodin and Digoxin are extracted are cooked together. Digoxin may be extracted from Digitalis Purpurea or Purple Foxglove.

In certain embodiments, the preparede treatment is not pure. For example, certain treatments may involve a "vegetable soup" type regiment made of more than one and even two, three, seven or eighteen herbal ingredients per specific examples provided herein, or any combinations of the herbs described herein, or combinations of the herbs described herein with other herbs not mentioned herein. In certain embodiments, herbal ingredients are mixed in solution and a patient may drink the liquid. While freeze-drying the herb in powder form may be possible, the above-described process appears to be more effective.

Harvested non adherent human hematopoietic cancer cell lines NB4 (AML), HL60 and Jurkat were seeded at $2\times10^5$ viable cells/1 ml per well into a 24-well plate in triplicates in a medium supplemented with 10% FCS and incubated with different concentrations of digoxin, Emodin, and their combination for 24 hours. Following the incubation, the cells were stained with propidium iodide (PI) (Sigma, St. Louis, Mo.) and percent of viable PI-negative cells in culture was determined by FACScalibur analysis (Becton Dickinson Immunocytometry Systems), using CellQuest software. Adherent prostate cancer PC3 cells and colon cancer HT29 cells were seeded at $1\times10^5$ viable cells/1 ml per well into a 24-well plate under conditions described above, and following 24-hour exposure to digoxin, Emodin, and their combination, the cells were harvested, washed with PBS and stained with PI and counted as described for hematopoietic cells.

A cancer or other disease treatment including administering a cocktail including emodin, digoxin, or a combination of emodin and digoxin, or a combination of emodin with one or more herbs, or a combination of digoxin with one or more herbs, or other combinations of the herbs and/or molecules described herein may be combined with other treatments. For example, a treatment of Acute Lymphoblastic Leukemia (ALL) is provided, including a combination of emodin or digoxin, or both, alone or with one or more of the herbs or other molecules described herein, with one or more of Vincristine Sulfate, Cyclophosphamide, Doxorubicin Hydrochloride, Methotrexate, Clofarabine, Cytarabine, Dasatinib, Daunorubicin Hydrochloride, Gleevec (Imatinib Mesylate), Nelarabine, or Oncaspar (Pegaspargase).

A treatment of Acute Monocytic Leukemia (AML) is provided, including a combination of emodin or digoxin, or both, alone or with one or more of the herbs or other molecules described herein, with one or more of Cyclophosphamide, Cytarabine, Doxorubicine, Daunorubicin, or Vincristine.

A treatment of Melanoma is provided, including a combination of emodin or digoxin, or both, alone or with one or more of the herbs or other molecules described herein, with one or more of Aldesleukin (Proleukin), Dacarbazine, Ipilimumab (Yervoy), or Peginterferon-alpha.

Another treatment of Melanoma is provided, including a combination of emodin or digoxin, or both, alone or with one or more of the herbs or other molecules described herein, with one or more of Paclitaxel, Cisplatin, Carboplatin, Vinblastine, Vincristine or Vindesine. Other embodiments include combinations of any one or more of these with one or more of Aldesleukin (Proleukin), Dacarbazine, Ipilimumab (Yervoy) or Peginterferon-alpha.

A treatment of multiple myeloma or other hematological cancer is provided, including a combination of emodin or digoxin, or both, alone or with one or more of the herbs or other molecules described herein, with one or more of Talidomid, Revlomid or Valkade.

A treatment of chronic myeloid leukemia (CML) or other hematological cancer is provided, including a combination of emodin or digoxin, or both, alone or with one or more of the herbs or other molecules described herein, with one or more of Gleevac, Dasatinib, Sprycel, Nilotinib, Tasigna, Hydroxyurea or Hydrea.

A treatment of non-Hodgkins lymphoma or other hematological cancer is provided, including a combination of emodin or digoxin, or both, alone or with one or more of the herbs or other molecules described herein, with an RCHOP combination, including Retuximab and/or Mabtera, and a combination of Cyclophosphamide, Doxorubicin Hydrochloride, Hydroxydaunomycin, and/or Adriamycin, Vincristine Sulfate and/or Oncovin, and Prednisone.

A treatment of Hodgkins lymphoma or other hematological cancer is provided, including a combination of emodin or digoxin, or both, alone or with one or more of the herbs or other molecules described herein, with an ABVD combination, including Doxorubicin Hydrochloride, Hydroxydaunomycin, and/or Adriamycin, Bleomycin, Vinblastine and Dacarbazine and/or Procarbazine.

A treatment of colon cancer or other adenocarcinoma is provided, including a combination of emodin or digoxin, or both, alone or with one or more of the herbs or other molecules described herein, with Folfiri q Folfox combination, including a combination of fluorouracil –5Fu, Oxaliplatinim, irinotecan, and leucovorin or subset thereof.

A treatment of non-small cell lung cancer (NSCLC) or other adenocarcinoma is provided, including a combination of emodin or digoxin, or both, alone or with one or more of the herbs or other molecules described herein, with one or more of Cisplatinum, etoposide, mitomycin C or vindesine.

A treatment of prostate cancer or other adenocarcinoma is provided, including a combination of emodin or digoxin, or both, alone or with one or more of the herbs or other molecules described herein, with one or more of Taxotere, Paclitaxel, Docetaxel, Mitoycin C, Doxorubicin, Mitozantrone, vinblastine, Etoposide, or Estramustine Phosphate.

A treatment of breast cancer or other adenocarcinoma is provided, including a combination of emodin or digoxin, or both, alone or with one or more of the herbs or other molecules described herein, with one or more of cyclophosphamide, doxorubicin, Adriamicin, fluorouracil, 5fu, or Taxol.

A treatment of epidermal oral carcinoma or other adenocarcinoma is provided, including a combination of emodin or digoxin, or both, alone or with one or more of the herbs or other molecules described herein, with one or more of Taxol, Carboplatinum, or Erbitux.

A treatment of glioblastoma or other adenocarcinoma is provided, including a combination of emodin or digoxin, or both, alone or with one or more of the herbs or other molecules described herein, with one or more of TEMODAL, temozolomide, or Avastin.

A cancer or other disease treatment including administering a cocktail including emodin, digoxin, or a combination of emodin and digoxin, or a combination of emodin with one or more herbs, or a combination of digoxin with one or more herbs, or other combinations of the herbs and/or molecules described herein may also be combined with other treatments such as may be understood by those skilled in the art and/or as may be described in literature such as the following which are hereby incorporated by reference as disclosing alternative embodiments and compounds that may be combined with emodin or digoxin, or both, in a cocktail or otherwise effective cancer therapy:

Chronic Lymphocytic Leukemia by the Leukemia & Lymphoma Society;

Medifocus.com Medifocus Guide on Chronic Lymphocytic Leukemia;

Ranjit Thomas, et al., Spontaneous Clinical Regression in Chronic Lymphocytic Leukemia, British Journal of Haematology, 2002, 116, 341-345;

Dragomir Marisavljevic, et al., Spontaneous Clinical Remission of Chronic Lymphocytic Leukemia, Haema 2003; 6(3): 394-397;

Upshaw J D Jr, et al., Spontaneous Remission of B cell Chronic Lymphocytic Leukemia associated with T Lymphocytic Hyperplasia in bone marrow, South Med J. 22 Jun. 1995(6): 647-9;

Wiernik P H, Second neoplasms in patients with chronic lymphocytic leukemia, Current Treat Options Oncol. June 2004; 5(3):215-23;

Luis Fayad M D and Susan O'Brien M D, Chronic Lymphocytic Leukemia and Associated Disorders, Medical Oncology: A Comprehensive Review, 1995;

Michael J. Keating, et al., Biology and Treatment of Chronic Lymphocytic Leukemia, American Society of Hematology, Hematology 2003, 153-175;

G E Marti, et al, Descriptive Epidemiology of Chronic Lymphocytic Leukemia (CLL);

Sarfaraz K. Niazi, Handbook of Pharmaceutical Manufacturing Formulations, Culinary & Hospitality Industry Publications Services; and U.S. Pat. Nos. 5,872,103; 6,197,754; 6,740,665; 6,812,255; 7,268,162; 7,358,222; 7,381,535; 7,393,656; 7,563,584; 7,695,926; 7,790,905; and United States published applications no. 20030211180; 20050026849; 20050196473; 20060205679; 20070191262; 20080152700; 20080220441; 20090018088; 20090143279; 20090215042; 20090269772; 20100068198; 20100092585; 20100144647; 20100167286; 20120122807; 20100144647; 20050008664; 20090018088; 20100092585; and PCT published applications no. WO01/66123A2; WO2004/052294A2; WO2006/053049A2; WO2007/130124A1; and WO2012/063134A2.

A treatment regimen of periodic doses of an advantageous combination of emodin and digoxin is provided to treat psoriasis. Another treatment regimen for psoriasis includes a combination of emodin (E) and digoxin (D) with Jin Yin Hua, Sheng Di Huang and Da Huang, otherwise referred to herein as the three herb combination or "3-HX.". Another treatment regimen for psoriasis includes a combination of emodin and digoxin, or D&E, and Jin Yin Hua, Sheng Di Huang and Da Huang or 3-HX, with Mu Dan Pi, Di Gu Pi, Xian He Cao and Chun Gen Pi, which forms a combination of D&E and the seven herb combination referred to herein. The treatment regimen may be administered topically, orally, subcutaneously or intravenously.

Anti-psoriatic activity of 3-HX, and of D&E was determined in studies using 12-O-Tetradecanoylphorbol-β-Acetate (TPA) induced ear inflammation in male C57BL/6 mice. All the animals were randomized based upon the body weight and allotted to seven groups with 6 animals in each group. Groups G1 and G2 were treated topically with test item 3HX at the dose levels of 1:4 and 1:8 dilutions respectively. Groups G3 and G4 were treated orally with test item 3HX at the dose levels of 500 and 1000 mg/kg respectively. Group G5 and G6 were treated topically and orally with D and E respectively. Group G7 served as both TPA control (right ear) and solvent control (left ear) and was treated orally with Na-CMC.

Among the various experimental groups topical application of 3-HX (1:4) and D&E and oral treatment of low dose of 3-HX (500 mg/kg) and D & E exhibited maximum reduction in ear thickness. Similar trend of test items response was observed in TPA-induced ear thickness change. Topical application of test items exerted optimum % inhibitory activity against TPA induced ear inflammation in mice whereas oral treatment exhibited marginal anti-inflammatory activity. In the punch biopsy weight investigation maximum reduction was obtained in topically D & E and 3-HX (1:4) treated groups whereas marginal reduction was obtained on oral treatment with test items. The epidermal ear thickness results obtained from histopathological photographs were in accordance with punch biopsy weight results where topical application of test items was found to exert better effect in comparison with oral treatment. Among the evaluation of test items over inflammatory biomarkers viz., enzyme myeloperoxidase (MPO) and nitric oxide levels, topical application of D & E and 3-HX (1:4) resulted in marked suppression of enzyme MPO activity whereas marginal inhibition of nitric oxide content generation was obtained on oral administration of test items respectively. Thus, based upon the present experiment findings it is suggested that topical application of 3-HX at the ratio of 1:4 and D & E as well as oral treatment of low dose of 3-HX (500 mg/kg) may act as promising drug candidate for the treatment of psoriasis.

TEST ITEM INFORMATION

TEST ITEM-1

| | |
|---|---|
| Name of the test item/code | 3-HX |
| Lot No. | NA |
| Pack Size | NA |
| Physical Description | NA |
| Storage condition | Room Temperature |
| Test Item Analysis | Analysis for the identity and purity of the test item was not conducted as part of this study, and is the responsibility of the sponsor |

TEST ITEM-2

| | |
|---|---|
| Name of the test item/code | Digoxin (D) |
| Lot No. | 051M1374V |
| Pack Size | NA |
| Physical Description | White to off white powder |
| Storage condition | At Room Temperature |
| Test Item Analysis | Analysis for the identity and purity of the test item was not conducted as part of this study, and is the responsibility of the Sponsor |
| Precautions in handling | Avoid contact with skin and eyes |

TEST ITEM-3

| | |
|---|---|
| Name of the test item/code | Emodin (E) |
| Lot No. | M3074 |
| Pack Size | NA |
| Physical Description | Orange powder |
| Storage condition | Stored at +4° C. |
| Test Item Analysis | Analysis for the identity and purity of the test item was not conducted as part of this study, and is the responsibility of the sponsor |
| Precautions in handling | Avoid contact with skin and eyes |

VEHICLE CONTROL
2% DMSO in methanol

TEST SYSTEM

| | |
|---|---|
| Species | *Mus musculus* |
| Strain | C57BL/6 |
| Source | Animal Facility, Dabur Research Foundation |
| Sex | Male |
| Age | 6-8 Weeks |
| Body weight range | 16.47-36.51 g |
| Acclimatization | 12 Days |
| Randomization | Animals were randomized based on their body weight |
| Identification of animals | By cage labeling and tail marking |
| Total no of animals | 42 |
| Total no of groups | 7 |
| Total no of animals per group | 6 |
| Total no of animals per cage | 6 |

ANIMAL HUSBANDRY CONDITIONS

| | |
|---|---|
| Room temperature | 21.8 to 24.2° C. |
| Relative humidity | 56 to 59% |
| Light/dark cycle | 12-hourly |
| Feed | Conventional feed purchased from a Golden feed, Mehrauli was provided ad libitum to the animals. |
| Water | Filtered drinking water was provided ad libitum. |

Justification for Selection of Test System

Male C57BL/6 mice were selected as the test system, as they were commonly reported in literature to evaluate the effect of test item for anti-psoriatic potential on TPA induced ear inflammation model.

CHEMICALS

| Name of the Chemical | Catalogue No. or CAS No. | Company | Lot No. or Batch No. |
|---|---|---|---|
| Phorbol 12-myristate 13-acetate (TPA) | P8139-1MG | Sigma life sciences, USA | SLBC5412V |
| Dimethyl sulfoxide (DMSO) | 67-68-5 | Merck Specialties Pvt Ltd., Mumbai, India | 80291205001730 |
| Methanol | M0275 | RANKEM Fine Chemicals Ltd. New Delhi, India | R106M10 |
| Sodium dihydrogen phosphate 2-hydrate cryst. Pure | 17845 | Merck Specialties Pvt Ltd., Mumbai, India | DL1DR511556 |
| Hexadecyltrimethyl-ammonium bromide | H5882 | Sigma life sciences, USA | 120M0141V |
| o-Dianisidine Dihydrochloride | 195136 | MO Biomedicals LLC | M1271A |
| di-Sodium hydrogen phosphate anhydrous Purified | 7558-79-4 | Merck Specialties Pvt Ltd., Mumbai, India | MF7M571743 |
| Hydrogen Peroxide Solution | 7722-84-1 | Fisher Scientific | 1889 7202-5 |
| Orthophosphoric acid | 7664-38-2 | Fisher Scientific | 1309 7100-5 |
| Sulphanilamide | 63-74-1 | Central Drug House Pvt Ltd. New Delhi | 930308 |
| Glycine 98% | 56-40-6 | Acros Organics, USA | A013597501 |
| Sodium chloride | 7647-14-5 | Merck Specialties Pvt Ltd., Mumbai, India | MJ0M602975 |
| Hydrochloric acid min. 35% GR | 7647-01-0 | Merck Specialties Pvt Ltd., Mumbai, India | HD7H570285 |

Method

Principle

Excessive proliferation of keratinocytes is a characteristic of psoriasis, and this cell type is a well reported target of therapy for this disease. In the present study, chronic skin inflammation was induced by repeated topical application of TPA, which is recognized by prolonged skin reaction & epidermal hyperplasia. In this model the potential of three test items—3-HX, Digoxin (D) and Emodin (E) were evaluated for reduction of epidermal hyperplasia reflected by change in ear thickness & keratinocyte proliferation in C57BL/6 mice.

Experimental Procedure

The study was conducted on healthy, adult, male C57BL/6 mice. All the animals were acclimatized to laboratory condition prior to experiment initiation.

5 mg/ml stock of TPA was prepared in DMSO and aliquot of the same was diluted to 1:50 with methanol to achieve final TPA concentration of 100 µg/ml for topical application. For oral application of 3-HX, a stock solution of 100 mg/ml was prepared in distilled water and was further diluted to 50 mg/mL, in-order to administer the dose of 500 mg/kg and 1000 mg/kg. For topical application, required amount of 3HX was dissolved in DMSO to obtain the final dilution of 1:4 and 1:8. For oral application of test item D, 10 mg/ml was prepared in DMSO and was further formulated with 0.25% Na-CMC to obtain final strength of 0.1 mg/ml. For topical application, required amount of D was dissolved in DMSO and methanol and stored at −20° C. Similarly, for oral application of test item E, 10 mg/ml stock was prepared in 0.25% Na-CMC and 0.1% Tween 80. For topical application, required amount of E was dissolved in DMSO and diluted with methanol.

On Day 0, all the animals were randomized based on body weight and allotted to seven groups containing 6 animals per group. Groups G1 and G2 were treated topically with test item 3HX at the dose levels of 1:4 and 1:8 dilutions respectively. Groups G3 and G4 were treated orally with test item 3HX at the dose levels of 500 and 1000 mg/kg respectively. Group G5 was treated topically with test item D and E, in combination, at the concentration of 1 µg and 100 µg respectively. Group G6 was treated orally with test item D at 1 mg/kg. After 30 min. of D administration, test item E was dosed orally at 100 mg/kg. Group G7 served as both TPA control (right ear) and solvent control (left ear) and was treated orally with Na-CMC.

20 µL of TPA solution containing 2 µg of TPA in vehicle (2% DMSO and 98% methanol) was applied topically on both ventral and dorsal side of the right ear of all the groups of animals on day 0, 2, 4, 7 and 9. However, the left ear of Group G7 animals was treated topically with 20 µL of solvent (2% Dimethylsulfoxide+98% methanol) on day 0, 2, 4, 7 and 9.

All the test item formulations was administered orally to Groups-G3, G4, and G6 at the dose volume of 10 ml/kg from day 0 to day 9. For topical application, 20 µL of test items (3HX and D+E) was dissolved appropriately in the TPA solvent i.e. methanol and applied daily from Day 0 to Day 9 to Groups-G1, G2 and G5.

The ear thickness was measured daily using digital caliper. On Day 10, animal's blood was withdrawn by retro-orbital plexus. Blood serum was separated for the estimation of nitric oxide level by Griess method. Further, all the animals were humanely sacrificed and ear punch biopsies were collected, weighed and subjected for histopathological analysis, immunohistochemical Ki-67 staining and Myeloperoxidase (MPO) activity.

TABLE 2

Allocation of Animals

| Groups | Treatment | Volume & Dose | Route | No. of Animals |
|---|---|---|---|---|
| G1 | TPA + 3HX | 20 µL + 20 µL of 1:4 | Topical | 6 |
| G2 | TPA + 3HX | 20 µL + 20 µL of 1:8 | Topical | 6 |
| G3 | TPA + 3HX | 20 µL + 500 mg/kg | Oral | 6 |
| G4 | TPA + 3HX | 20 µL + 1000 mg/kg | Oral | 6 |
| G5 | TPA + D&E | 20 µL + 20 µL of stock (1 µg D + 100 µg E) | Topical | 6 |
| G6 | TPA + D&E | 20 µL + 1 mg/kg D and 100 mg/kgE | Oral | 6 |
| G7 | TPA Control | 20 µL TPA + 0.25% Na-CMC | Oral | 6 |

Observations/Calculations

Body Weight

Body weight of all the animals was recorded from day 0 to day 10. The % change in body weight for each animal was calculated using the given formula:

% Body Weight Change=Body Weight at 'X' day−Body weight at day '0'×100 Body weight at day '0'

"x": Day 1, 2, 3, 4, 5, 6, 7, 8, 9, 10

Ear Thickness Measurement

Upper, middle and lower ear thickness of both right and left ear of Group G1 and right ear of Group G2 to G7 was measured and recorded daily from Day 0 to Day 9 using digital caliper (MITUTOYO) and their average value was considered for further calculations.

Figure 24:
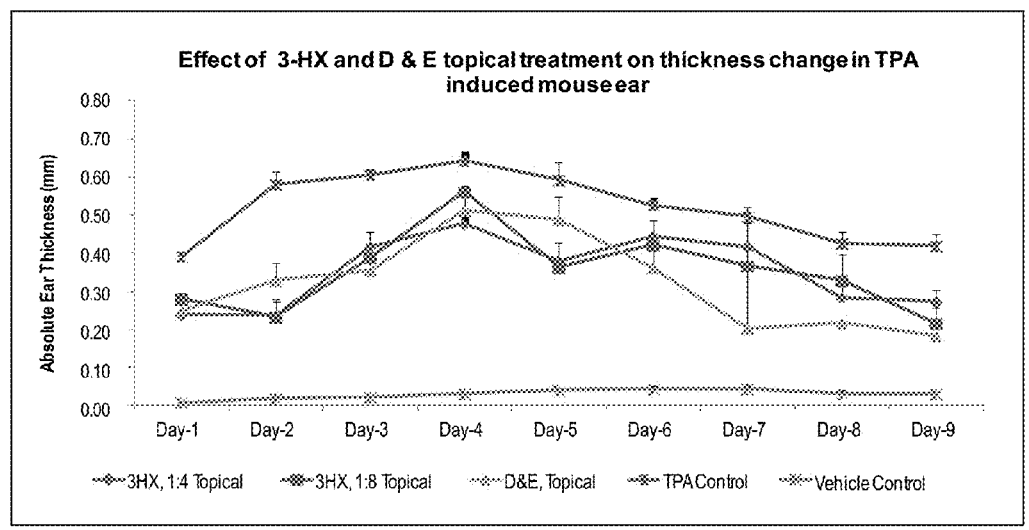
FIG. 24 illustrates effects of combinations of Sheng Di Huang, Da Huang and Jin Yin Hua and of combinations of digoxin and emodin on Ear Thickness Change.
Figure 25:
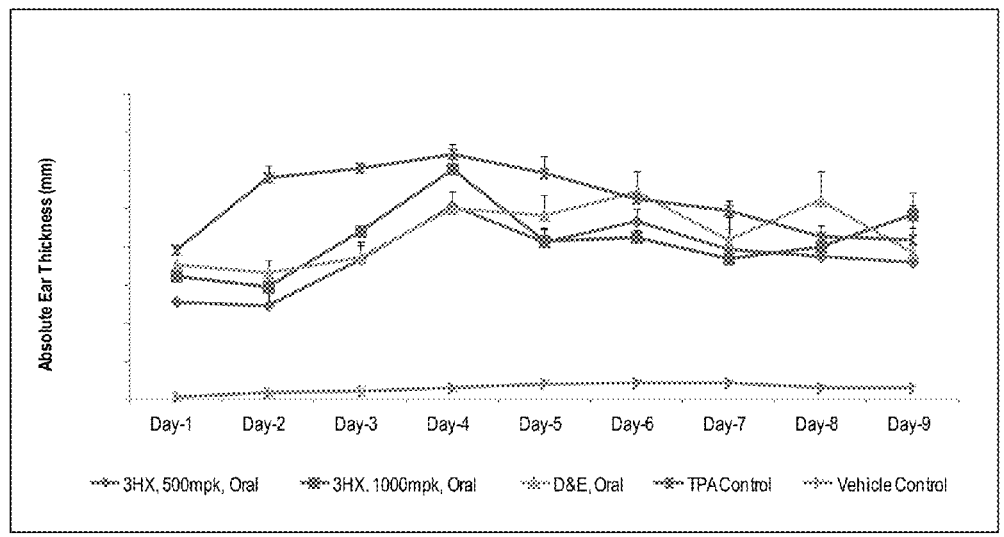
FIG. 25 illustrates effects of combinations of Sheng Di Huang, Da Huang and Jin Yin Hua and of combinations of digoxin and emodin on Ear Thickness Change.

Mean absolute ear thickness (in mm) are shown in FIGS. 24-25.

Ear Thickness Change (Etc)

Mean ear thickness change or ear edema was calculated based on the absolute ear thickness values.

Ear thickness change (mm)(x)={Absolute ear thickness (mm) at "x" Time Point}−{Absolute ear thickness(mm) at day 0}

"x": day 0, 1, 2, 3, 4, 5, 6, 7, 8, 9
Ear thickness change are shown in FIGS. 24-25.

Photograph & Ear Biopsy Weight

Photographs of ear was taken for each animal and presented. Mean ear biopsy weight (4 mm punch biopsy) was calculated and represented in tabulated and graphical form.

Percentage Inhibition of Ear Inflammation

Percentage inhibition of ear inflammation was calculated for individual animal using the formula:

=Control ETC (mm)−Test ETC (mm)/Control ETC (mm)×100

% Inhibition was tabulated and represented in graphical form.

Histopathology and Immunohistochemistry

Hematoxylin & Eosin dye stained ear histopathological photographs were subjected for epidermal ear thickness measurement using UTHSCSA Image tool, Version 3.0. The software was calibrated by Motic calibrated slide for 10× magnification and ear thickness was selected randomly at four points each for both upper and lower epidermis. Data was calculated as mean and SEM for each group and represented in tabulated and graphical form.

Myeloperoxidase (MPO) Activity

MPO activity was performed by colorimetric method as described by Rajp et al. (2007). Briefly, three punch biopsy ear (4 mm) tissue samples in each group were pooled, weighed and homogenized (100 mg/3 mL) in 50 mM/L phosphate buffer containing 0.5% CTAB. Homogenized samples were sonicated for 10s, freezed and thawed at 20-30° C. for three times, and centrifuged at 12000 rpm and 4° C. for 25 min. 250 µL of supernatant was be mixed with 625 µl of phosphate buffer (50 mmol/1, pH 6) containing 0.167 mg/ml o-dianisidine dihydrochloride and 125 µL hydrogen peroxide (0.0005%). MPO activity was calculated by using the formulae and represented in graphical and tabular form.

IU/mL=$\Delta A$×final volume in cuvette/8.3×volume of sample added (µL)×dilution factor.

Where $\Delta A$ is the average of change in absorbance per minute.

IU/gm tissue=(IU/mL)/(gm tissue/mL)

Serum Nitric Oxide Level

Nitric oxide levels was also measured by colorimetric assay using Griess reagent. Briefly, equal volume of serum was mixed with Griess reagent and incubated for 15 min at 37° C. Absorbance was measured at 546 nm and percentage inhibition of nitric oxide level was calculated using the formula:

=Control Abs−Test Abs/Control Abs×100

% Inhibition was tabulated and represented in graphical form.

Statistical Analysis

All data were expressed in Mean±SEM and suitably analyzed by Two way ANOVA and
One-way ANOVA followed by Posthoc Bonferroni and Dunett's test respectively for statistical significance. *$P<0.05$, $P<0.01$ and *$P<0.001$ for TPA control Vs vehicle or treated group.

Study Deviation

The method adopted for MPO estimation was changed as stated in the section on MYELOPEROXIDASE (MPO) ACTIVITY. Statistical analysis was done by Two way and One way ANOVA followed by Posthoc-Bonferroni and Dunnet's test respectively, as it was appropriate for study data analysis.

Results

Effect of Treatments on Body Weight Change

Figure 20:
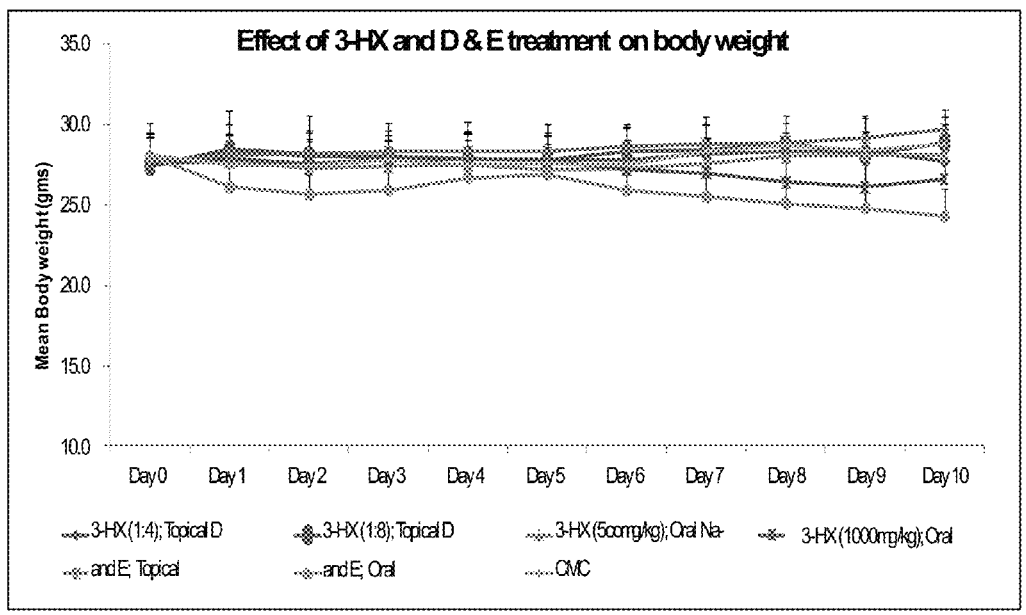
FIG. 20 illustrates effects of combinations of Sheng Di Huang, Da Huang and Jin Yin Hua and of combinations of digoxin and emodin on Body Weight.
Figure 21:
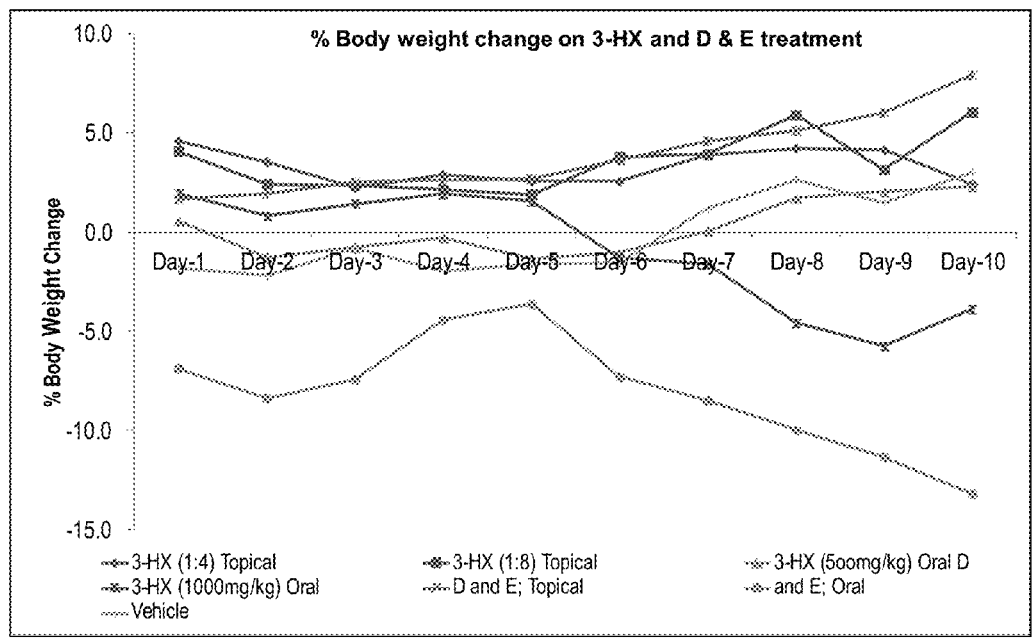
FIG. 21 effects of combinations of Sheng Di Huang, Da Huang and Jin Yin Hua and of combinations of digoxin and emodin on % Body Weight Change.

In the present study, the body weight was recorded daily for 10 consecutive days (i.e day 0 to day 9) in all the experimental groups. No significant changes in body weight were observed in any of the experimental group (Table 3; FIG. 20). % body weight change was also calculated for all the experimental groups. Marginal reduction in % body weight change was observed on oral administration of 3-HX at high dose of 1000 mg/kg and D & E treated animals (Table 4; FIG. 21).

TABLE 3

Effect of 3-HX and D & E treatment on Body Weight
(Unit: gm; Mean ± SEM)

| Treatment | Day 0 | Day 1 | Day 2 | Day 3 | Day 4 | Day 5 | Day 6 | Day 7 | Day 8 | Day 9 | Day 10 |
|---|---|---|---|---|---|---|---|---|---|---|---|
| 3-HX (1:4); Topical | 27.4 ± 2.7 | 28.5 ± 2.4 | 28.2 ± 2.4 | 27.8 ± 2.4 | 27.9 ± 2.3 | 27.8 ± 2.2 | 27.8 ± 2.3 | 28.2 ± 2.3 | 28.3 ± 2.3 | 28.3 ± 2.3 | 27.7 ± 2.4 |
| 3-HX (1:8); Topical | 27.5 ± 2.0 | 28.4 ± 1.6 | 28.0 ± 1.6 | 28.0 ± 1.6 | 27.9 ± 1.6 | 27.8 ± 1.5 | 28.3 ± 1.6 | 28.4 ± 1.6 | 28.9 ± 1.6 | 28.1 ± 1.4 | 28.9 ± 1.6 |
| 3-HX (500 mg/kg); Oral | 27.6 ± 1.6 | 27.7 ± 1.6 | 27.3 ± 1.6 | 27.4 ± 1.6 | 27.5 ± 1.6 | 27.2 ± 1.6 | 27.3 ± 1.6 | 27.6 ± 1.6 | 28.0 ± 1.5 | 28.1 ± 1.5 | 28.1 ± 1.4 |
| 3-HX (1000 mg/kg); Oral | 27.5 ± 1.7 | 27.97 ± 1.6 | 27.6 ± 1.5 | 27.8 ± 1.6 | 27.9 ± 1.5 | 27.8 ± 1.5 | 27.2 ± 1.8 | 27.0 ± 1.7 | 26.4 ± 2.0 | 26.1 ± 2.2 | 26.6 ± 2.2 |
| D and E; Topical | 27.7 ± 1.6 | 28.1 ± 1.4 | 28.2 ± 1.3 | 28.3 ± 1.3 | 28.3 ± 1.3 | 28.3 ± 1.2 | 28.6 ± 1.2 | 28.8 ± 1.2 | 28.9 ± 1.2 | 29.2 ± 1.2 | 29.7 ± 1.2 |
| D and E; Oral | 28.0 ± 1.5 | 26.1 ± 1.3 | 25.64 ± 1.3 | 25.9 ± 1.2 | 26.7 ± 1.2 | 26.9 ± 1.3 | 25.9 ± 1.4 | 25.5 ± 1.5 | 25.1 ± 1.6 | 24.8 ± 1.6 | 24.3 ± 1.7 |
| Na-CMC | 28.1 ± 1.4 | 27.5 ± 1.2 | 27.4 ± 1.1 | 27.8 ± 1.2 | 27.5 ± 1.1 | 27.6 ± 1.0 | 27.5 ± 0.9 | 28.3 ± 0.8 | 28.7 ± 0.8 | 28.4 ± 0.8 | 28.8 ± 0.9 |

Each column represents mean±SEM of n=6 mice. Data was statistically analyzed by Two way ANOVA followed by Posthoc Bonferrini's test. No statistical significance was obtained in any of the experimental group.

FIG. 20 illustrates effects of 3-HX and D & E treatment on Body weight change.

TABLE 4

Effect of 3-HX and D & E treatment on % Body Weight Change

| Treatment | Day-1 | Day-2 | Day-3 | Day-4 | Day-5 | Day-6 | Day-7 | Day-8 | Day-9 | Day-10 |
|---|---|---|---|---|---|---|---|---|---|---|
| 3-HX (1:4); Topical | 4.6 | 3.6 | 2.3 | 2.9 | 2.6 | 2.6 | 3.9 | 4.2 | 4.1 | 2.4 |
| 3-HX (1:8); Topical | 4.1 | 2.4 | 2.4 | 2.1 | 1.9 | 3.8 | 3.9 | 5.9 | 3.2 | 6.1 |
| 3-HX (500 mg/kg); Oral | 0.5 | 0.5 | −0.8 | −0.3 | −1.3 | −1 | 0 | 1.7 | 2.1 | 2.3 |
| 3-HX (1000 mg/kg); Oral | 2 | 0.8 | 1.4 | 1.9 | 1.5 | −1.3 | −1.6 | −4.6 | −5.7 | −3.9 |
| D and E; Topical | 1.7 | 1.9 | 2.5 | 2.6 | 2.7 | 3.6 | 4.6 | 5.1 | 6 | 7.9 |
| D and E; Oral | −6.9 | −8.4 | −7.4 | −4.4 | −3.6 | −7.3 | −8.5 | −10 | −11.3 | −13.2 |
| Vehicle | −1.8 | −2.2 | −0.8 | −2 | −1.6 | −1.6 | 1.2 | 2.6 | 1.5 | 3 |

Each column represents mean±SEM of n=6 mice.

FIG. 21 illustrates effects of 3-HX and D & E treatment on % Body Weight Change.

Effect of Treatments on Absolute Ear Thickness

In the present study, the absolute ear thickness was calculated daily for 10 consecutive days (i.e day 0 to day 9) in all the experimental groups (Table 5). Significant increase (P<0.001) in ear thickness was observed in the TPA control (Group7/Right ear) when compared with the vehicle control (Group7/Left ear) in entire treatment schedule.

Topical application of 3-HX at both the tested ratios of 1:4 and 1:8 significantly reduced the absolute ear thickness when compared with TPA control. Similarly, topical application of D & E also significantly reduced the absolute ear thickness when compared with TPA control (P<0.001) (FIG. 22).

Oral administration of 3-HX at dose of 500 mg/kg and 1000 mg/kg was found to significantly reduce TPA induced absolute ear thickness. D & E treatment also markedly reduced absolute ear thickness on oral administration for 10 days (P<0.001) (FIG. 23).

Each column represents mean±SEM of n=6 mice. Data was statistically analyzed by Two way ANOVA followed by Posthoc Bonferroni test. *P<0.001, P<0.01 and *P<0.05 for vehicle control Vs TPA control; Treatment Vs TPA control.

Figure 22:
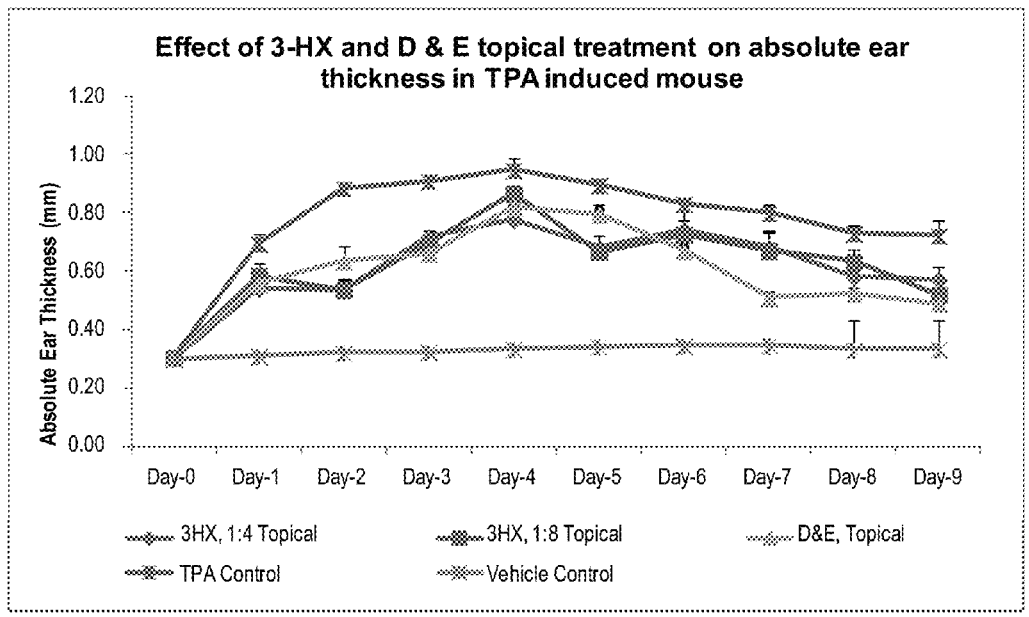
FIG. 22 illustrates effects of combinations of Sheng Di Huang, Da Huang and Jin Yin Hua and of combinations of digoxin and emodin on Absolute Ear Thickness.

FIG. 22 illustrates effects of topical application of 3-HX and D & E on Absolute Ear Thickness in TPA induced mouse.

Figure 23:
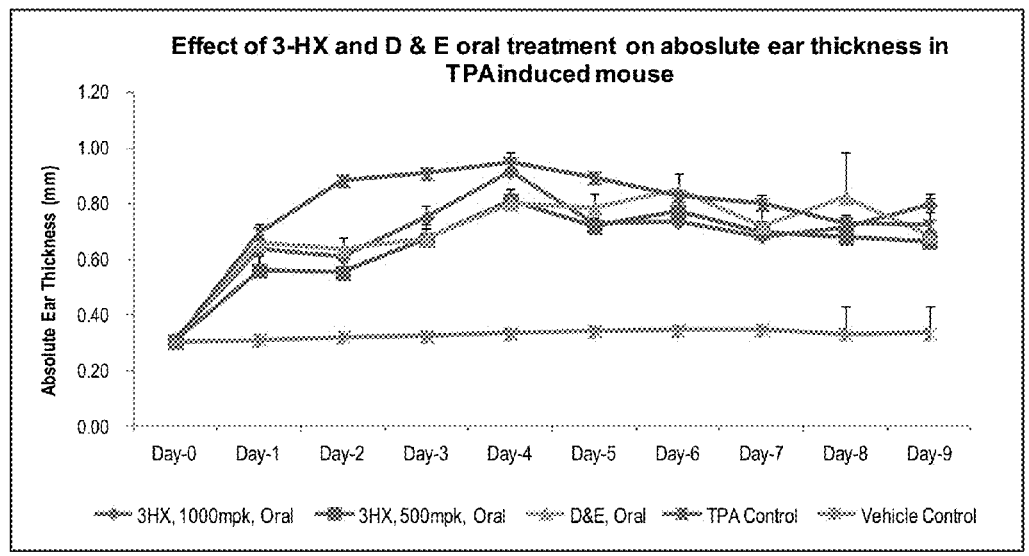
FIG. 23 illustrates effects of combinations of Sheng Di Huang, Da Huang and Jin Yin Hua and of combinations of digoxin and emodin on Absolute Ear Thickness.

FIG. 23 illustrates effects of oral application of 3-HX and D & E on Absolute Ear Thickness in TPA induced mouse.

Effect of Treatment on Ear Thickness Change

The change in ear thickness was also calculated from the absolute ear thickness for all the experimental groups to find the edema caused by inflammation. In the TPA control group significant elevation in ear thickness was observed when compared with vehicle (Solvent) control (P<0.001) (Table 6).

Topical application of 3-HX at the tested ratios significantly decreased the ear edema up to Day 5 in comparison with TPA control (P<0.001). However, from Day 6 onwards marginal decrease in ear thickness change was observed.

TABLE 5

Effect of 3-HX and D & E treatment on Ear Thickness
(Unit: mm; Mean ± SEM)

| Treatment | Day-0 | Day-1 | Day-2 | Day-3 | Day-4 | Day-5 | Day-6 | Day-7 | Day-8 | Day-9 |
|---|---|---|---|---|---|---|---|---|---|---|
| 3HX, 1:4 Topical | 0.3 ± 0.01 | 0.54 ± 0.04*** | 0.54 ± 0.04*** | 0.72 ± 0.02*** | 0.78 ± 0.05*** | 0.68 ± 0.04*** | 0.75 ± 0.05*** | 0.68 ± 0.05*** | 0.58 ± 0.03*** | 0.57 ± 0.04*** |
| 3HX, 1:8 Topical | 0.31 ± 0 | 0.59 ± 0.04*** | 0.54 ± 0.03*** | 0.7 ± 0.01*** | 0.87 ± 0.03** | 0.67 ± 0.02*** | 0.73 ± 0.05*** | 0.67 ± 0.07*** | 0.63 ± 0.04*** | 0.52 ± 0.02*** |
| 3HX (500 mg/kg); Oral | 0.31 ± 0 | 0.56 ± 0.05*** | 0.55 ± 0.04*** | 0.67 ± 0.04*** | 0.81 ± 0.04*** | 0.72 ± 0.03*** | 0.77 ± 0.05 | 0.7 ± 0.04*** | 0.68 ± 0.03 | 0.67 ± 0.03 |
| 3HX (1000 mg/kg); Oral | 0.31 ± 0 | 0.64 ± 0.03 | 0.61 ± 0.02*** | 0.75 ± 0.04*** | 0.92 ± 0.03 | 0.73 ± 0.02*** | 0.74 ± 0.03** | 0.68 ± 0.02*** | 0.71 ± 0.02 | 0.8 ± 0.04** |
| D&E, Topical | 0.31 ± 0 | 0.56 ± 0.03*** | 0.64 ± 0.05*** | 0.66 ± 0.04*** | 0.82 ± 0.01*** | 0.8 ± 0.03*** | 0.67 ± 0.03*** | 0.51 ± 0.02*** | 0.52 ± 0.02*** | 0.49 ± 0.02*** |
| D&E, Oral | 0.3 ± 0 | 0.66 ± 0.03 | 0.64 ± 0.04*** | 0.68 ± 0.05*** | 0.8 ± 0.05*** | 0.79 ± 0.05*** | 0.85 ± 0.06 | 0.72 ± 0.08** | 0.82 ± 0.16** | 0.69 ± 0.13 |
| TPA Control | 0.3 ± 0 | 0.7 ± 0.03*** | 0.88 ± 0.01*** | 0.91 ± 0.02*** | 0.95 ± 0.04*** | 0.9 ± 0.02*** | 0.83 ± 0.02*** | 0.8 ± 0.03*** | 0.73 ± 0.03*** | 0.72 ± 0.05*** |
| Vehicle Control | 0.3 ± 0 | 0.31 ± 0 | 0.32 ± 0 | 0.32 ± 0 | 0.33 ± 0 | 0.34 ± 0.01 | 0.34 ± 0.01 | 0.35 ± 0.01 | 0.33 ± 0.1 | 0.33 ± 0.1 |

Similarly, significant decrease in ear thickness change was also observed on D & E topical application for entire treatment schedule except for Day 5 and Day 6 (P<0.001) (FIG. 24).

Oral application of 3-HX at the two tested concentration significantly decreased the ear edema up to Day 5 in comparison with TPA control (P<0.001). However, from Day 6 onwards marginal decrease in ear thickness change was observed. Similarly, significant decrease in ear thickness change was also observed on oral administration of D & E up to Day 3 only when compared with TPA control (P<0.001) However, marginal decrease in ear thickness change was observed on further D & E treatment (FIG. 25).

Topical treatment with D & E exhibited 31.40% activity against TPA induced inflammation.

A dose-dependent reduction in ear biopsy weight was observed in 3-HX oral administration when compared with TPA control (FIG. 26). 3-HX at concentration of 500 mg/kg and 1000 mg/kg exhibited 11.40% and 14.90% activity respectively; however no statistical difference was obtained among the 3-HX oral treated and TPA control group. D & E oral administration also reduced ear punch biopsy thickness when compared with TPA control and exhibited 21.93% activity. However, no statistical difference was obtained among the D & E treated animals and TPA control group.

TABLE 6

Effect of 3-HX and D & E treatment on Ear Thickness Change
(Unit: mm; Mean ± SEM)

| Treatment | Day-1 | Day-2 | Day-3 | Day-4 | Day-5 | Day-6 | Day-7 | Day-8 | Day-9 |
|---|---|---|---|---|---|---|---|---|---|
| 3HX, 1:4 Topical | 0.24 ± 0.01 | 0.24 ± 0.04*** | 0.42 ± 0.04* | 0.48 ± 0.02 | 0.38 ± 0.05** | 0.45 ± 0.04 | 0.42 ± 0.06 | 0.28 ± 0.05 | 0.27 ± 0.03 |
| 3HX, 1:8 Topical | 0.28 ± 0.00 | 0.23 ± 0.04*** | 0.39 ± 0.03** | 0.56 ± 0.01 | 0.36 ± 0.03** | 0.42 ± 0.02 | 0.37 ± 0.05 | 0.33 ± 0.07 | 0.22 ± 0.04* |
| 3HX, 500 mpk, Oral | 0.26 ± 0.00 | 0.25 ± 0.05*** | 0.37 ± 0.04*** | 0.51 ± 0.04 | 0.41 ± 0.04* | 0.47 ± 0.03 | 0.39 ± 0.05 | 0.38 ± 0.04 | 0.36 ± 0.03 |
| 3HX, 1000 mpk, Oral | 0.32 ± 0.00 | 0.3 ± 0.03*** | 0.44 ± 0.02* | 0.6 ± 0.04 | 0.42 ± 0.03* | 0.43 ± 0.02 | 0.37 ± 0.03 | 0.4 ± 0.02 | 0.49 ± 0.02 |
| D&E, Topical | 0.25 ± 0.00 | 0.33 ± 0.03*** | 0.35 ± 0.05*** | 0.51 ± 0.04 | 0.49 ± 0.01 | 0.36 ± 0.03* | 0.2 ± 0.03*** | 0.22 ± 0.02** | 0.18 ± 0.02*** |
| D&E, Oral | 0.35 ± 0.00 | 0.33 ± 0.03*** | 0.37 ± 0.04*** | 0.5 ± 0.05 | 0.48 ± 0.05 | 0.55 ± 0.05 | 0.42 ± 0.06 | 0.52 ± 0.08 | 0.39 ± 0.16 |
| TPA Control | 0.39 ± 0.00*** | 0.58 ± 0.03*** | 0.61 ± 0.01*** | 0.64 ± 0.02*** | 0.59 ± 0.04*** | 0.53 ± 0.02*** | 0.5 ± 0.02*** | 0.43 ± 0.03*** | 0.42 ± 0.03*** |
| Vehicle Control | 0.01 ± 0 | 0.02 ± 0 | 0.02 ± 0 | 0.03 ± 0 | 0.04 ± 0.00 | 0.04 ± 0.01 | 0.04 ± 0.01 | 0.03 ± 0.01 | 0.03 ± 0.01 |

Each column represents mean±SEM of n=6 mice. Data was statistically analyzed by Two way ANOVA followed by Posthoc Bonferroni test. *P<0.001,P<0.01 and *P<0.05 for vehicle control Vs TPA control; and for treatment Vs TPA control.

FIG. 24 illustrates effects of oral application of 3-HX and D & E on Ear Thickness Change (Effect of 3-HX and D & E oral treatment on thickness change in TPA induced mouse ear).

FIG. 25 illustrates effects of oral application of 3-HX and D & E on Ear Thickness Change (Effect of 3-HX and D & E oral treatment on thickness change in TPA induced mouse ear).

Effects of Treatments on Ear Punch Biopsy Weight

On Day 10, all the experimental animals were euthanized and a standard 4 mm ear punch biopsy was collected and weighed. Significant increase in biopsy weight was observed in TPA control (P<0.01) when compared with vehicle control as depicted in Table 7. Ear punch biopsy weight of 3-HX (1:4; topical) treated mice was found to be significantly reduced in comparison to TPA control (P<0.05). However, marginal reduction in ear punch biopsy weight was observed on topical treatment of 3-HX at the ratio of 1:8. Based upon punch biopsy weight, the % activity of 3-HX at both the tested ratios of 1:4 and 1:8 were calculated and was found to be 29.34% and 17.58% respectively. Significant reduction in punch biopsy weight was also observed in D & E topical treatment group (P<0.05) when compared with TPA control.

TABLE 7

Effect of 3-HX and D & E treatment on Ear Punch Biopsy Weight
(Unit: mg; Mean ± SEM)

| Treatment | Biopsy Weight (mg) |
|---|---|
| 3-HX (1:4); Topical | 7.25 ± 0.33* |
| 3-HX (1:8); Topical | 8.46 ± 1.05 |
| 3HX-500 mg/kg; Oral | 9.09 ± 1.14 |
| 3HX-1000 mg/kg; Oral | 8.73 ± 0.34 |
| D & E; Topical | 7.04 ± 0.29* |
| D & E; Oral | 8.01 ± 0.58 |
| TPA control | 10.26 ± 0.82** |
| Vehicle control | 3.08 ± 0.21 |

Each point represents the mean ± SEM of the n = 6 mice per group.
**P < 0.01 for Vechile Control Vs TPA control and
*P < 0.05 for treatment Vs TPA control.

Each point represents the mean±SEM of n=6 mice per group. **P<0.01 for Vehicle Control Vs TPA control and *P<0.05 for treatment Vs TPA control.

Figure 26:
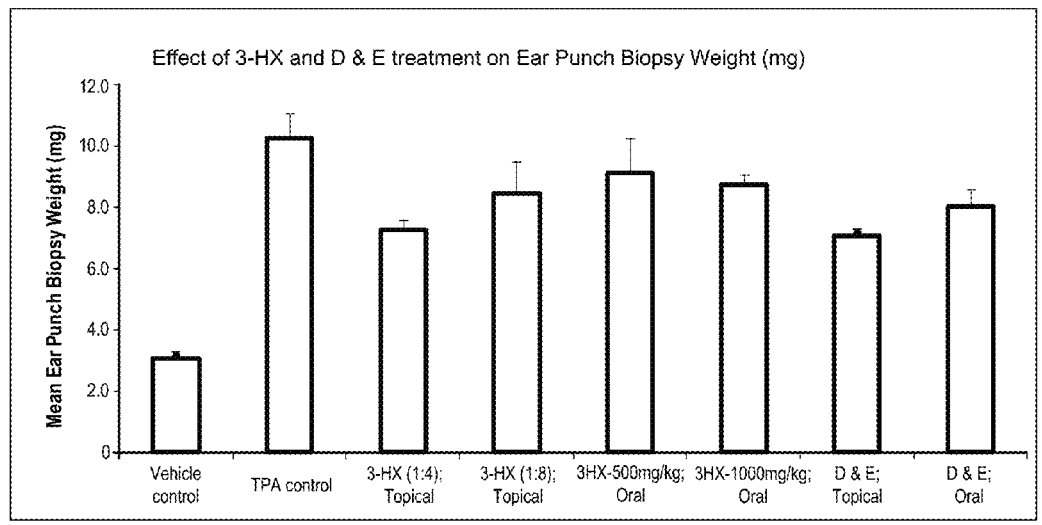
FIG. 26 illustrates effects of combinations of Sheng Di Huang, Da Huang and Jin Yin Hua and of combinations of digoxin and emodin on Ear Punch Biopsy Weight.
Figure 27A:
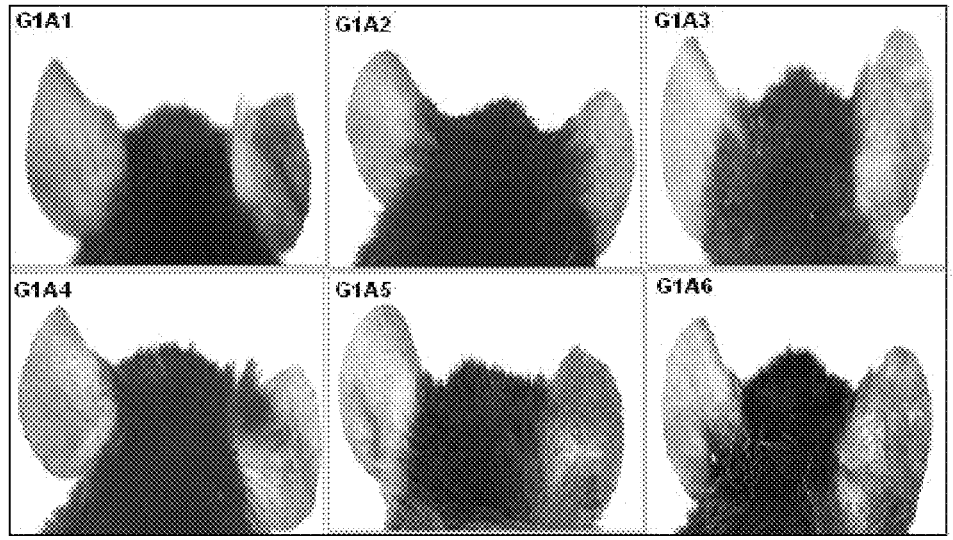
FIGS. 27A-27G show photographs of TPA induced inflammation in mice ears that were represented for all the experimental groups which demonstrated the gross effect of test items.
Figure 27B:
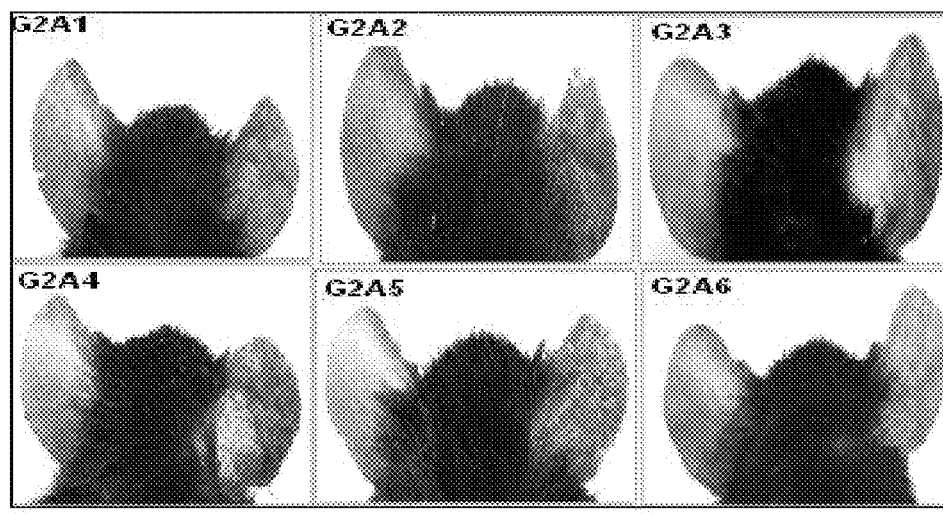
Figure 27C:
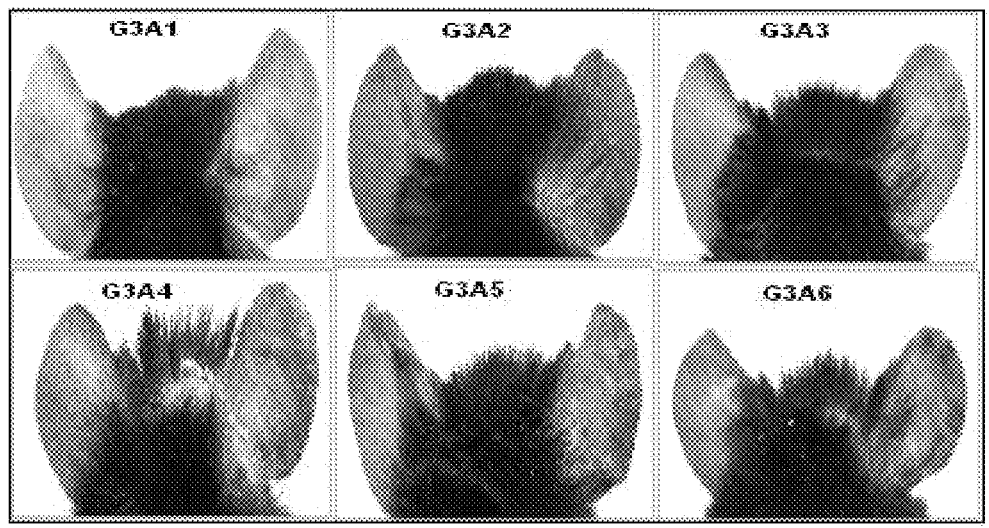
Figure 27D:
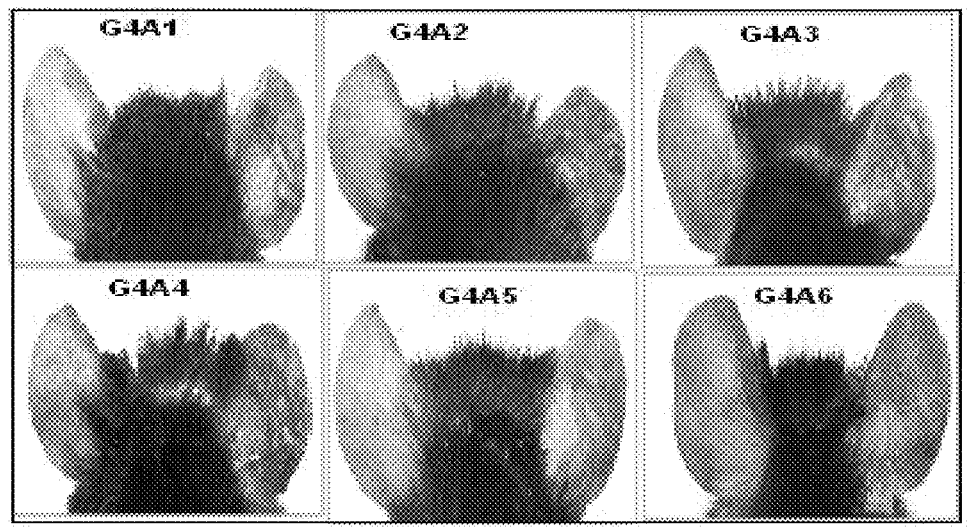
Figure 27E:
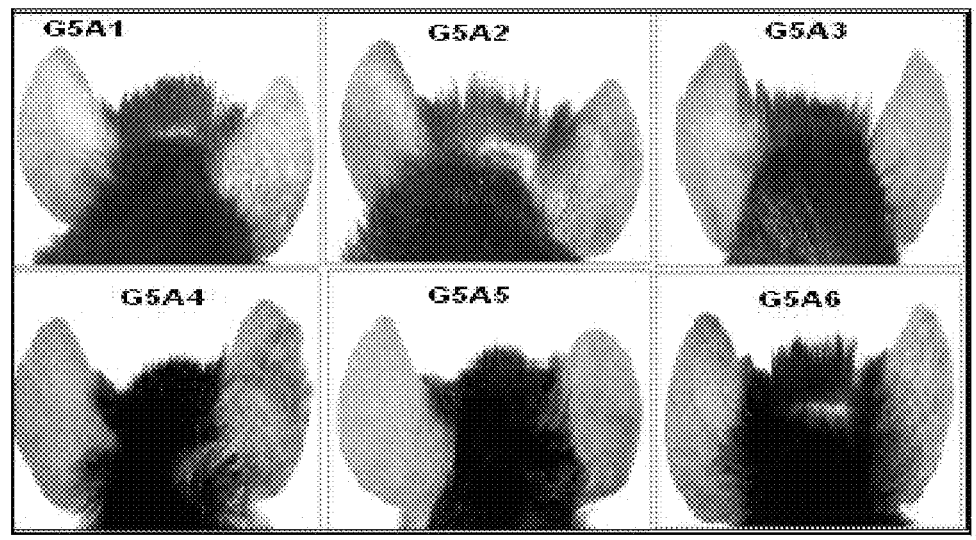
Figure 27F:
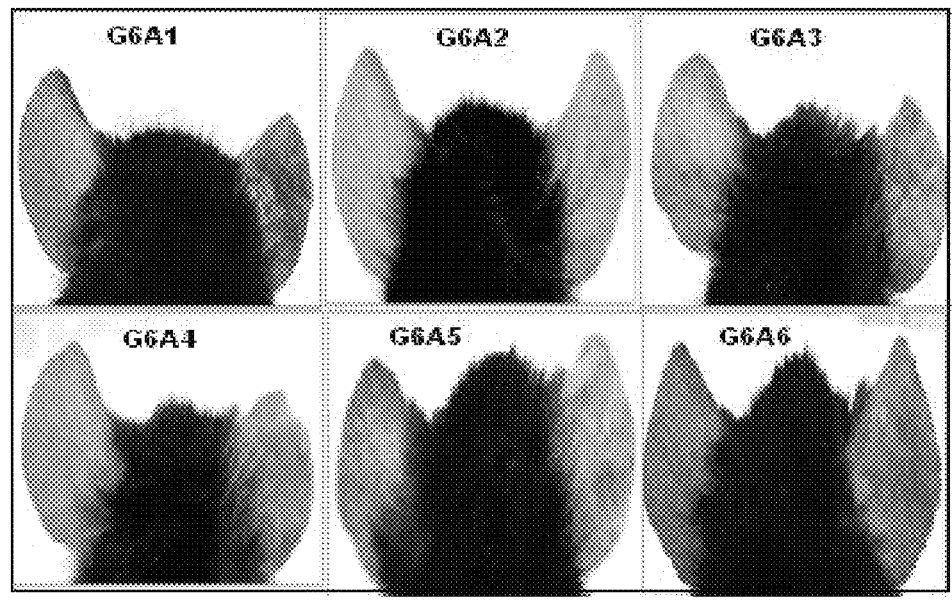
Figure 27G:
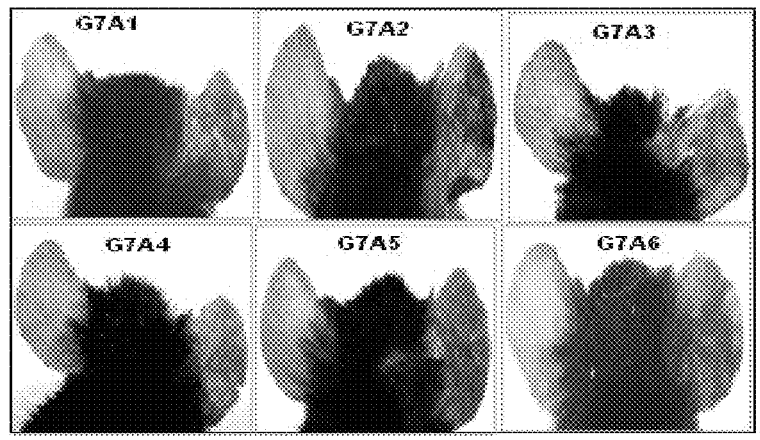

FIG. 26 illustrates effects of 3-HX and D & E treatment on Ear Punch Biopsy Weight (mg).

Photographs of Mice Ears

Photographs of TPA induced inflammation in mice ear were represented for all the experimental groups which demonstrated the gross effect of test items (FIG. 27).

FIGS. 27A-27G illustrates Photographs of ear, including:
Group 1: 3-HX (1:4); Topical: G1A1-G1A6
Group 2: 3-HX (1:8); Topical: G2A1-G2A6

Group 3: 3-HX (500 mg/kg); Oral: G3A1-G3A6
Group 4: 3-HX (1000 mg/kg); Oral: G4A1-G4A6
Group 5: D & E; Topical: G5A1-G5A6
Group 6: D & E; Oral: G6A1-G6A6
Group 7: TPA Control (Right Ear) & Vehicle Control (Left Ear): G7A1-G7A6

Note: G denotes Group Number and A denotes Animal number

Percentage Inhibition

In order to calculate percentage inhibition of ear inflammation on test item treatment, the basal ear thickness change represented by vehicle control was subtracted from each group. The percentage inhibition of ear inflammation by test items was calculated as tabulated in table 8.

Figure 28:
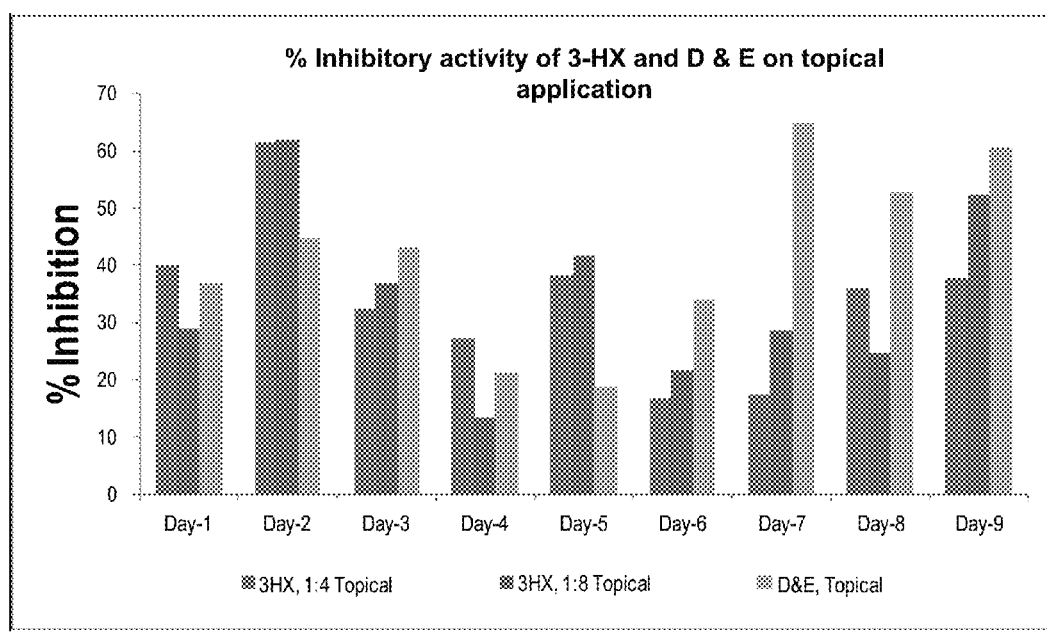
FIG. 28 illustrates % Inhibition of Ear Inflammation on topical treatment.

FIG. 28 depicts the % inhibition of ear inflammation on topical application of 3-HX and D & E. 3-HX at the ratio of 1:4 exerted 35.96% activity on Day 8 which sustained up to Day 9. 3-HX at the ratio of 1:8 exerted maximum inhibition activity of 52.44% on Day 9 treatment. Similarly, topical application of D & E exerted 64.94% inhibitory activity from Day 7 which sustained up to Day 9 treatment.

Figure 29:
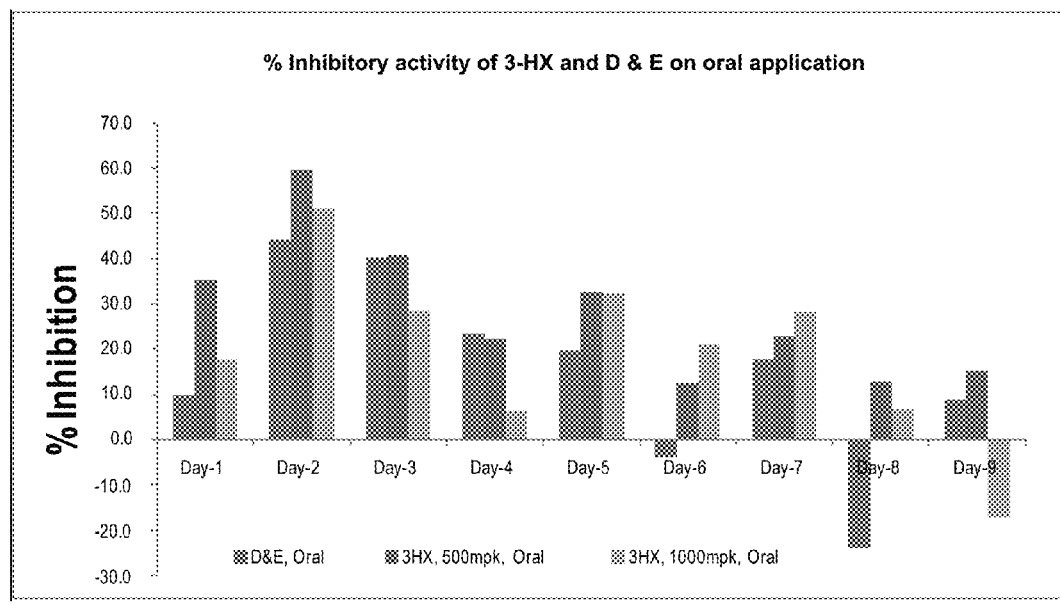
FIG. 29 illustrates % Inhibition of Ear Inflammation on oral treatment.
Figure 30A:
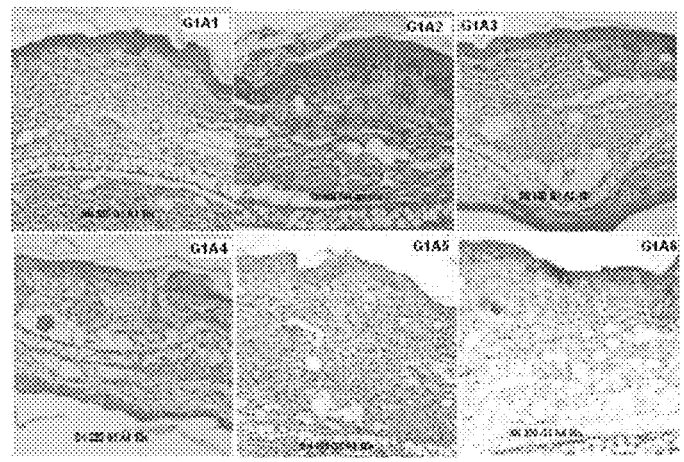
FIGS. 30A-30H illustrate histopathological findings in accordance with certain embodiments.
Figure 30B:
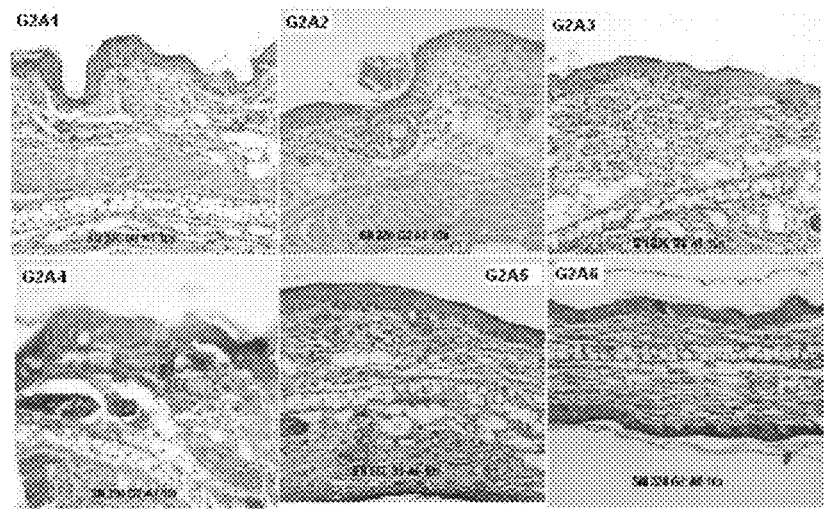
Figure 30C:
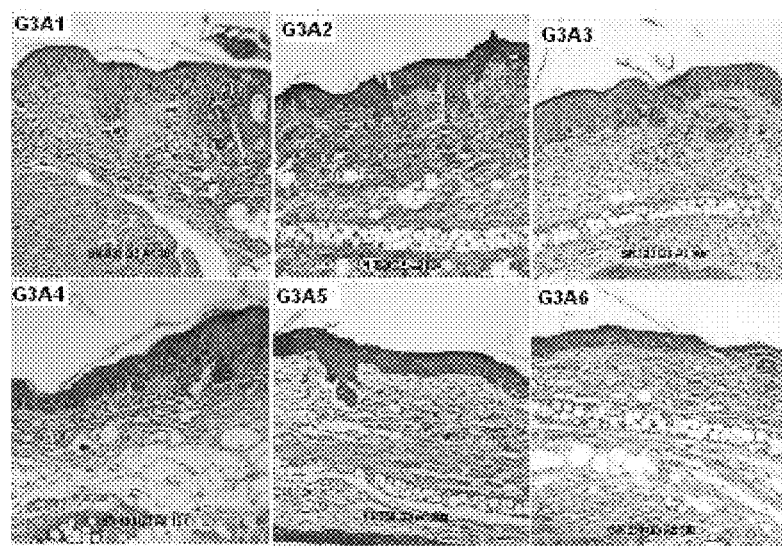
Figure 30D:
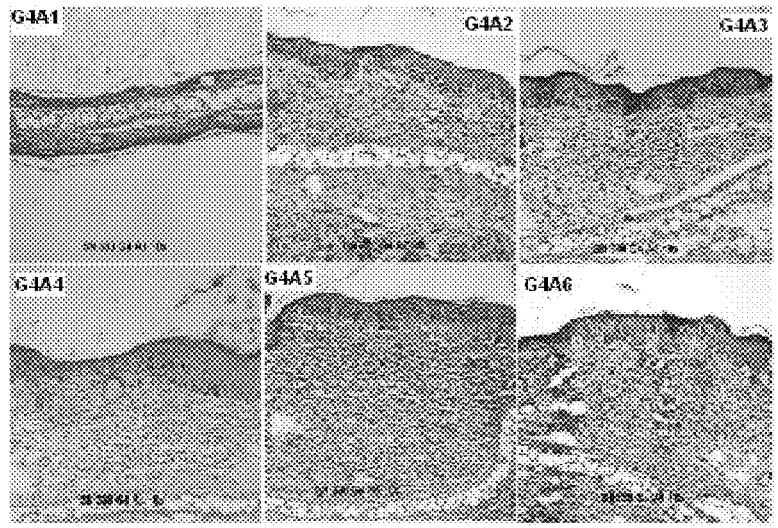
Figure 30E:
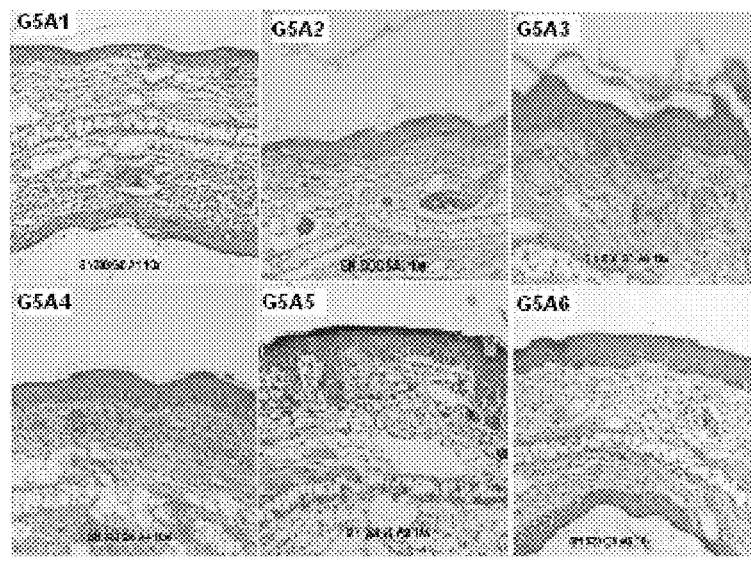
Figure 30F:
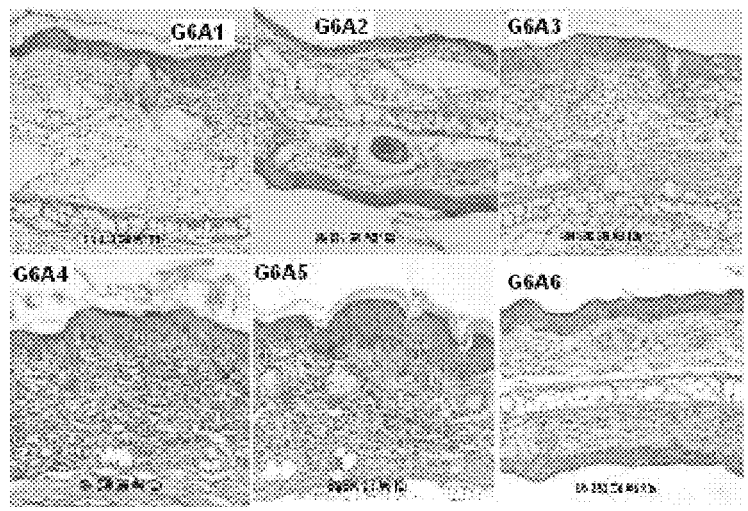
Figure 30G:
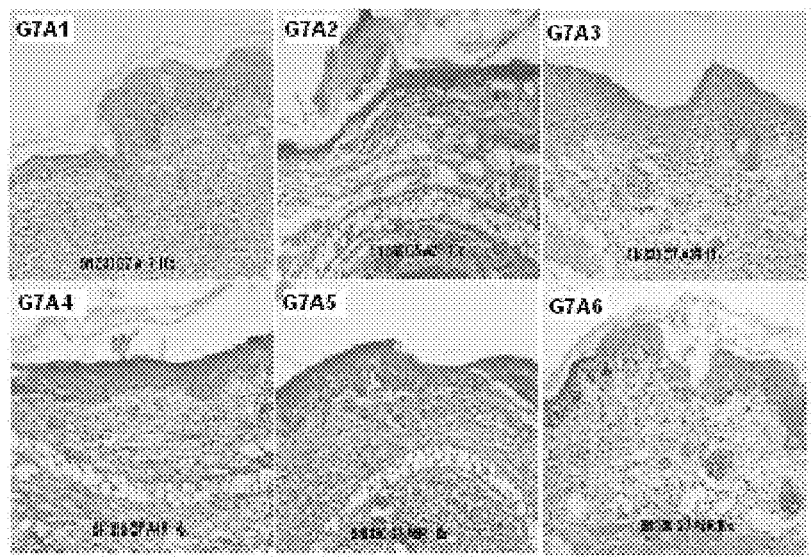
Figure 30H:
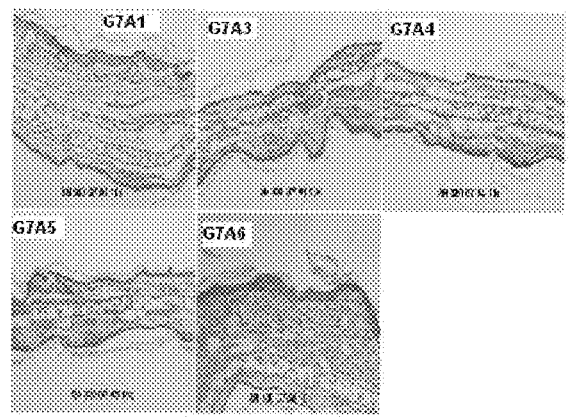

FIG. 29 depicted the % inhibition of ear inflammation on oral administration of 3-HX and D & E. 3-HX at both the doses of 500 mg/kg and 1000 mg/kg exhibited approximately 32% inhibitory activity on Day 5 which subsequently got decreased on further treatment up to Day 9. Similarly, D & E oral administration exerted marginal inhibitory activity against TPA induced inflammation.

ness with almost nil hyperkeratosis and moderate edema. Moreover, severe inflammatory cell infiltration in the dermis was also observed. A significant increase in epidermal ear thickness ($P<0.01$) was also observed in TPA control group when compared with vehicle control (Table 9).

Topical administration of 3-HX at the ratio of 1:4 showed almost nil hyperkeratosis and moderate edema. However, severe inflammatory cell infiltration was observed upon 10 days topical application. Similarly, topical administration of 3-HX at the ratio of 1:8 showed mild hyperkeratosis and edema with severe inflammatory cell infiltration. D & E topical application for 10 consecutive days resulted into moderate hyperkeratosis with moderate edema and infiltration of inflammatory cells. The epidermal thickness was also observed to be significantly reduced on 3-HX topical treatment at both the ratios when compared with TPA control ($P<0.05$).

Figure 31:
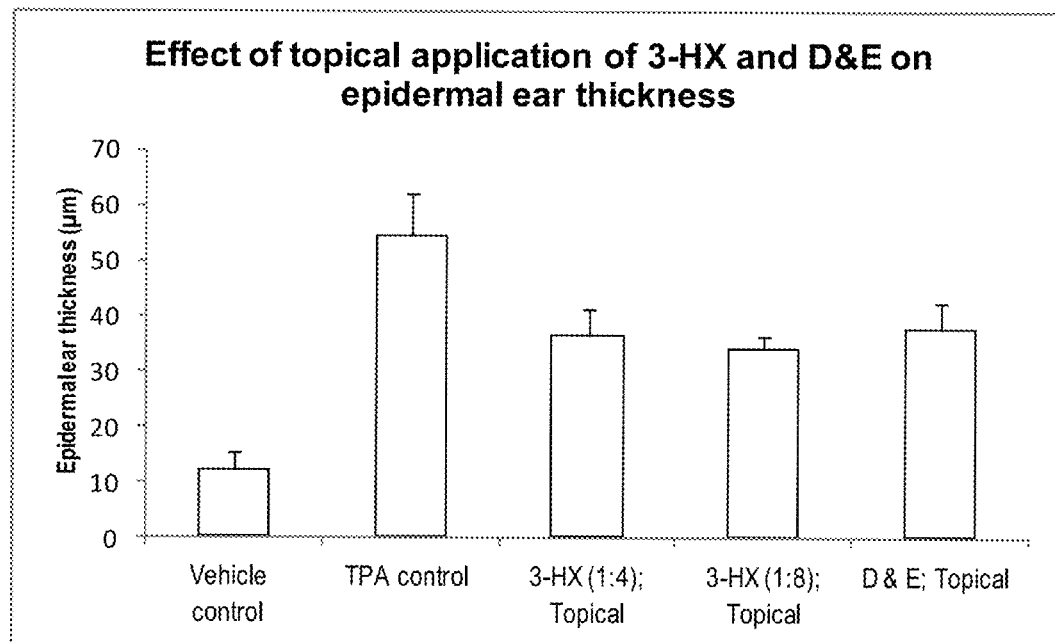
FIG. 31 illustrates effects of topical application of Sheng Di Huang, Da Huang and Jin Yin Hua and of combinations of digoxin and emodin on epidermal ear thickness.

However, on D & E topical application no significant results were obtained when compared with TPA control (FIG. 31).

Oral administration of 3-HX at the low dose of 500 mg/kg resulted into mild hyperkeratosis and edema with moderate to severe infiltration of inflammatory cells. 3-HX at the high dose of 1000 mg/kg resulted into mild to moderate hyperkeratosis and edema with severe infiltration of inflammatory cells. Similarly, oral administration of D & E leads to mild hyperkeratosis with moderate edema and severe inflammatory cell infiltration. The epidermal ear thickness was also found to be significantly reduced on 3-HX treatment at

TABLE 8

% Inhibitory Activity of Ear Inflammation

| Treatment | Day-1 | Day-2 | Day-3 | Day-4 | Day-5 | Day-6 | Day-7 | Day-8 | Day-9 |
|---|---|---|---|---|---|---|---|---|---|
| 3HX (1:4); Topical | 39.86 | 61.42 | 32.25 | 27.16 | 38.41 | 16.90 | 17.34 | 35.96 | 37.68 |
| 3HX (1:8); Topical | 28.99 | 62.02 | 37.01 | 13.44 | 41.63 | 21.72 | 28.54 | 24.72 | 52.44 |
| 3HX (500 mg/kg); Oral | 35.36 | 59.55 | 40.91 | 22.25 | 32.46 | 12.41 | 22.76 | 12.92 | 15.19 |
| 3HX (1000 mg/kg); Oral | 17.68 | 50.94 | 28.35 | 6.45 | 32.16 | 21.03 | 28.17 | 6.60 | −17.05 |
| D&E; Topical | 36.81 | 44.91 | 43.10 | 21.44 | 18.75 | 34.02 | 64.94 | 52.81 | 60.74 |
| D&E; Oral | 9.71 | 44.21 | 39.96 | 23.43 | 19.76 | −3.91 | 17.47 | −24.02 | 8.74 |

FIG. 28 shows % Inhibition of Ear Inflammation on topical treatment (% Inhibitory activity of 3-HX and D & E on topical application).

FIG. 29 shows % Inhibition of Ear Inflammation on oral treatment (% Inhibitory activity of 3-HX and D & E on oral application).

Histopathological and Immunohistochemistry Findings

Figure 32:
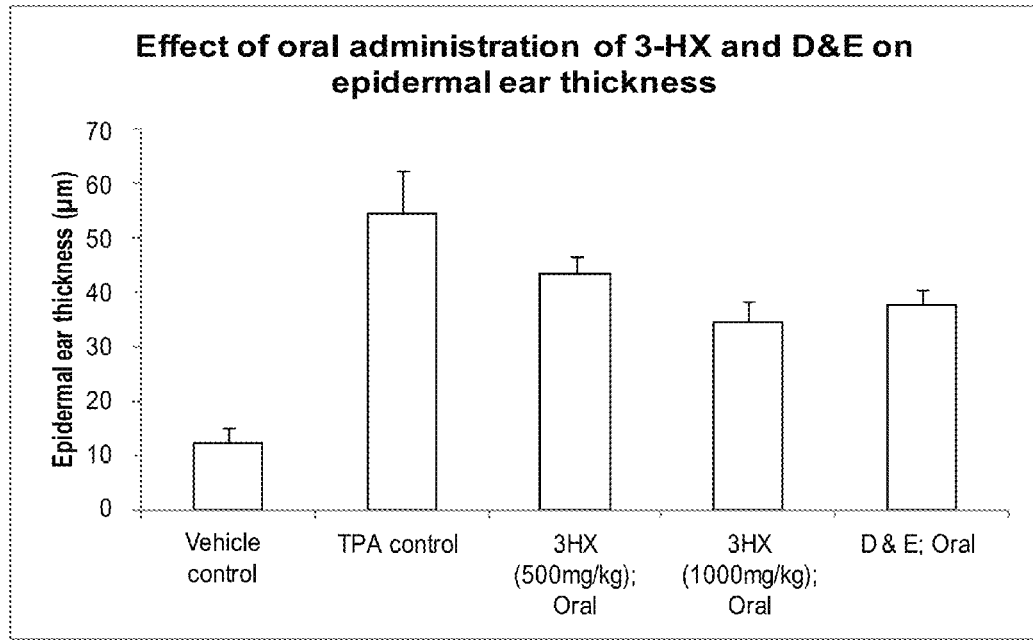
FIG. 32 illustrates effects of oral applications of Sheng Di Huang, Da Huang and Jin Yin Hua and of combinations of digoxin and emodin on epidermal ear thickness.

The H&E-stained ear sections of all the experimental groups are represented in FIG. 30. Edema and inflammatory cell infiltration are scored as nil (−), mild (+), moderate (++) and severe (+++). Moreover, the epidermal thickness was also calculated for all the experimental groups. Repeated TPA application resulted in a marked increase in ear thickhigher dose of 1000 mg/kg alone ($P<0.05$) (FIG. 32). However, in other oral treatment groups no significant differences were obtained in comparison with TPA control.

FIGS. 30a-30h: Histopathological Findings

Group 1: 3-HX (1:4); Topical. Photographs of H&E-stained mouse ear cross-sections of 3-HX (1:4; topical) treated mice in the TPA inflammation model. Reduction in hyperkeratosis and edema was observed (10× magnification).

Group 2: 3-HX (1:8); Topical. Photographs of H&E-stained mouse ear cross-sections of 3-HX (1:8; topical) treated mice in the TPA inflammation model. Reduction in hyperkeratosis and edema was observed (10× magnification).

Group 3: 3-HX (500 mg/kg); Oral. Photographs of H&E-stained mouse ear cross-sections of 3-HX (500 mg/kg; oral) treated mice in the TPA inflammation model. Reduction in hyperkeratosis and edema was observed (10× magnification).

Group 4: 3-HX (1000 mg/kg); Oral. Photographs of H&E-stained mouse ear cross-sections of 3-HX (1000 mg/kg; oral) treated mice in the TPA inflammation model. Reduction in hyperkeratosis and edema was observed (10× magnification).

Group 5: D & E; Topical. Photographs of H&E-stained mouse ear cross-sections of D & E topically treated mice in the TPA inflammation model. Reduction in hyperkeratosis, edema and inflammatory cell infiltration was observed (10× magnification).

Group 6: D & E; Oral. Photographs of H&E-stained mouse ear cross-sections of D & E orally treated mice in the TPA inflammation model. Reduction in hyperkeratosis and edema was observed (10× magnification).

Group 7: TPA Control (Right Ear). Photographs of H&E-stained mouse ear cross-sections in the TPA induced inflammation model. Severe infiltration of inflammatory cells with moderate edema in ears was observed (10× magnification).

Group 7: Vehicle control (Left Ear). Photographs of H&E-stained mouse ear cross-sections of vehicle control group (10× magnification).

TABLE 9

Effect of Test items Treatment on Epidermal ear thickness
(Unit: μm; Mean ± SEM)

| Treatment | Epidermal Ear Thickness |
| --- | --- |
| Vehicle Control | 12.15 ± 3.08 |
| TPA Control | 54.42 ± 7.76** |
| 3-HX (1:4); Topical | 36.41 ± 5.16* |
| 3-HX (1:8); Topical | 34.06 ± 2.46* |
| 3HX-500 mg/kg; Oral | 43.26 ± 3.36 |
| 3HX-1000 mg/kg; Oral | 34.49 ± 3.81* |
| D & E; Topical | 37.88 ± 4.85 |
| D & E; Oral | 37.48 ± 3.11 |

**$P < 0.01$ for vehicle control compared to TPA Control;
*$P < 0.05$ for TPA Control compared to 3-HX treatment group.

FIG. 31 illustrates effects of topical application of 3-HX and D & E on epidermal ear thickness.

FIG. 32 illustrates effects of oral treatment of 3-HX and D&E on epidermal ear thickness.

Myeloperoxidase (MPO) Activity

Figure 33:
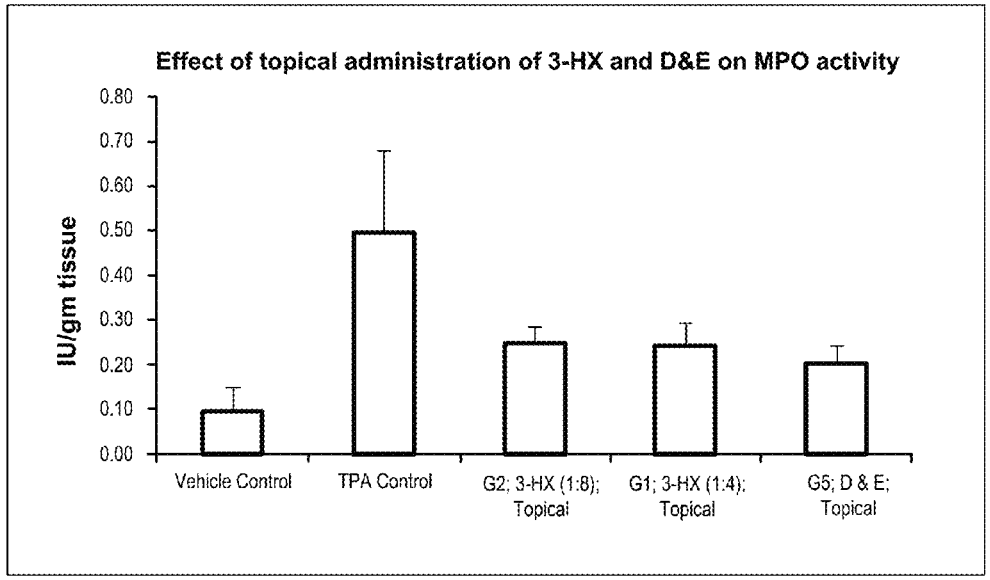
FIG. 33 illustrates effects of topical application of Sheng Di Huang, Da Huang and Jin Yin Hua and of combinations of digoxin and emodin on MPO activity in TPA induced mice ears.

Table 10 illustrated the effect of test items over enzyme myeloperoxidase, released by neutrophils and macrophages during inflammation process. In the present study, the enzyme activity was found to be markedly enhanced in TPA control group when compared with vehicle control. Topical application of 3-HX at both the ratios profoundly inhibited the MPO activity on 10 days of consecutive application in comparison with TPA control. Topical application of standard D & E showed maximum inhibition of MPO activity among all the topical treatment groups (FIG. 33).

Figure 34:
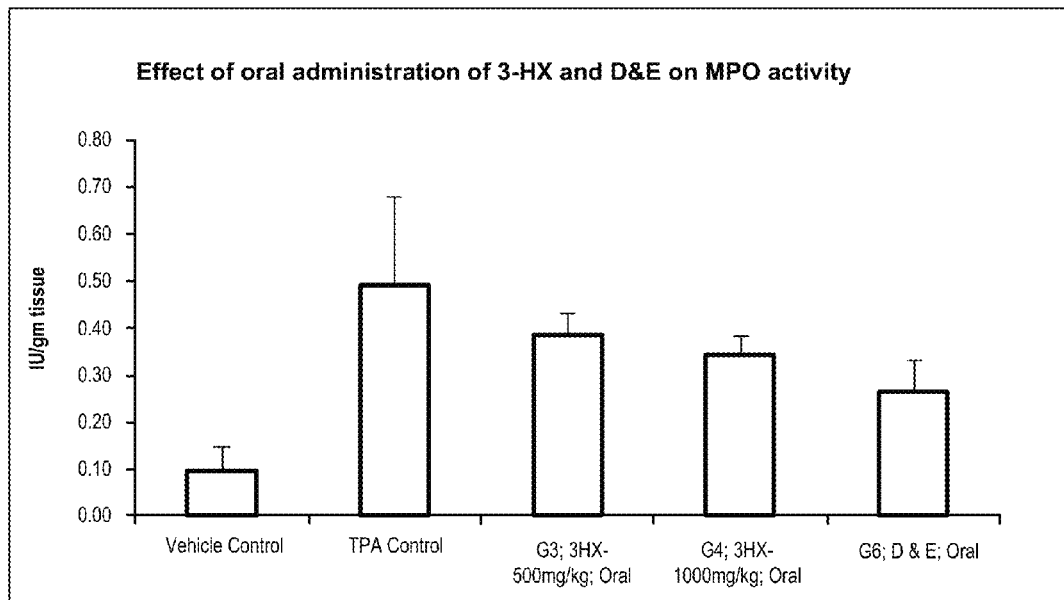
FIG. 34 illustrates effects of oral administration of Sheng Di Huang, Da Huang and Jin Yin Hua and of combinations of digoxin and emodin on MPO activity in TPA induced mice ears.

Oral administration of 3-HX showed dose-dependent inhibition of enzyme MPO against TPA induced mice ear inflammation. D & E oral treatment also observed to inhibit the MPO levels when compared with TPA control (FIG. 34).

TABLE 10

Effect of Test items Treatment on MPO activity in TPA induced mice ear
(Unit: μm; Mean ± SEM)

| Treatment | IU/gm tissue (Mean ± SEM) |
| --- | --- |
| Vehicle Control | 0.094 ± 0.052 |
| TPA Control | 0.487 ± 0.184 |
| 3-HX (1:4); Topical | 0.238 ± 0.044 |
| 3-HX (1:8); Topical | 0.244 ± 0.037 |
| 3HX-500 mg/kg; Oral | 0.380 ± 0.051 |
| 3HX-1000 mg/kg; Oral | 0.339 ± 0.038 |
| D & E; Topical | 0.196 ± 0.046 |
| D & E; Oral | 0.258 ± 0.068 |

FIG. 33 illustrates effects of topical application of 3-HX and D & E on MPO activity in TPA induced mice ear.

FIG. 34 illustrates effects of oral administration of 3-HX and D&E on MPO activity in TPA induced mice ear.

Nitric Oxide (NO) Activity

Table 11 illustrated the % inhibition of nitric oxide levels in serum of TPA induced inflammation on treatment of test items. Topical application of 3-HX at both the ratios exerted poor inhibitory effect over nitric oxide levels on 10 days of consecutive application. Similarly, topical application of standard D & E also exhibited poor inhibitory response over serum NO levels.

Figure 35:
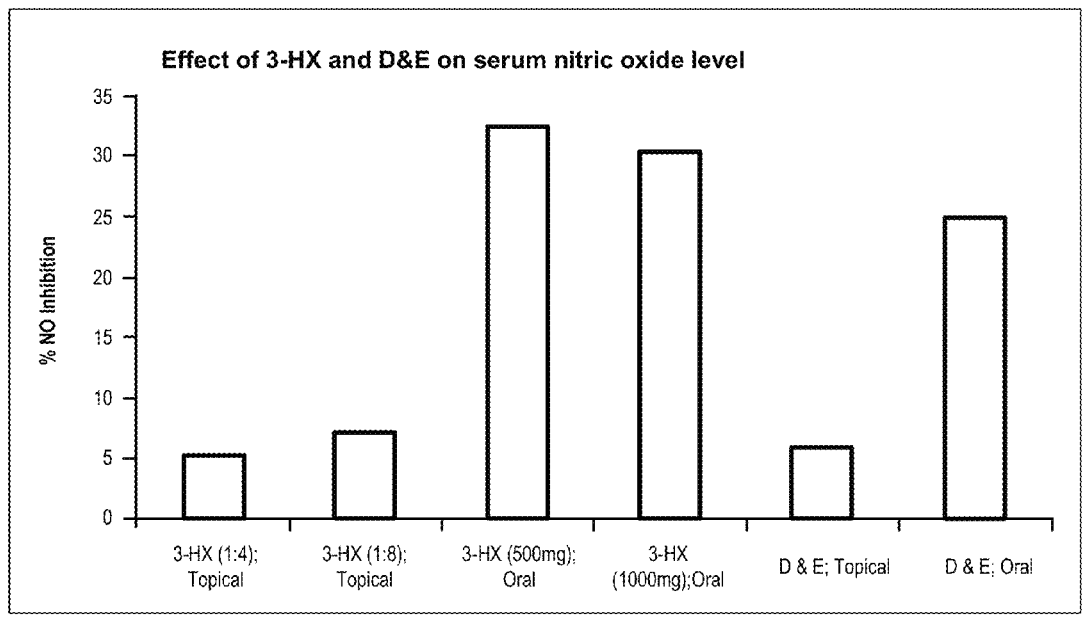
FIG. 35 illustrates the % Inhibition of serum Nitric oxide content on of Sheng Di Huang, Da Huang and Jin Yin Hua and of combinations of digoxin and emodin treatment.

Oral administration of 3-HX at the dose of 500 mg/kg and 1000 mg/kg exhibited 32.53% and 30.62% inhibitory activity respectively over serum nitric oxide content against TPA induced inflammation. D & E oral treatment also observed to exert 25.10% inhibitory activity (FIG. 35).

TABLE 11

Effect of Test items Treatment on % Inhibition of Nitric
oxide level in serum of TPA induced inflammation

| Treatment | % Inhibition |
| --- | --- |
| 3-HX (1:4); Topical (n = 6) | 5.35 |
| 3-HX (1:8); Topical (n = 3) | 7.10 |
| 3-HX (500 mg); Oral (n = 4) | 32.53 |
| 3-HX (1000 mg); Oral (n = 4) | 30.62 |
| D & E; Topical (n = 4) | 6.02 |
| D & E; Oral (n = 4) | 25.10 |

Note:
n represents plasma samples size analyzed for NO activity

FIG. 35 shows % Inhibition of serum Nitric oxide content on 3-HX and D&E treatment (Effect of 3-HX and D&E on serum nitric oxide level).

These examples demonstrate anti-psoriatic potential of 3-HX and D & E on both topical and oral treatment in TPA induced ear inflammation in C57BL/6 mice. The results demonstrated no significant changes in body weight among all the experimental groups. However, in % body weight change, a marginal reduction was observed on oral administration of D & E and high dose of 3-HX, although both ranged within the tolerable range.

In the present study results marked induction of ear inflammation on repeated TPA application was observed as indicated by significant increase in ear thickness. Topical application of TPA is reported to induce cutaneous inflammation and epidermal hyperplasia (Clark et al., 1985). The TPA application resulted in a series of events of numerous cellular, biochemical, and molecular changes that eventually lead to the pathological alterations of the mouse skin (Kensler et al., 1987; Nakamura et al., 1998, 2000). Among the topically treated groups, high concentration of 3-HX (1:4) and D&E was found to exert maximum anti-inflammatory activity as indicated by significant reduction in ear thickness. Among the orally administered experimental groups, low dose of 3-HX (500 mg/kg) exhibited maximum reduction in ear thickness followed by D & E and high dose of 3-HX (1000 mg/kg).

The effect of topical and oral treatment of test items was also examined over TPA-induced ear thickness change which also represents inflammatory edema. Topical application of 3-HX (1:4) exerted maximum reduction in ear thickness change followed by D & E and low concentration of 3-HX (1:8). Among the orally administered groups, low dose of 3-HX (500 mg/kg) rendered maximum reduction in ear thickness change followed by D & E and high dose of 3-HX (1000 mg/kg). The overall % inhibitory activity of test items based upon the ear thickness and ear thickness change demonstrated that topical application of D & E resulted in maximum inhibition of ear thickness followed by 3-HX (1:8) and 3-HX (1:4). On the other side, oral application of all the test items exerted marginal inhibitory activity against TPA induced ear inflammation in mice.

The effect of test items was further evaluated by measuring the standard 4 mm punch biopsy weight after completion of treatment schedule. 10 consecutive day TPA application resulted in profound increase in punch biopsy weight of mice ear suggesting the chronic inflammatory response. Topical application of D & E exerted maximum reduction in ear punch biopsy weight followed by 3-HX (1:4) and 3-HX (1:8). Oral administration of 3-HX and D & E resulted in marginal reduction in ear punch biopsy weight suggesting the beneficial effect of test items on topical application in comparison with oral treatment.

To further explore the anti-psoriatic potential of test items, the epidermal ear thickness was evaluated in histopathological photographs. The histopathogical findings were in accordance with punch biopsy weight results where topical application of test items was found to exert better effect against TPA induced increase in epidermal ear thickness ear in comparison with orally treated experimental groups. Moreover, marked reduction in hyperkeratosis, ear edema and inflammatory cell infiltration was also observed among all the treatment groups when compared with TPA control.

In the present study, the effect of test items was also investigated over inflammatory biomarkers viz., enzyme myeloperoxidase and nitric oxide in TPA model of inflammation. In the present study marked increase in MPO activity was observed in TPA control mice ear homogenate which is in accordance with the previous reports (Lee et al. 2009). MPO is commonly used as an index of granulocyte infiltration and the enzyme inhibition is indicative of anti-inflammatory activity in the chronic inflammation model (Ajuebor et al. 2000). Topical application of D & E resulted in maximum suppression of enzyme activity followed by 3-HX (1:4) and 3-HX (1:8). Among the orally treated experimental groups, D & E exerted marked suppression of enzyme activity whereas 3-HX exhibited marginal activity.

Similarly, marked increase in nitric oxide levels were observed in TPA control group. In the present study, oral administration of test items partially inhibited the generation of nitric oxide content against TPA induced mice inflammation.

The embodiments have been described as demonstrated anti-psoriatic potential of 3-HX and D & E on both topical and oral application in TPA-induced ear inflammation model using C57BL/6 mice. Based upon the present findings, it is suggested that topical application of D & E and 3-HX may act as potential therapeutic intervention for the treatment of inflammatory skin diseases like psoriasis through inhibition of myeloperoxidase activity. Future investigations are recommended in-order to find out the mechanism of action which is required for the development of novel therapeutics for the treatment of psoriasis.

The following are incorporated by reference:

Rajp A, Adu D and Savage CO (2007). Meta-analysis of myeloperoxidase G-463/A polymorphism in anti-neutrophil cytoplasmic autoantibody-positive vasculitis. Clinical and Experimental Immunology. 149: 251-256.

Clark S D, Wilhelm S M, Stricklin G P, Welgus H G (1985) Coregulation of collagenase and collagenase inhibitor production by phorbol myristate acetatein human skin fibroblasts. Arch. Biochem. Biophys. 241, 36-44.

Kensler T W, Egner P A, Moore K G, Taffe B G, Twerdok L E, Trush M A (1987) Role of inflammatory cells in the metabolic activation of polycyclic aromatic hydrocarbons in mouse skin. Toxicol. Appl. Pharmacol. 90, 337-346.

Nakamura Y, Murakami A, Ohto Y, Torikai K, Tanaka T, Ohigashi H (1998) Suppression of tumor promoter induced oxidative stress and inflammatory responses in mouse skin by superoxide generation inhibitor 10-acetoxychavicol acetate. Cancer Res. 58, 4832-4839.

Nakamura Y, Torikai K T, Ohto Y, Murakami A, Tanaka T, Ohigashi H (2000) A simple phenolic antioxidant protocatechuic acid enhances tumor promotion and oxidative stress in female ICR mouse skin: dose- and timing-dependent enhancement and involvement of bioactivation by tyrosinase. Carcinogenesis 21, 1899-1907.

Lee D Y, Choi G, Yoon T, Cheon M S, Choo B K, Kim H K (2009) Anti-inflammatory activity of *Chrysanthemum indicum* extract in acute and chronic cutaneous inflammation. Journal of Ethnopharmacology 123:149-154.

Ajuebor M N, Singh A, Wallace J L (2000) Cyclooxygenase-2-derived prostaglandin D(2) is an early anti-inflammatory signal in experimental colitis. American Journal of Physiology Gastrointestinal and Liver Physiology 279, G238-G244.

| LIST OF TABLES |
|---|
| Table No. Heading/Title |
| 1. Oral purgative $ED_{50}$ values of the anthraquinones. |
| 2. Allocation of animals |
| 3. Effect of 3-HX and D & E treatment on Body Weight |
| 4. Effect of 3-HX and D & E treatment on % Body Weight Change |
| 5. Effect of 3 -HX and D & E treatment on Ear Thickness |
| 6. Effect of 3-HX and D & E treatment on Ear Thickness Change |
| 7. Effect of 3-HX and D & E treatment on Ear Punch Biopsy Weight |
| 8. % Inhibitory Activity of Ear Inflammation |
| 9. Effect of Test items Treatment on Epidermal ear thickness |
| 10. Effect of Test items Treatment on MPO activity in TPA induced mice ear |
| 11. Effect of Test items Treatment on % Inhibition of Nitric oxide level in serum of TPA induced inflammation |

| ABBREVIATIONS USED | |
|---|---|
| Abbreviation | Explanation |
| ° C. | Degree Centigrade |
| % | Percentage |
| μl | Microliter |

-continued

| ABBREVIATIONS USED | |
|---|---|
| Abbreviation | Explanation |
| μm | Micrometer |
| ANOVA | Analysis of variance |
| CPCSEA | Committee for the Purpose of Control and Supervision of Experiments on Animals |
| DMSO | Dimethylsulfoxide |
| DRF | Dabur Research Foundation |
| ETC | Ear Thickness Change |
| M | Molar |
| mg | milligram |
| ml | milliliter |
| ml/kg | milliliter/kilogram |
| mm | millimeter |
| mM | millimolar |
| SEM | Standard Error Mean |
| SD | Standard Deviation |
| TPA | 12-O-Tetradecanoylphorbol-13-Acetate |
| IHC | Immunohistochemistry |
| IU | International Unit |

It is contemplated, as people with ordinary skill in the art would do, that the newly separated compounds may be each individually or in combination used as an ingredient to prepare a pharmaceutical composition for a particular treatment purpose. As it is the status of the art in the pharmaceutical industry, once substantially pure preparations of a compound are obtained, various pharmaceutical compositions or formulations can be prepared from the substantially pure compound using conventional processes or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more processes established in the industry to the practice of the present invention. Alternatively, people of ordinary skill in the art may modify the existing conventional processes to better suit the compounds of the present invention. For example, the patent or patent application databases provided at USPTO official website contain rich resources concerning making pharmaceutical formulations and products from effective chemical compounds. Another useful source of information is Handbook of Pharmaceutical Manufacturing Formulations, edited by Sarfaraz K. Niazi and sold by Culinary & Hospitality Industry Publications Services, which is incorporated by reference.

While the invention has been described in terms of several embodiments, those skilled in the art will recognize that the invention is not limited to the embodiments described, but can be practiced with modification and alteration within the spirit and scope of the appended claims.

The description is thus to be regarded as illustrative instead of limiting of the invention as set forth in the appended claims including structural and functional equivalents thereof

What is claimed is:

1. A method of treating psoriasis, comprising administering to a patient diagnosed with psoriasis a dosage composition comprising a combination of Sheng Di Huang, Da Huang and Jin Yin Hua;
    wherein said dosage composition comprises between 18% and 90% of said Sheng Di Huang, between 4% and 64% of said Da Huang, and between 4% and 64% of said Jin Yin Hua,
    wherein said dosage composition comprises at least 60 wt. % of said combination.

2. The method of claim 1, comprising administering the dosage composition topically.

3. The method of claim 1, comprising administering the dosage composition orally.

4. The method of claim 1, comprising administering the dosage composition subcutaneously.

5. The method of claim 1, comprising administering the dosage composition intravenously.

6. The method of claim 1, wherein the combination comprises at least 25 grams of the Sheng Di Huang, at least 10 grams of the Da Huang, and at least 10 grams of the Jin Yin Hua.

7. The method of claim 1, wherein the combination comprises at least 13.3 grams of the Sheng Di Huang, at least 3.3 grams of the Da Huang, and at least 3.3 grams of the Jin Yin Hua.

8. The method of claim 1, comprising repeating the administering of the dosage composition multiple times over the course of a psoriasis treatment regimen.

9. The method of claim 8, comprising administering over the course of said treatment regimen at least 25 grams of the Sheng Di Huang, at least 10 grams of the Da Huang, and at least 10 grams of the Jin Yin Hua.

10. The method of claim 8, comprising administering over the course of said treatment regimen at least 13.3 grams of the Sheng Di Huang, at least 3.3 grams of the Da Huang, and at least 3.3 grams of the Jin Yin Hua.

11. The method of claim 1, further comprising testing the patient for psoriasis.

12. The method of claim 11, further comprising diagnosing the patient with psoriasis based on the testing.

13. A method of preparing a medicinal dosage composition for treating psoriasis, comprising formulating a combination including Sheng Di Huang, Da Huang and Jin Yin Hua;
    wherein said combination comprises between 18% and 90% of said Sheng Di Huang, between 4% and 64% of said Da Huang, and between 4% and 64% of said Jin Yin Hua,
    wherein said medicinal dosage composition comprises at least 60 wt. % of said combination.

14. The method of claim 13, wherein the combination comprises at least 25 grams of the Sheng Di Huang, at least 10 grams of the Da Huang, and at least 10 grams of the Jin Yin Hua.

15. The method of claim 13, wherein the combination comprises at least 13.3 grams of the Sheng Di Huang, at least 3.3 grams of the Da Huang, and at least 3.3 grams of the Jin Yin Hua.

* * * * *